US010821079B2

(12) United States Patent
Alkon et al.

(10) Patent No.: US 10,821,079 B2
(45) Date of Patent: *Nov. 3, 2020

(54) PKC ACTIVATORS AND COMBINATIONS THEREOF

(71) Applicant: Cognitive Research Enterprises, Inc., Morgantown, WV (US)

(72) Inventors: Daniel L. Alkon, Bethesda, MD (US); Thomas J. Nelson, Morgantown, WV (US)

(73) Assignee: Cognitive Research Enterprises, Inc., Morgantown, WV (US)

( * ) Notice: Subject to any disclaimer, the term of this patent is extended or adjusted under 35 U.S.C. 154(b) by 177 days.

This patent is subject to a terminal disclaimer.

(21) Appl. No.: 14/357,661

(22) PCT Filed: Nov. 13, 2012

(86) PCT No.: PCT/US2012/064787
§ 371 (c)(1),
(2) Date: May 12, 2014

(87) PCT Pub. No.: WO2013/071282
PCT Pub. Date: May 16, 2013

(65) Prior Publication Data
US 2014/0315990 A1 Oct. 23, 2014

Related U.S. Application Data

(60) Provisional application No. 61/559,141, filed on Nov. 13, 2011.

(51) Int. Cl.
| | | |
|---|---|---|
| *A61K 9/127* | (2006.01) | |
| *A61K 31/203* | (2006.01) | |
| *A61K 31/231* | (2006.01) | |
| *A61K 31/365* | (2006.01) | |
| *A61K 31/215* | (2006.01) | |
| *G01N 33/50* | (2006.01) | |

(52) U.S. Cl.
CPC .......... *A61K 9/1275* (2013.01); *A61K 31/203* (2013.01); *A61K 31/215* (2013.01); *A61K 31/231* (2013.01); *A61K 31/365* (2013.01); *G01N 33/5058* (2013.01)

(58) Field of Classification Search
CPC .. A61K 9/1275; A61K 31/203; A61K 31/231; C07C 69/608
USPC .......................................................... 514/450
See application file for complete search history.

(56) References Cited

U.S. PATENT DOCUMENTS 9,163,032 B2 * 10/2015 Alkon ................... C07C 69/608
2010/0022645 A1 * 1/2010 Nelson ................. A61K 31/045
514/559

OTHER PUBLICATIONS

Mattson, "Apoptosis in Neurodegenerative disorders", 2000, Nature Reviews, vol. 1, pp. 120-129. (Year: 2000).*
Abreu et al. Emerging Biosensing Technologies for Neuroinflammatory and Neurodegenerative disease diagnostics, 2018, Frontiers in Molecular Neuroscience, vol. 13, Article 164, pp. 1-13. (Year: 2018).*
Lee et al. Expert Rev. Neurother., Author Manuscript, available in PMC Aug. 2, 2010, 11 pages (Year: 2010).*
International Search Report and Written Opinion for PCT/US2012/064787, dated Apr. 25, 2003.
Sun et al., "Dual Effects of Bryostatin-1 on Spatial Memory and Depression", European Journal of Pharmacology, vol. 512, No. 1, pp. 43-51 (Apr. 2005).
Sun et al., "Poststroke Neuronal Rescue and Synaptogenesis Mediated in Vivo by Protein Kinase C in Adult Brains", Proceedings of the National Academy of Sciences, vol. 105, No. 36, pp. 13620-13625 (Sep. 2008).
Zohar O., et al., "PKC Activator Therapeutic for Mild Traumatic Brain Injury in Mice", Neurobiology of Disease, vol. 41, No. 2, pp. 329-337, (Feb. 2011).
European Communication dated May 29, 2019 received in European Application No. 12 794 822.2.
European Communication dated Apr. 8, 2020 received in European Application No. 12 794 822.2.

* cited by examiner

*Primary Examiner* — James D. Anderson
(74) *Attorney, Agent, or Firm* — Scully, Scott, Murphy & Presser, P.C.

(57) ABSTRACT

The present disclosure relates to PKC activators and combinations thereof. The disclosure further relates to compositions, kits, uses, and methods thereof.

7 Claims, 44 Drawing Sheets

SH-SY5Y CELLS TREATED WITH
DIFFERENT Aβ SPECIES FOR 20 HR

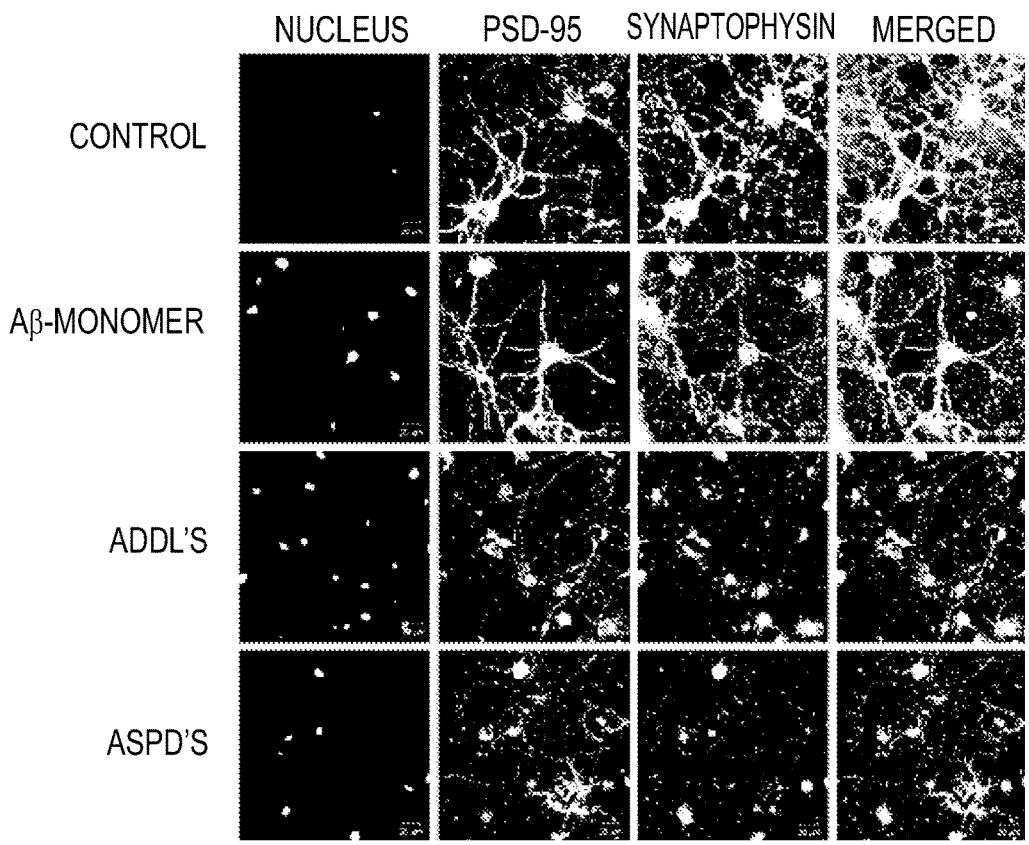
FIG. 9A
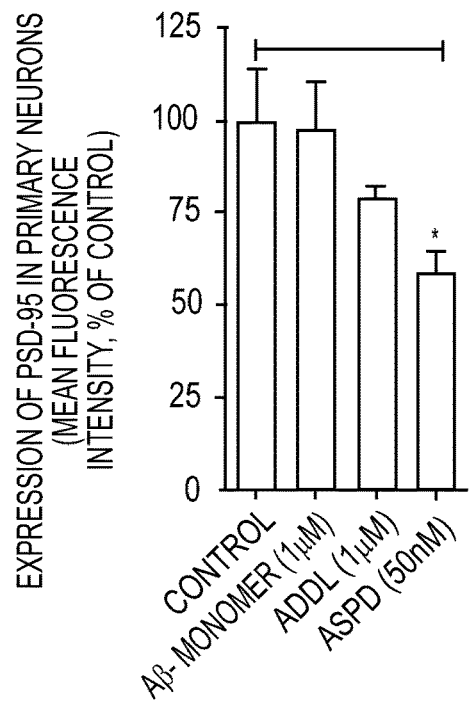 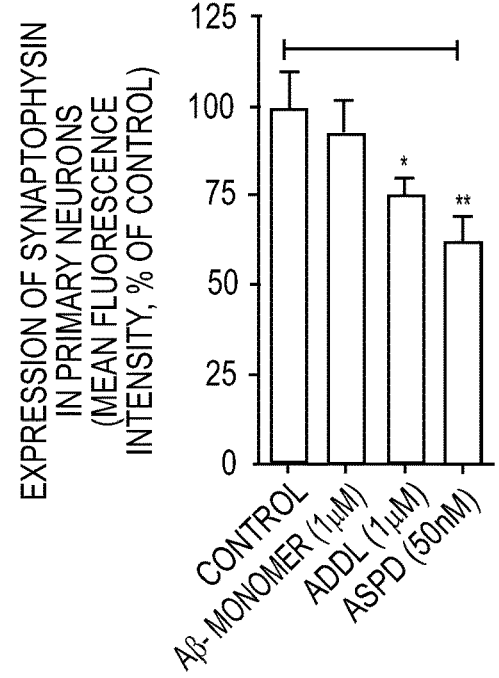
FIG. 9B  FIG. 9C

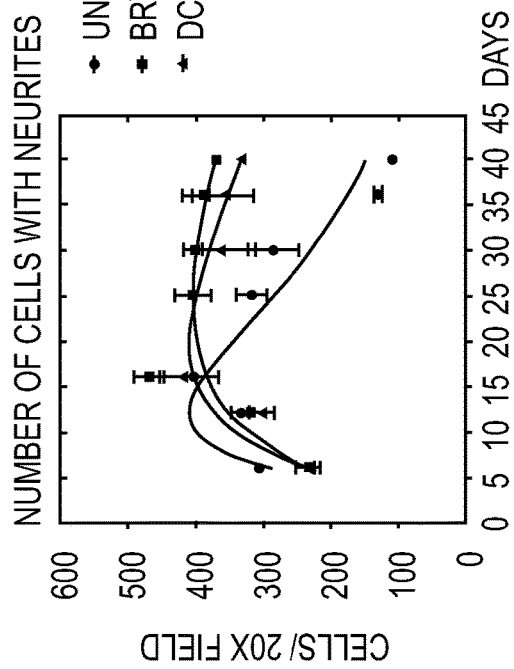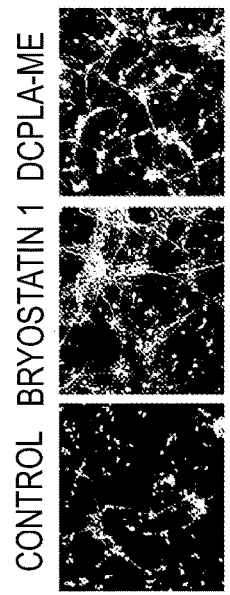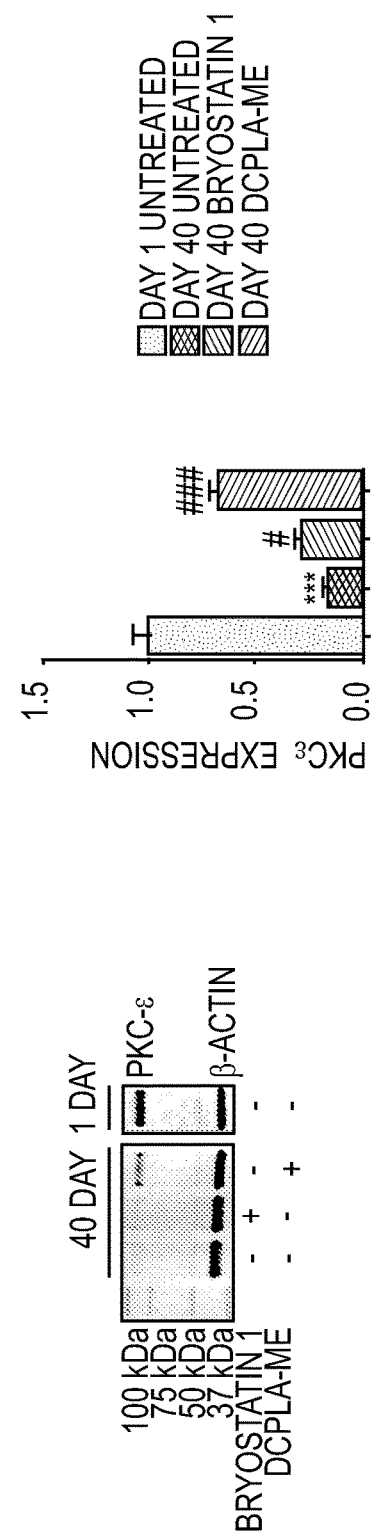
FIG. 15A  FIG. 15B  FIG. 15C  FIG. 15D

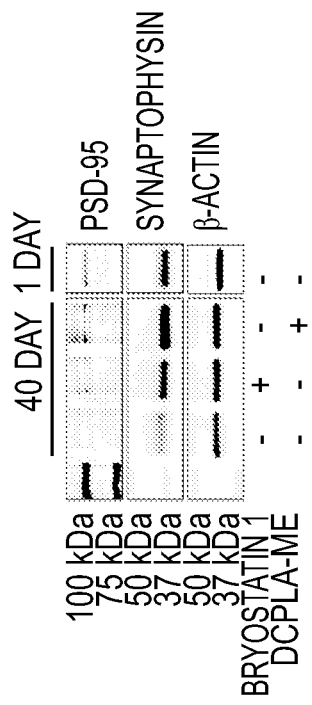
*FIG. 15E*
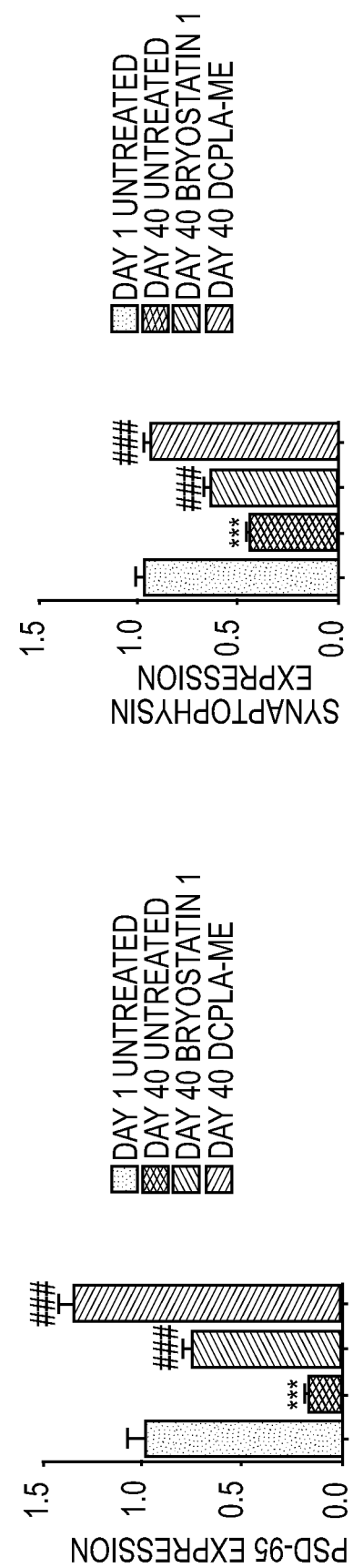
*FIG. 15G*
*FIG. 15F*

0.27nM BYROSTATIN TREATMENT

PKC ACTIVATORS AND COMBINATIONS THEREOF

This application claims priority to U.S. Provisional Patent Application No. 61/559,141 filed Nov. 13, 2011, the contents of which are herein incorporated by reference.

FIELD OF THE DISCLOSURE

The present disclosure relates to PKC activators and combinations thereof. The disclosure further relates to compositions, kits, and methods of treatment using the PKC activators and combinations thereof.

BACKGROUND OF THE DISCLOSURE

Protein kinase C is one of the largest families of protein kinase enzymes and is composed of a variety of isoforms. Conventional isoforms include α, βI, βII, γ; novel isoforms include δ, ε, η, θ; and atypical isoforms include ξ, and ι/λ.

PKC enzymes are primarily cytosolic but translocate to the membrane when activated. In the cytoplasm, PKC is phosphorylated by other kinases or autophosphorylates. In order to be activated, some PKC isoforms (e.g., PKC-ε) require a molecule to bind to the diacylglycerol ("DAG") binding site or the phosphatidylserine ("PS") binding site. Others are able to be activated without any secondary binding messengers at all.

PKC activators that bind to the DAG site include, but are not limited to, bryostatin, picologues, phorbol esters, aplysiatoxin, and gnidimacrin. PKC activators that bind to the PS site include, but are not limited to, polyunsaturated fatty acids and their derivatives.

Once activated and translocated, PKC is anchored into the membrane by the anchoring protein RACK1. See, e.g., Mochly-Rosen et al. (1991) *Proc Natl Acad Sci USA* 88, 3997-4000; Nishizuka, Y. (1995) *FASEB J* 9, 484-496; Sklan et al. (2006) *Prog Neurobiol* 78, 117-134. RACK1 localizes PKC to its corresponding substrates for phosphorylation, thus making PKC functionally active and physiologically relevant.

Activated PKC participates in a variety of biological pathways. For example, PKC activates ELAV mRNA-stabilizing proteins and c-CAMP-response-element-binding ("CREB") proteins. PKC isoforms also play a regulatory role in amyloid precursor protein ("APP") processing and amyloid accumulation. For examples, PKC-α and PKC-ε regulate APP processing by the non-amyloidogenic pathway, suggesting that decreases in these enzymes may lead to increases in A-beta synthesis and accumulation. Thus, PKC activators may be able to reduce levels of soluble A-beta and increase levels of soluble APP-α. PKC activators may also be able to reduce or eliminate amyloid plaques and neurofibrillary tangles.

PKC activators have been associated with prevention and treatment of various diseases and conditions. For example, PKC activators may allow for prevention and treatment of neurodegenerative diseases and conditions, neuroaffective diseases and disorders, cognitive impairments, and diseases and conditions associated with neuronal or synaptic loss. Indeed, PKC activators have been found to induce synapse formation. Moreover, PKC activators have been associated with improvement in, for example, memory and learning, including long-term memory.

In one specific example, PKC activators have demonstrated neuroprotective activity in animal models of Alzheimer's Disease ("AD"). See Etcheberrigaray et al., *Proc. Nat. Acad. Sci. USA*, 1992, 89: 7184-7188. AD is a neurodegenerative disorder that is characterized clinically by progressive decline of memory, cognition, reasoning, judgment, and emotional stability that gradually leads to profound mental deterioration and ultimately, death.

Pathologically, AD is associated with the accumulation of aggregated β-amyloid ("Aβ"), a 4 kDa peptide produced by the proteolytic cleavage of amyloid precursor protein ("APP") by γ- and γ-secretases. As disclosed herein, oligomers of Aβ are considered to be most toxic while fibrillar Aβ is largely inert. Interestingly, monomeric Aβ is found in normal patients and has an as-yet undetermined function.

PKC activators can reduce the levels of Aβ and prolong survival of AD transgenic mice. See Etcheberrigaray et al., 1992, *Proc. Nat. Acad. Sci. USA*, 89: 7184-7188. PKC-ε was shown to be most effective at suppressing Aβ production. See Zhu et al., *Biochem. Biophys. Res. Commun.*, 2001, 285: 997-1006. Accordingly, isoform-specific PKC activators are highly desirable as potential anti-AD drugs and other conditions associated with Aβ production.

The earliest consistent cytopathological change in AD is loss of synapses. See Scheff et al., *Neurobiol. Aging*, 2006, 27: 1372-1384; and Marcello et al., *Eur. J. Pharmacol.* 2008, 585: 109-118. In fact, synaptic loss appears to be the only pathological finding in the brain that is closely correlated with the degree of dementia in AD patients. See Terry et al., *Ann. Neurol.*, 1991, 30: 572-580. To that end, evidence suggests that Aβ is involved in synaptic loss.

PKC activators may also be used to treat and prevent other diseases and conditions associated with synaptic loss and/or Aβ. Persons who have suffered a brain injury, for example, show increased synthesis and expression of APP and its proteolytic product Aβ. See, e.g., Zohar et al., *Neurobiology of Disease*, 2011, 41: 329-337; Roberts et al., *Lancet*, 1991, 1422-1423; Gentleman e al., *Neuro Report*, 1997, 8: 1519-1522; Iwata et al., *J. Neuropathol. Exp. Neurol.*, 2002, 61: 1056-1068. In animal models, the PKC activator Bryostatin-1 was shown to protect against traumatic brain injury-induced learning and memory deficits. See Zohar et al., *Neurobiology of Disease*, 2011, 41: 329-337. Thus, PKC activators may be able to enhance memory and other cognitive functions.

Additionally, some forms of stroke are caused by Aβ, such as those associated with cerebral amyloid angiopathy ("CAA"). See U.S. Patent Application Publication No. 2010/0022645 A1. This disorder is a form of angiopathy in which the same Aβ deposits as found in AD accumulate in the walls of the leptomeninges and superficial cerebral cortical blood vessels of the brain. Amyloid deposition predisposes these blood vessels to failure, increasing the risk of a hemorrhagic stroke. CAA is also associated with transient ischemic attacks, subarachnoid hemorrhage, Down's syndrome, post irradiation necrosis, multiple sclerosis, leucoencephalopathy, spongiform encephalopathy, and dementia pugilistica.

Both PKC-α and PKC-ε are important for synaptogenesis—i.e., the formation of synapses. The high abundance of PKC-ε in presynaptic nerve fibers suggests a role in neurite outgrowth, synaptic formation, and neurotransmitter release. See Shirai et al., *FEBS*, 2008, 29: 1445-1453. Nontoxic drugs activating PKC-α and PKC-ε can promote synaptogensis under non-pathological conditions and actually prevent synaptic loss under pathological conditions. See Nelson et al., *Trends Biochem. Sci.*, 2009, 34: 136-145; Hongpaisan et al., *Proc. Natl. Acad. Sci. USA*, 2007, 104: 19571-19576;

Sun et al., *Proc. Natl. Acad. Sci. USA,* 2008, 105: 13620-13625; Sun et al., *Proc. Natl. Acad. Sci. USA,* 2009, 106: 14676-14680

For example, PKC activators have demonstrated neuroprotective activity in animal models of stroke. See Sun et al., *Eur. J. Pharmacol.,* 2005, 512: 43-51. Several PKC isoforms play a central role in mediating ischemic and reperfusion damage following stroke. Studies with experimental stroke models, mouse genetics, and selective peptide inhibitors and activators have demonstrated that PKC-ε is involved in induction of ischemic tolerance and prevents damage, while PKC-δ and PKC-γ are implicated in injury. See Takayoshi et al., *Stroke,* 2007, 38(2): 375-380; and Bright et al., *Stroke,* 2005; 36: 2781. Postischemic/hypoxic treatment with Bryostatin-1 effectively rescued ischemia-induced deficits in synaptogenesis, neurotrophic activity, and spatial learning and memory. See Sun et al., *Proc. Natl. Acad. Sci. USA.,* 2008, 105(36): 13620-13625.

PKC activation has a crucial role in learning and memory enhancement and PKC activators have been shown to increase memory and learning. See Sun et al., *Eur. J. Pharmacol.* 2005, 512: 43-51; Alkon et al., *Proc. Natl. Acad. Sci. USA.,* 2005, 102: 16432-16437. For example, bryostatin increased the rate of learning in rodents, rabbits, and invertebrates. See Sun et al., *Eur. J. Pharmacol.,* 2005, 512: 43-51; Wang et al., *Behav. Pharmacol.,* 2008, 19: 245-256; and Kuzirian et al., *Biol. Bull.,* 2006, 210: 201-214. Additionally, bryostatin-induced synaptogenesis for long-term associative memory was shown to be regulated by PKC activation. Hongpaisan et al., *Proc. Natl. Acad. Sci. USA,* 2007, 104: 19571-19576.

PKC activation has been associated with a variety of other conditions. For example, PKC activators have demonstrated neuroprotective activity in animal models of depression. See Sun et al., *Eur. J. Pharmacol.,* 2005, 512: 43-51.

SUMMARY OF THE DISCLOSURE

The present disclosure relates to PKC activators and combinations thereof. In one embodiment, the PKC activator is chosen from cyclopropanated polyunsaturated fatty acids, cyclopropanated monounsaturated fatty acids, cyclopropanated polyunsaturated fatty alcohols, cyclopropanated monounsaturated fatty alcohols, cyclopropanated polyunsaturated fatty acid esters, cyclopropanated monounsaturated fatty acid esters, cyclopropanated polyunsaturated fatty acid sulfates, cyclopropanated monounsaturated fatty acid sulfates, cyclopropanated polyunsaturated fatty acid phosphates, cyclopropanated monounsaturated fatty acid phosphates, macrocyclic lactones, DAG derivatives, isoprenoids, octylindolactam V, gnidimacrin, iripallidal, ingenol, napthalenesulfonamides, diacylglycerol kinase inhibitors, fibroblast growth factor 18 (FGF-18), insulin growth factor, hormones, growth factor activators, cyclopropanated polyunsaturated fatty acid conjugates, cyclopropanated monounsaturated fatty acid conjugates, bryostatin conjugates, bryolog conjugates, and retinoic acid conjugates.

The present disclosure further relates to combinations of at least the PKC activators above. These combinations can be mixtures, conjugates, and use combinations. In at least one embodiment, the combination comprises at least one PKC activator and at least one other PKC activator. In another embodiment, the combination comprises at least one PKC activator and at least one other agent, such as a retinoid or a cholesterol.

Moreover, the present disclosure relates to methods for treating neurodegenerative disorders or conditions such as Alzheimer's disease and Parkinson's disease; neuroaffective disorders such as depression, bipolar disorder, and schizophrenia; mental retardation; stroke; brain injury including traumatic brain injury and brain injury induced by irradiation, said methods comprising administering at least one PKC activator or a combination thereof to a patient in need thereof. The present disclosure further relates to methods for improving learning and/or memory comprising administering at least one PKC activator or a combination thereof to a patient in need thereof.

The present disclosure also relates to methods for screening at least one drug comprising: adding at least one retinoid and at least one PKC activator to cells; allowing a synaptic network to form; adding at least one toxin that disrupts synaptic networks; adding the at least one drug to be screened; and determining whether the synaptic network has been at least partially restored or whether any synaptogenesis has occurred. In one embodiment, the screening is used to determine whether the drug is able to at least partially restore synaptic networks, is able to induce synaptogenesis, and/or is able to prevent the destruction of synaptic networks.

BRIEF DESCRIPTION OF THE DRAWINGS

FIG. 9: ASPD induced synaptic loss. Confocal images of rat hippocampal primary neurons are shown in FIG. 9A. The fourth column is the image of the first three columns merged. Mean fluorescence intensity was calculated and was expressed as percentage of control (n=6). Graphical representations of expression level of PSD-95 (FIG. 9B) and synaptophysin (FIG. 9C) are shown. Values are represented as mean±SEM. (Student's t test *. p<0.05; and **, p<0.005).

A graphical representation of MAP-2, PSD-95, and synaptophysin expression is shown in FIG. 10B.

FIG. 15: PKC-ε activation prevents degeneration of human primary neurons. Primary human neurons were treated with either DCPLA-ME (100 nM) or bryostatin 1 (0.27 nM) for 40 days. Fresh drug was added every third day with 50% media change. FIG. 15A—Image of 40 day old untreated ("control"), bryostatin 1, and DCPLA-ME treated neurons. FIG. 15B—Number of neurite positive cells counted from three 20× fields (508 μm$^2$) over time. DCPLA-ME and bryostatin 1 treatment stabilized cellular viability for at least 40 days. Viability of untreated cells declined after 20 days. FIG. 15C, FIG. 15D—Immunoblot analysis of PKCε in 40 day old neurons compared to 1 day neurons. DCPLA-ME protects PKC-ε. FIG. 15E—Immunoblot analysis of PSD-95 and synaptophysin after 40 day bryostatin or DCPLA-ME treatment. FIG. 15F, FIG. 15G—Immunostaining of PSD-95 and synaptophysin calculated from Western blots. Staining is significantly higher in DCPLA-ME and bryostatin 1 treated cells.

Bry") at 72 hr. The first column is the nucleus stained with DAPI, the second column is PSD-95, the third column is synaptophysin, and the last is the merged image of the first three.

Figure 20:
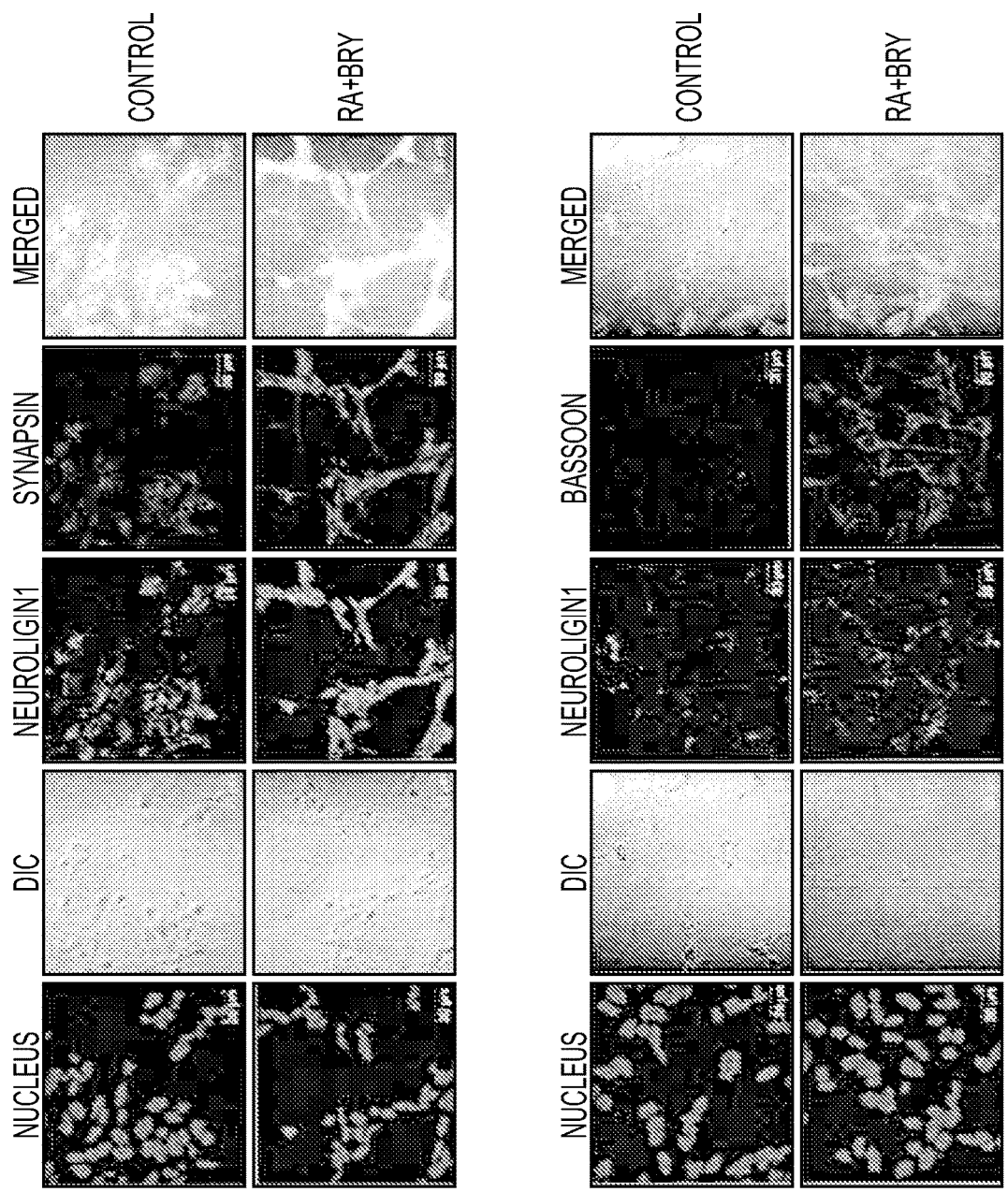

FIG. 20: Confocal images of untreated cells ("Control") and cells treated with RA and Bryostatin-1 ("RA+Bry") at 72 hr. The first column is the nucleus stained with DAPI, the second column is differential interference contrast, the third column is neuroligin-1, the fourth column is synapsin or bassoon, and the last is the merged image of the four prior images.

Figure 21:
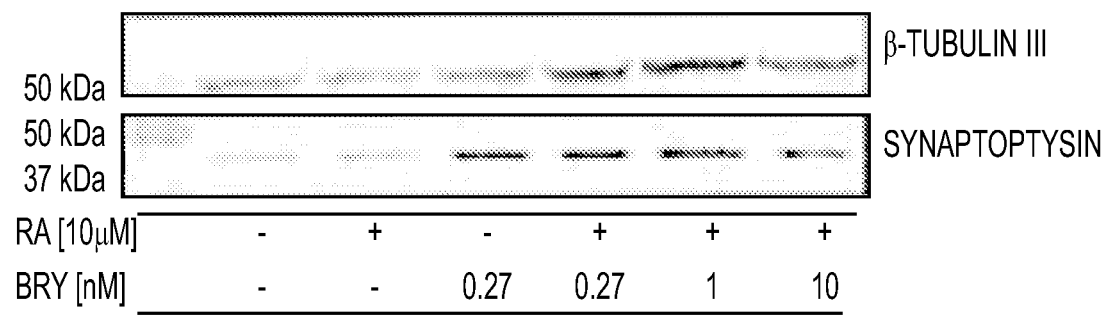
Figure 21:
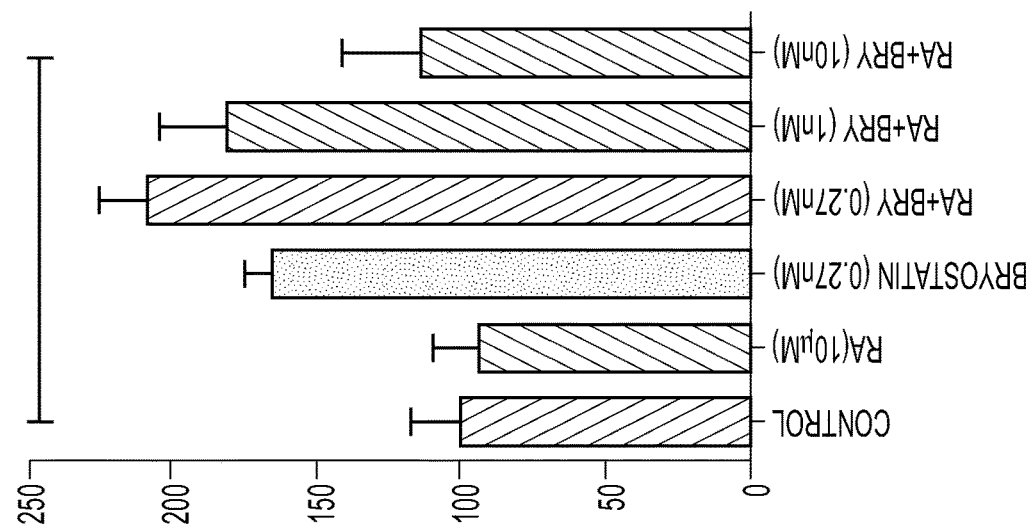
Figure 21:
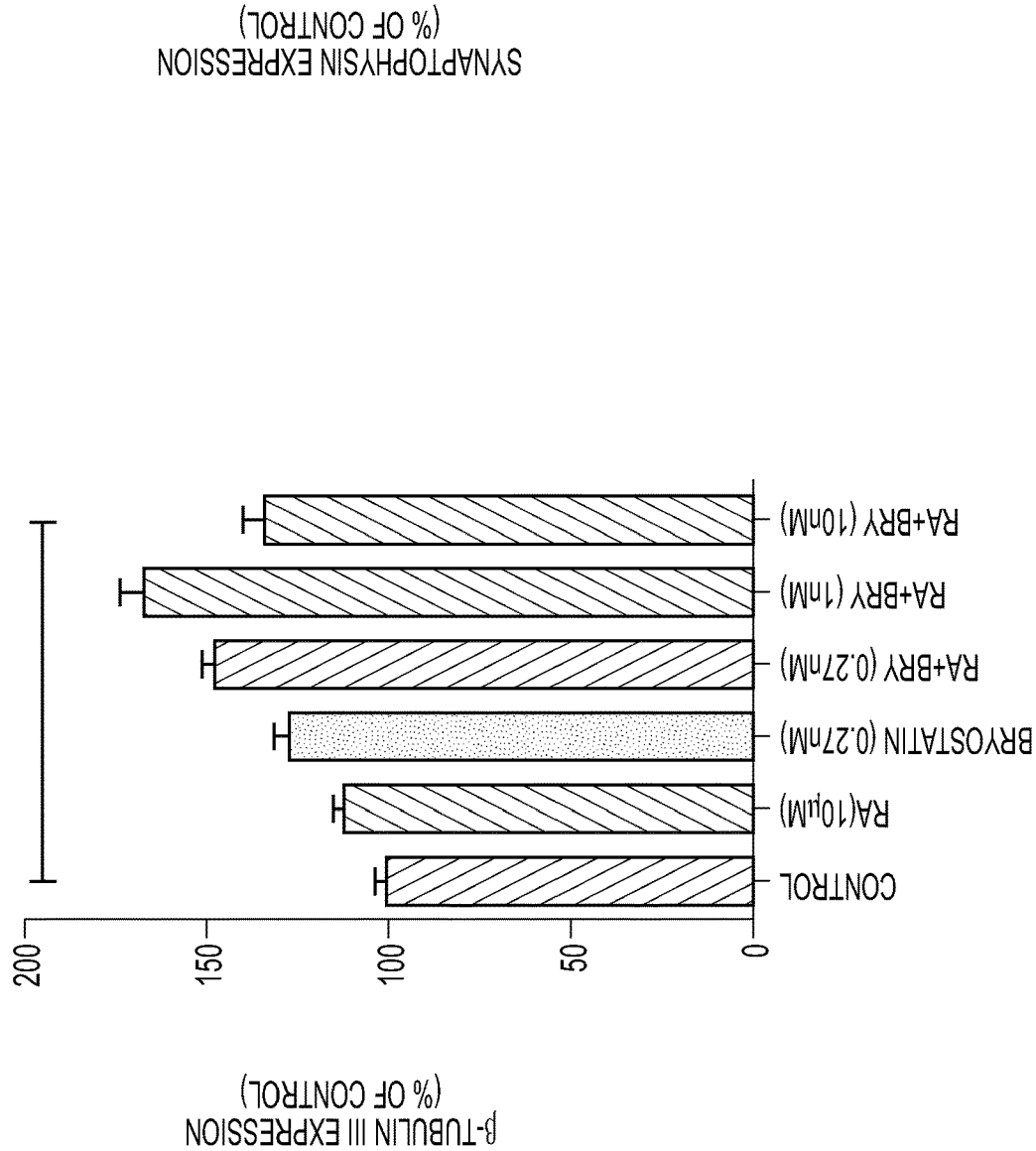

FIG. 21: Immunoblot analysis (and graphical representation) of β-tubulin III and synaptophysin levels in untreated cells, RA-treated cells, cells treated with Bryostatin-1 (0.27 nM), cells treated with RA and Bryostatin-1 (0.27 nM), cells treated with RA and Bryostatin-1 (1 nM), and cells treated with RA and Bryostatin-1 (10 nM) at 72 hr. Data are represented as the mean±SE of three independent experiments (* represents $p<0.05$,  represents $p<0.005$, and * represents $p<0.0005$).

Figure 22A:
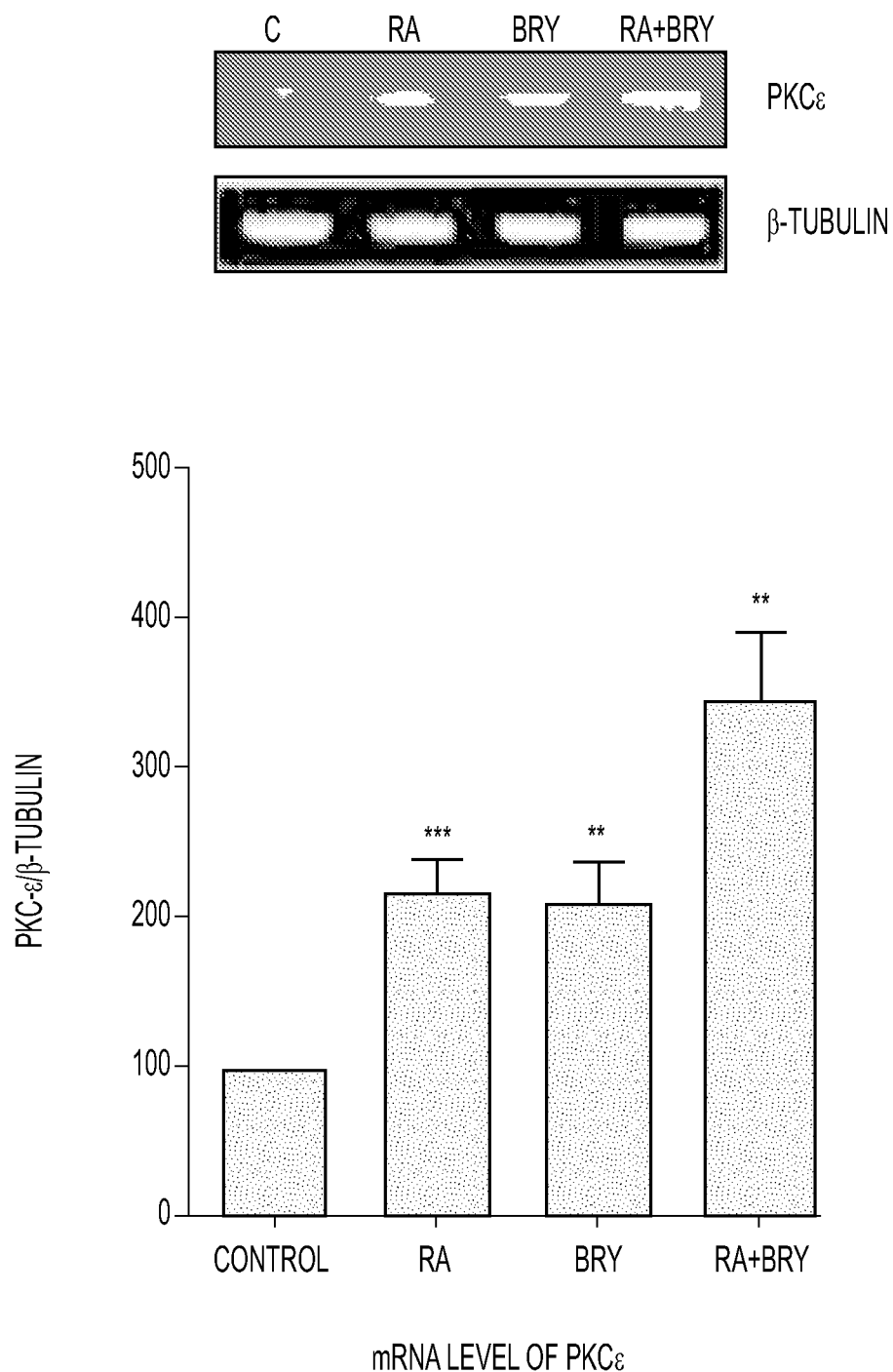

FIG. 22A: Transcript level of PKC-ε in untreated cells ("C"), RA-treated cells, Bryostatin-1-treated cells ("Bry"), and cells treated with RA and Bryostatin-1 ("RA+Bry"). Values in the graph are represented as the percentage increase in densitometric value of PKC-ε normalized to β-tubulin in the treated cells compared to untreated cells. Data are represented as mean±SE of three independent experiments (* represents $p<0.05$, ** represents $p<0.005$, and represents $p<0.0005$).

Figure 22B:
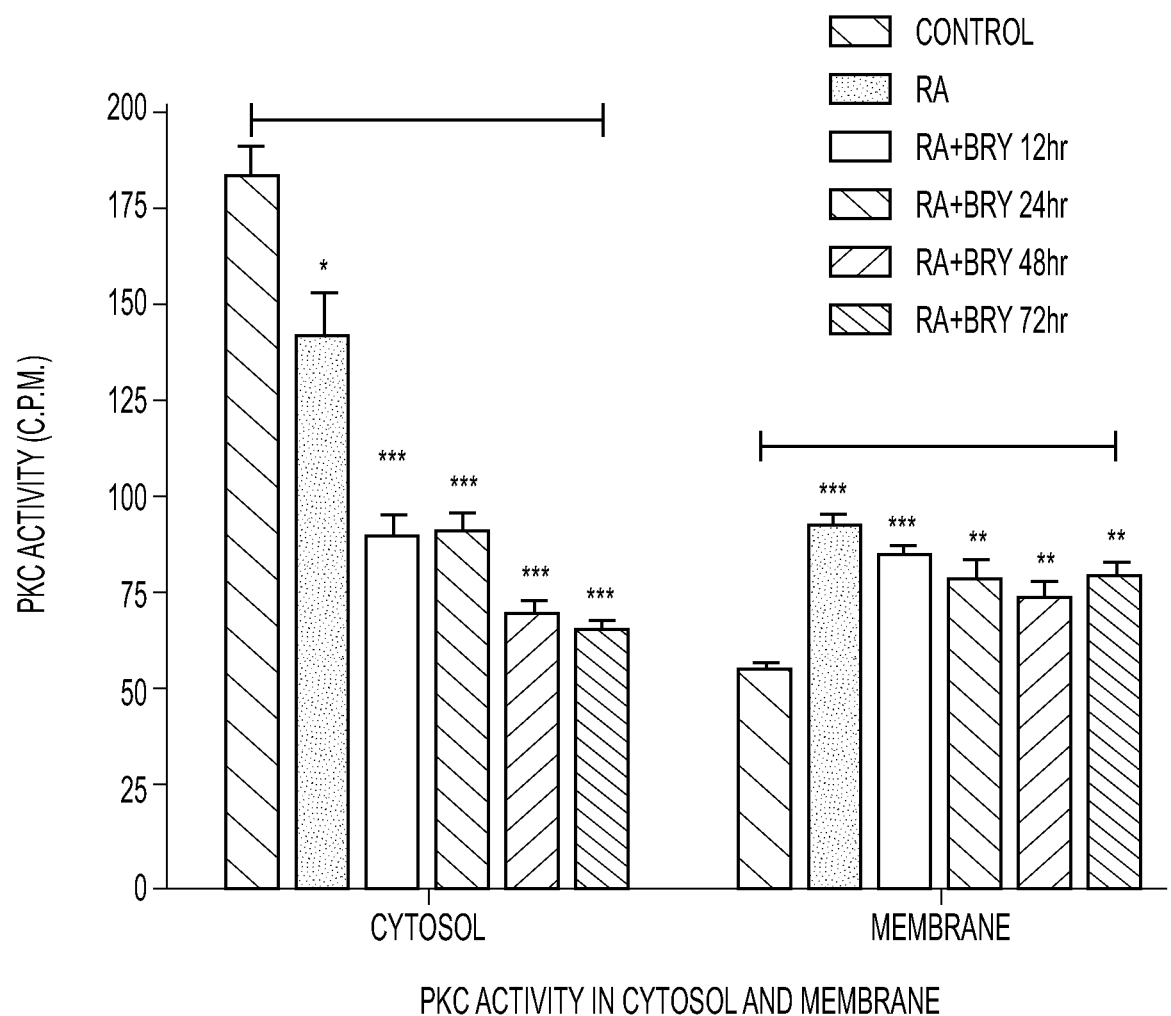

FIG. 22B: Total PKC activity in cytosol and membrane of untreated cells ("control"), RA-treated cells at 12 hr, and cells treated at RA and Bryostatin-1. The cells treated at RA and Bryostatin-1 were measured at 12 hr, 24 hr, 48 hr, and 72 hr. Data are represented as the mean±SE of CPM from three independent experiments. (* represents $p<0.05$,  represents $p<0.005$, and * represents $p<0.0005$).

Figure 22C:
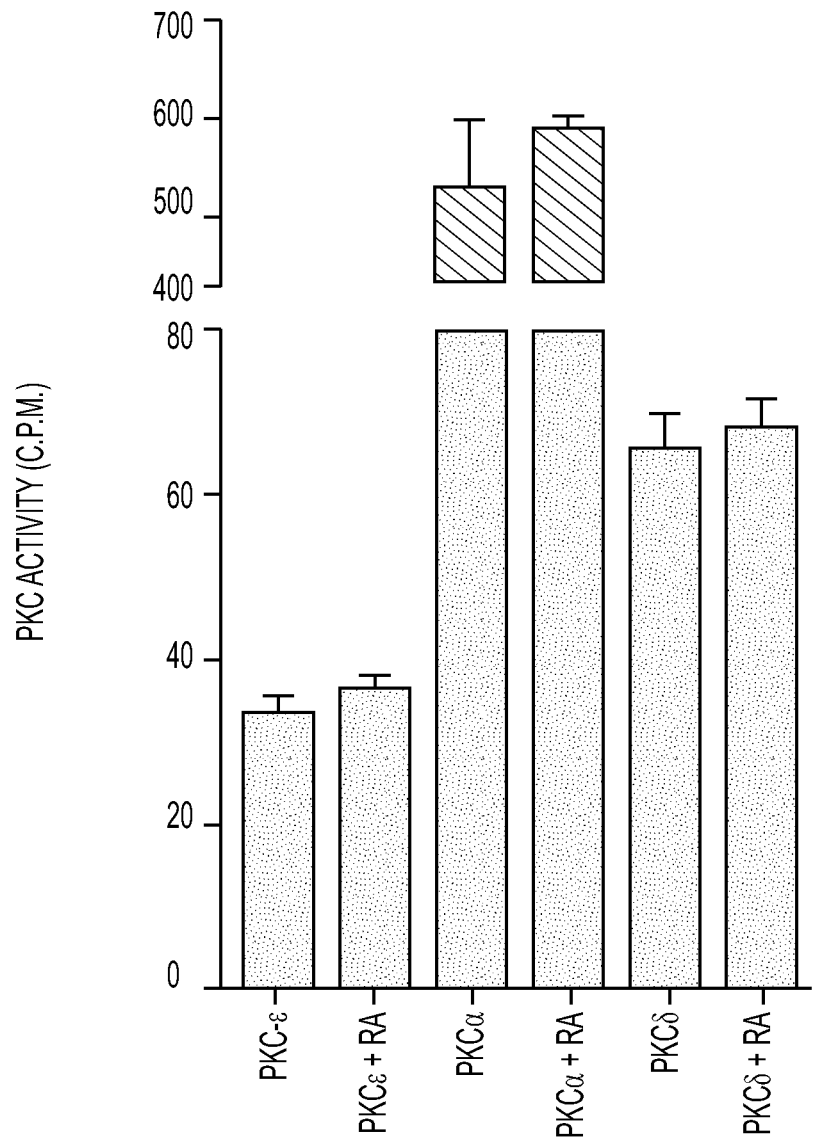

FIG. 22C: Activation of PKC-ε, PKC-α and PKC-δ by RA. Data in the figure represents mean±SE of CPM from three independent experiments.

Figure 22D:
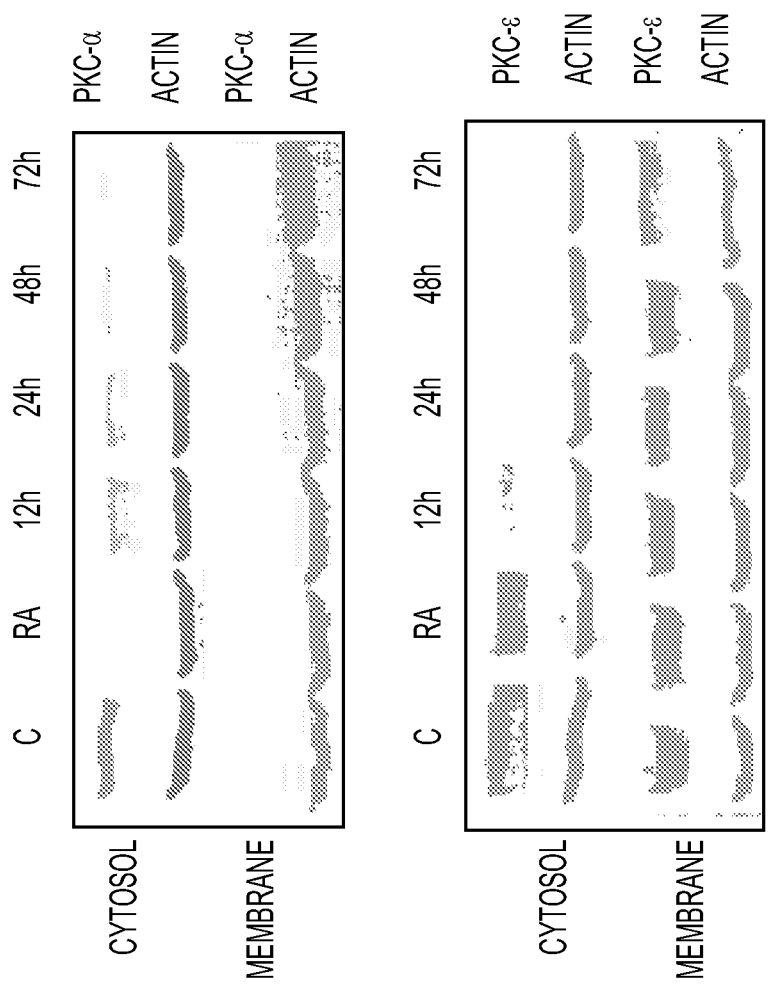
Figure 22D:
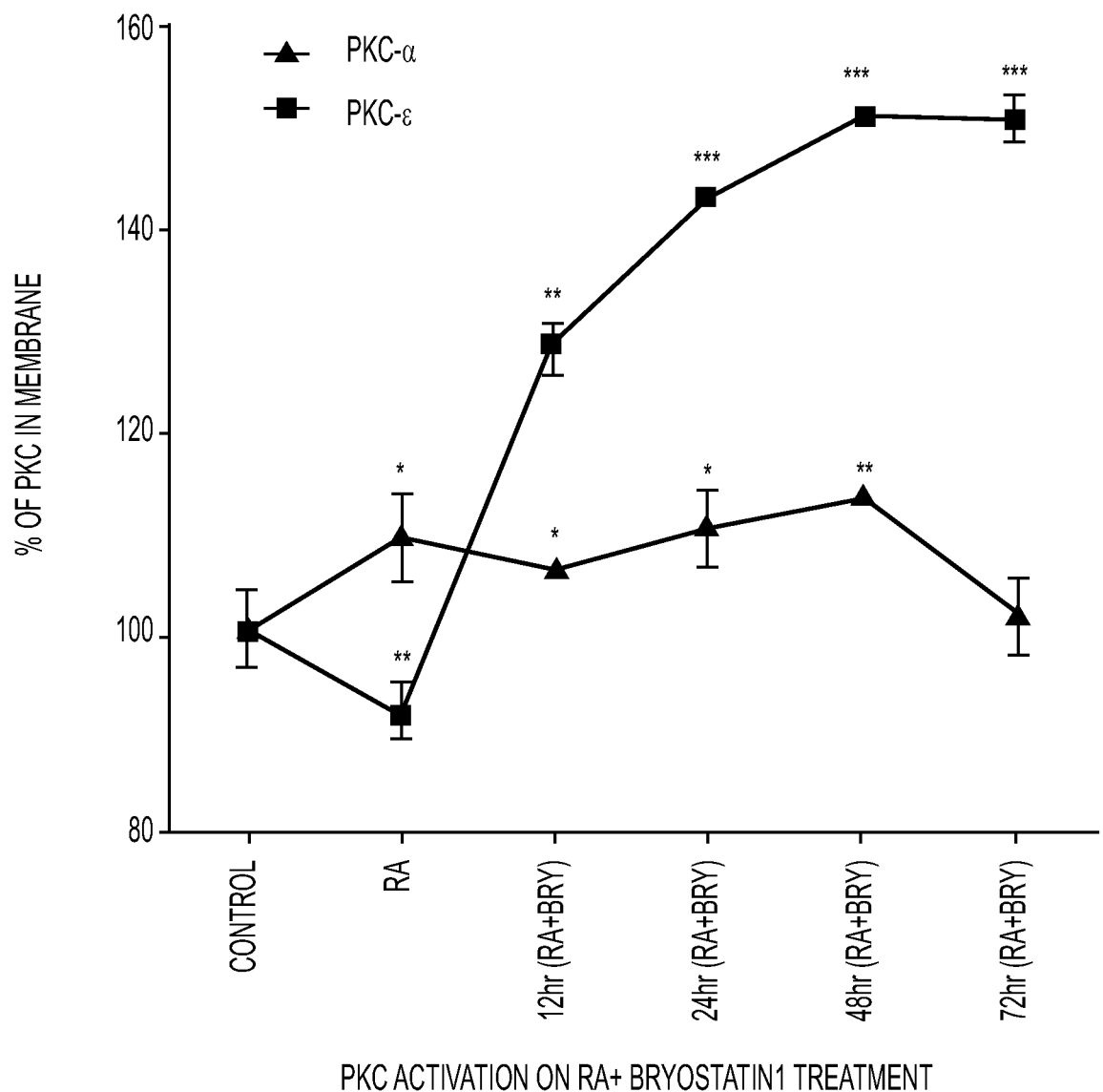

FIG. 22D: Western blot analysis of PKC-ε and PKC-α in the cytosol and membrane of untreated cells ("control"), RA-treated cells at 12 hr, and cells treated with RA and Bryostatin-1 ("RA+Bry"). The cells treated at RA and Bryostatin-1 were measured at 12 hr, 24 hr, 48 hr, and 72 hr. Activation of PKC was calculated as percentage of total PKC in the membrane (Membrane/Cytosol+Membrane). Data are represented as the mean±SE of three independent experiments (* represents $p<0.05$,  represents $p<0.005$ and * represents $p<0.0005$).

Figures 23A, 23B, 23C:
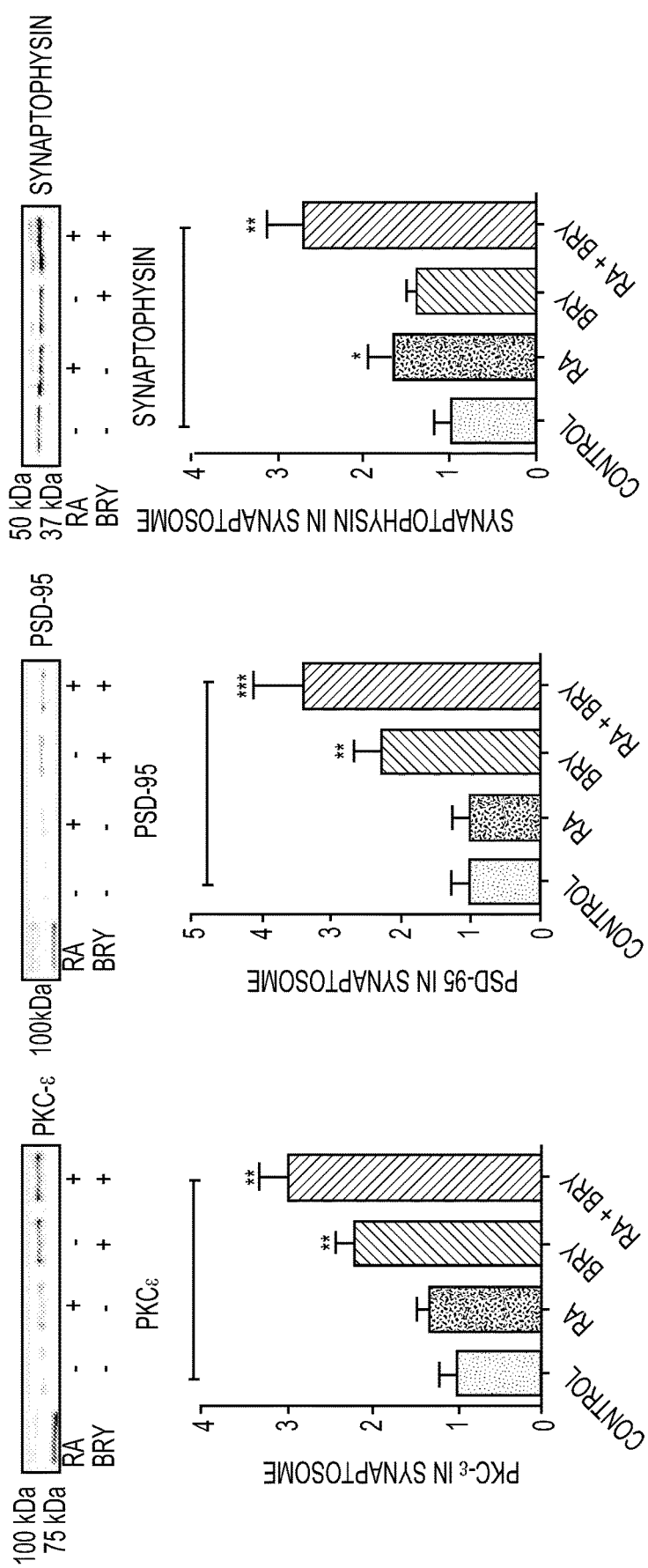

FIG. 23A: Western blot analysis of PKC-ε level in synaptosomes prepared from untreated cells ("Control"), RA-treated cells, Bryostatin-1-treated cells, and cells treated with RA and Bryostatin-1 ("RA+Bry"). Data in the figure represents mean±SE of three independent experiments (* represents $p<0.05$, ** represents $p<0.005$).

FIG. 23B: Western blot analysis of PSD-95 level in synaptosomes prepared from untreated cells ("Control"), RA-treated cells, Bryostatin-1-treated cells, and cells treated with RA and Bryostatin-1 ("RA+Bry").

FIG. 23C: Western blot analysis of synaptophysin level in synaptosomes prepared from untreated cells ("Control"), RA-treated cells, Bryostatin-1-treated cells, and cells treated with RA and Bryostatin-1 ("RA+Bry"). Data in the figure represents mean±SE of three independent experiments (* represents $p<0.05$).

Example 24A: Confocal images of untreated rat hippocampal primary neurons ("Control"), neurons treated with ASPD, and neurons treated with ASPD, RA, and Bryostatin-1. The first column is the nucleus stained with DAPI, the second column is PSD-95, the third column is synaptophysin, and the last is the merged image of the first three.

Figure 24A:
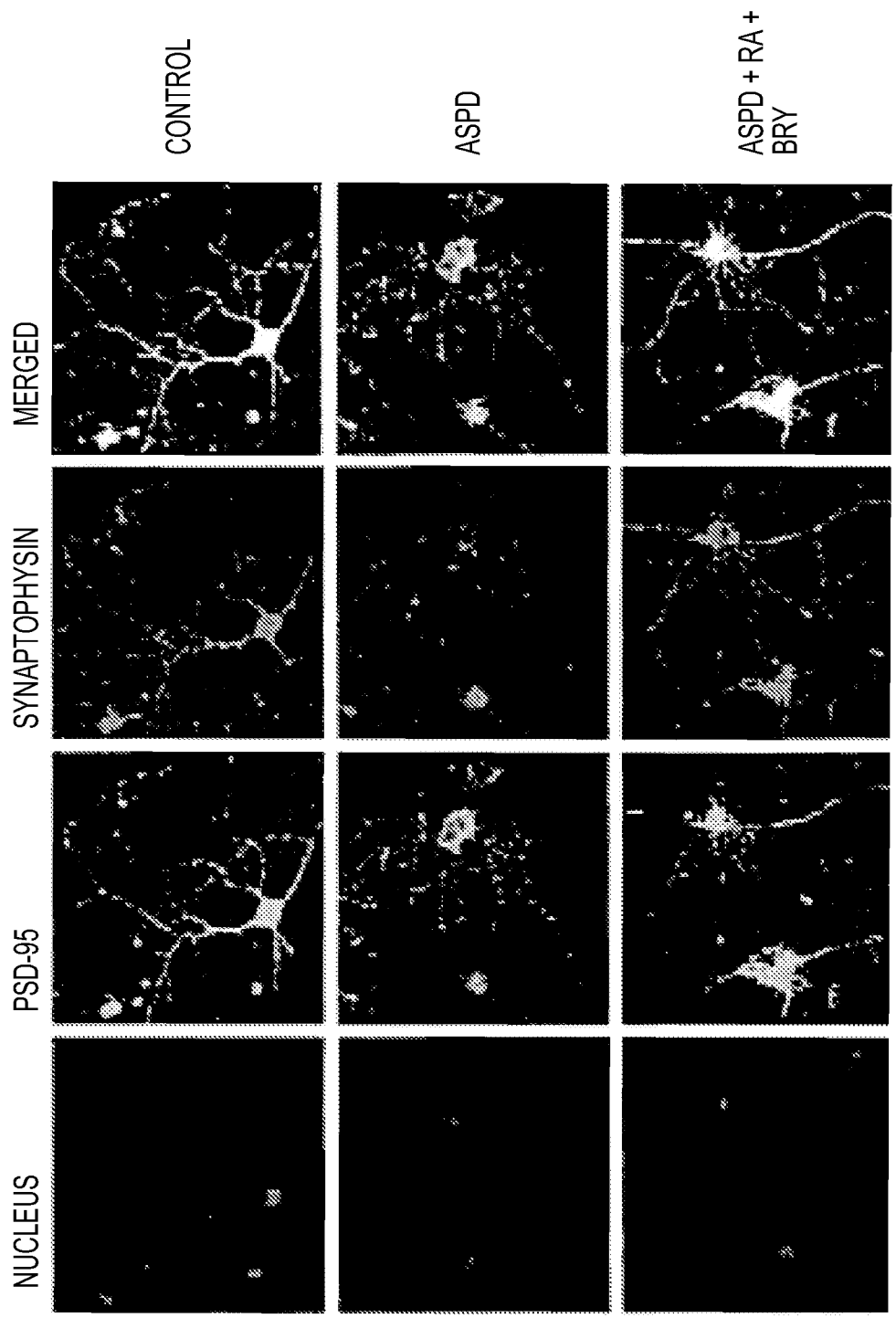
Figure 24C:
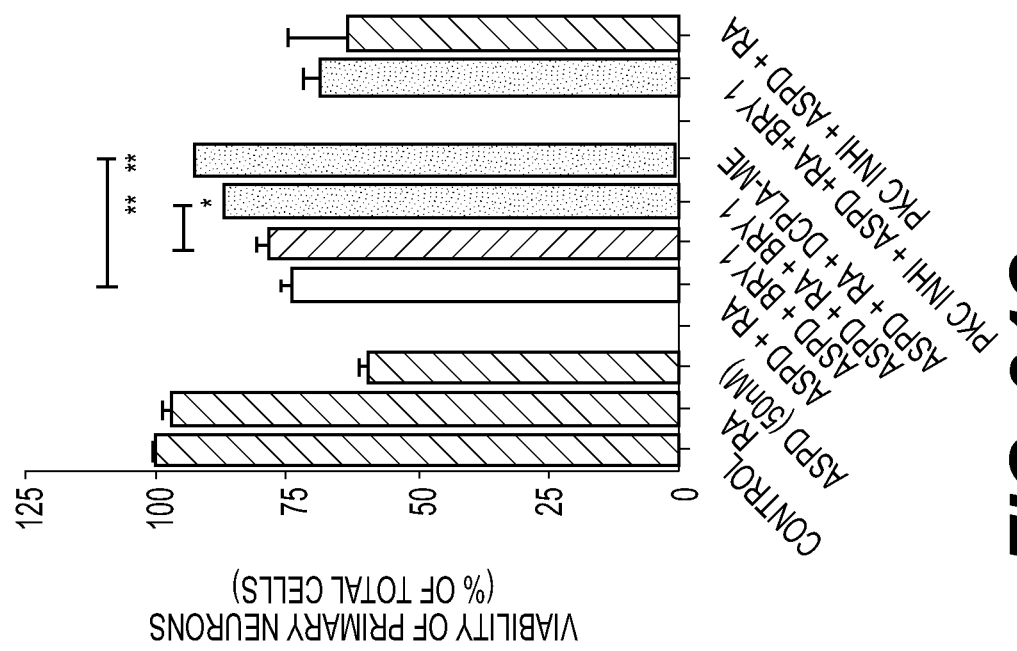
Figure 24B:
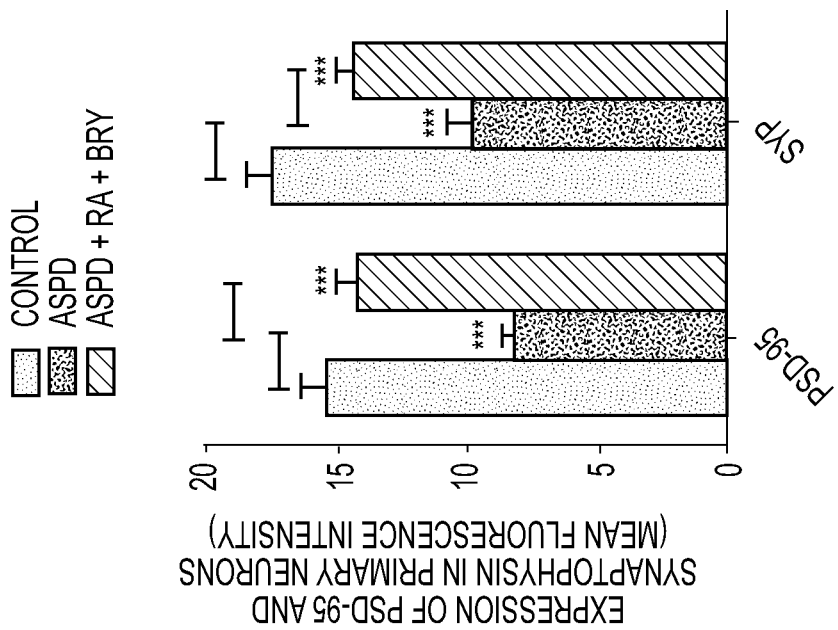

FIG. 24B: Mean fluorescence intensity of PSD-95 and synaptophysin in untreated cells, ASPD-treated cells, and cells treated with ASPD, RA, and Bryostatin-1 ("ASPD+RA+Bry") was measured.

FIG. 24C: Viability of rat hippocampal primary neurons treated with vehicle; RA; ASPDs; ASPD and RA; ASPD and Bryostatin-1; ASPDs, RA, and Bryostatin-1; ASPDs, RA, and DCPLA-ME; PKC-inhibitor [EAVSLKPT], ASPDs, RA, and Bryostatin-1; and PKC-inhibitor [EAVSLKPT], ASPDs, and RA. All studies used 50 nM ASPDs. The viability of the cells were measured after 24 hr by the MTT assay.

Figure 25:
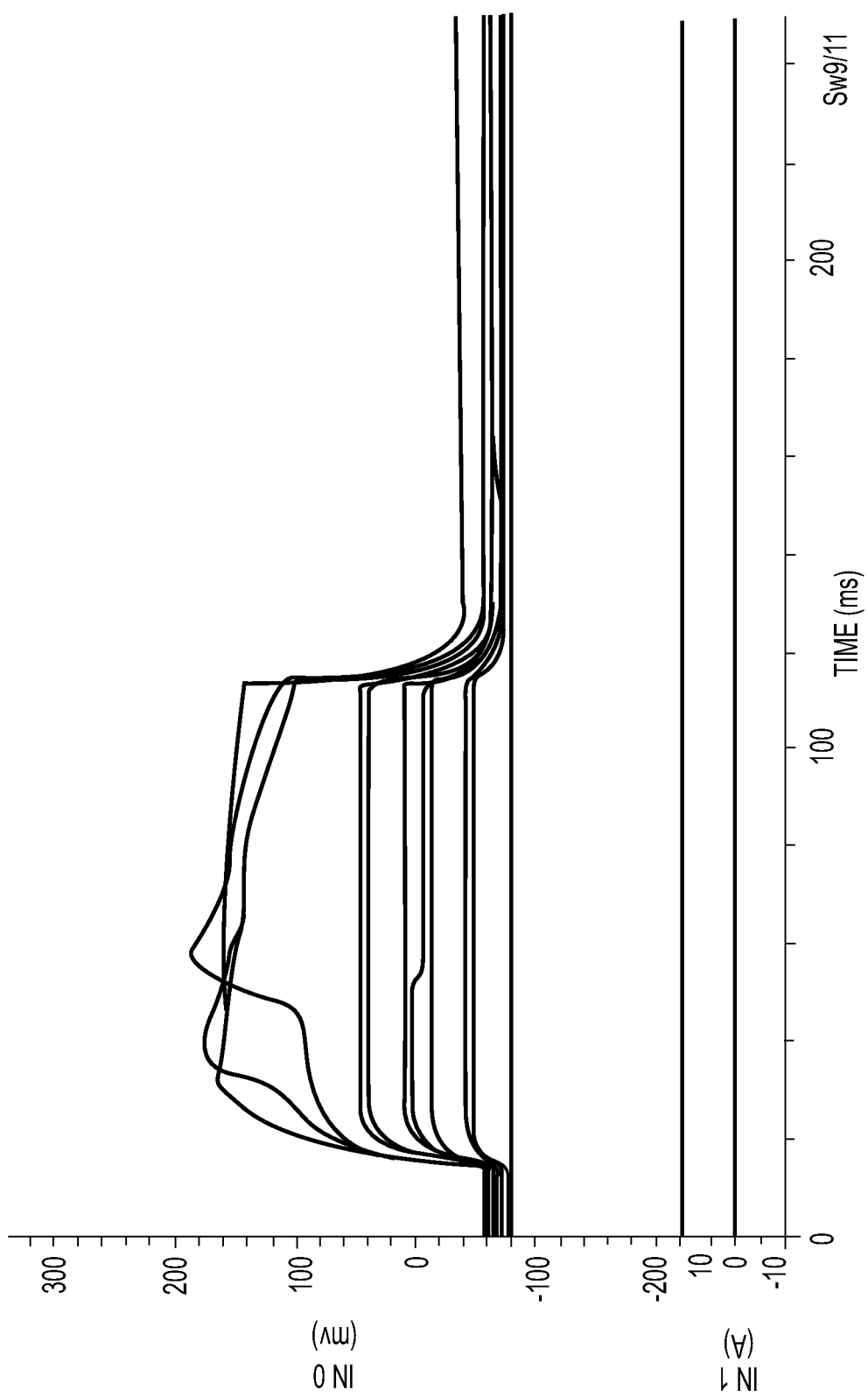

FIG. 25: Current clamp of SH-SY5Y Cells differentiated with RA and Bryostatin-1.

FIG. 26: PKC-ε is required for differentiation of SH-SY5Y cells. PKC-ε knockdown prevents RA+bryostatin 1 induced neuronal differentiation. FIG. 26A—PKC-ε knockdown by siRNA (PKCε knockout ("KO") cells) reduced PKC-ε expression by 50%. PKC-ε overexpressing ("OE") cells increased PKC-ε expression by >2-fold. FIG. 26B—Immunoblot analysis of synaptophysin in PKC-ε knockout cells. Synaptophysin immunostaining decreased in PKC-ε KO cells and RA+bryostatin 1 treatment failed to increase the expression. FIG. 26C—Synaptophysin expression in PKC-ε overexpressing cells. FIG. 26D—Confocal images of control cells, RA+bryostatin 1 treated cells, and RA+bryostatin 1 treated PKCε knockout cells. RA+bryostatin have no effect in PKCε KO cells. FIGS. 26E and 26F—Graphical representation of PSD-95 and synaptophysin immunostaining in presence and absence of PKCε. Data are represented as the mean±SE of three independent experiments. * represents significance with respect to control (*$p<0.05$,  $p<0.005$ and * $p<0.0005$).

Figure 27A:
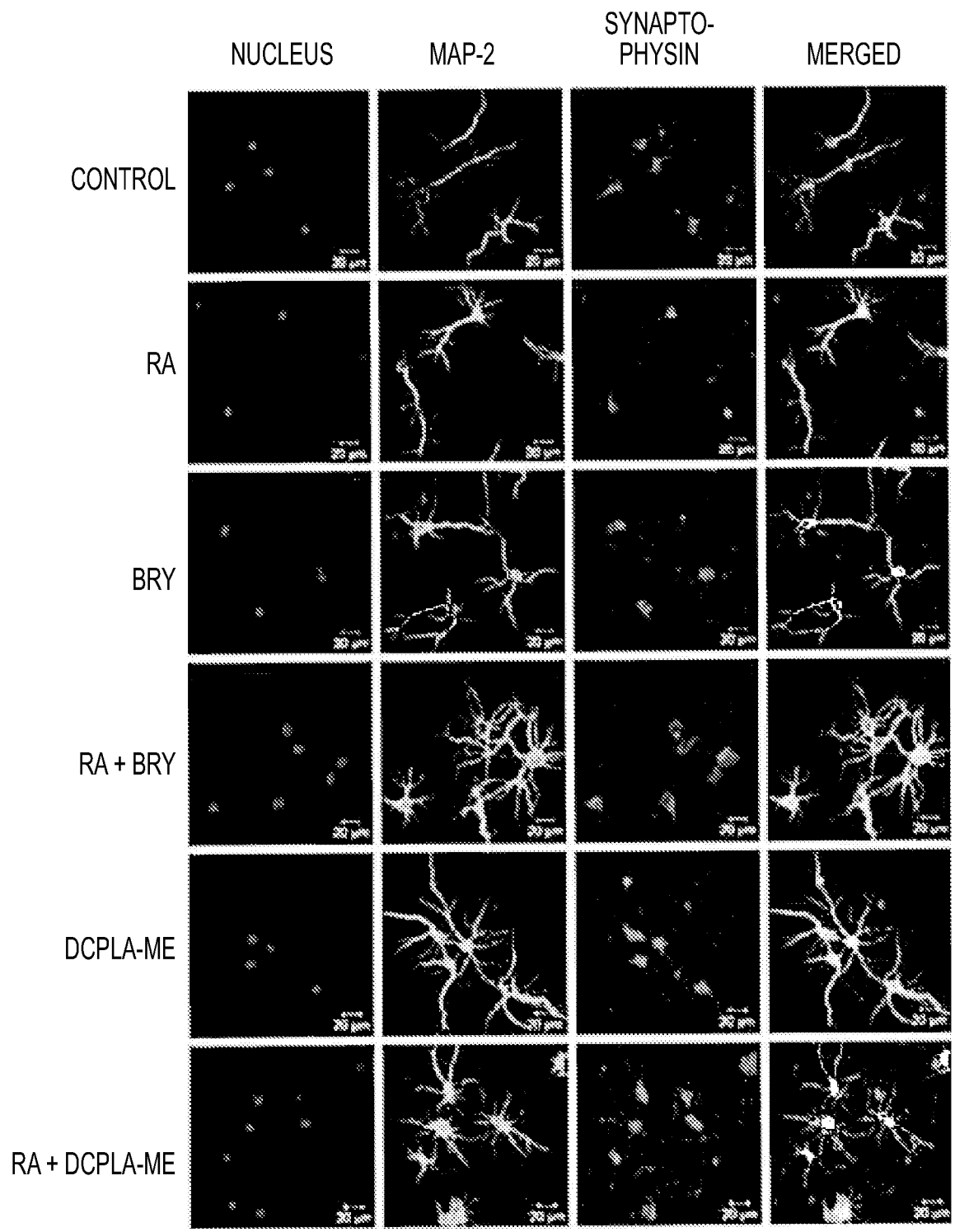
Figures 27B, 27C:
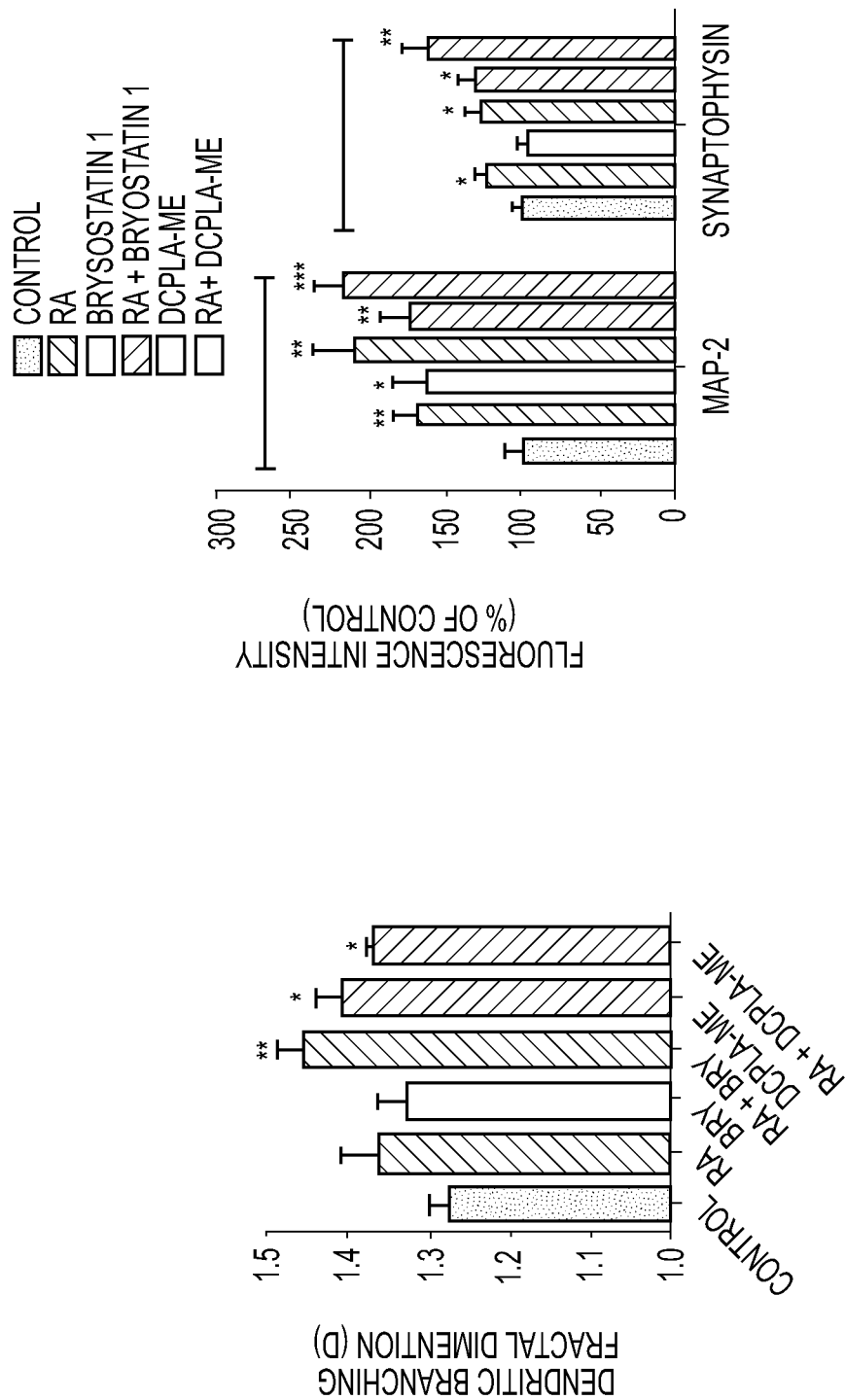

FIG. 27: PKC-ε specific activation induces maturation and differentiation in rat primary neurons. Seven day old culture of rat hippocampal neurons were treated with RA (10 μM), 0.27 nM bryostatin 1(Bry), RA+bryostatin 1(RA+Bry), DCPLA-ME (100 nM) or RA+DCPLA-ME for 48 h. FIG. 27A—Confocal micrographs showing rat hippocampal neurons stained for MAP-2 (green), synaptophysin (red), and DAPI (blue). FIG. 27B—Graphical representation of number of dendritic branches per neuron. PKCε activation by RA+bryostatin 1(RA+Bry), DCPLA-ME or RA+DCPLA-ME increase the dendritic branching by 2-fold. FIG. 27C—Mean fluorescence intensity for MAP-2 or synaptophysin calculated from eight random 225 μm2 of confocal images. Data are represented as mean±SE. * represents significance with respect to control (* $p<0.05$,  $p<0.005$ and * $p<0.0005$).

DEFINITIONS

As used herein, the singular forms "a," "an," and "the" include plural reference.

As used herein, "protein kinase C activator" or "PKC activator" refers to a substance that increases the rate of the reaction catalyzed by PKC. PKC activators can be non-specific or specific activators. A specific activator activates one PKC isoform, e.g., PKC-ε, to a greater detectable extent than another PKC isoform.

As used herein, the term "fatty acid" refers to a compound composed of a hydrocarbon chain and ending in a free acid, an acid salt, or an ester. When not specified, the term "fatty acid" is meant to encompass all three forms. Those skilled in the art understand that certain expressions are interchangeable. For example, "methyl ester of linolenic acid" is the same as "linolenic acid methyl ester," which is the same as "linolenic acid in the methyl ester form."

As used herein, the terms "LDL," "LDLs," "LDL particle," and "LDL particles" refer to low-density lipoproteins with a lipid core. The composition and overall structure of LDL particles are known in the art. See e.g., Hevonoja et al., 2000, *Biochimica et Biophysica Acta*, 1488: 189-210. LDL particles can be isolated from natural sources (natural LDL) or prepared synthetically (artificial LDL). See, e.g., WO 2004/050062. The surfaces of natural LDL particles are associated with apolipoproteins that target LDL particles to specific receptors. Apolipoprotein E receptors are found in the liver and on endothelial cells on the blood-brain barrier.

As used here, "at least one LDL particle" indicates that the LDL particles need not be of the same composition or structure. For example, LDL particles associated with apolipoprotein B can be considered to at least have a different composition than LDL particles associated with apolipoprotein E.

As used herein, the term "cyclopropanated" or "CP" refers to a compound wherein at least one carbon-carbon double bond in the molecule has been replaced with a cyclopropane group. The cyclopropyl group may be in cis or trans configuration. Unless otherwise indicated, it should be understood that the cyclopropyl group is in the cis configuration. Compounds with multiple carbon-carbon double bonds have many cyclopropanated forms. For example, a polyunsaturated compound in which only one double bond has been cyclopropanated would be said to be in "CP1 form." Similarly, "CP6 form" indicates that six double bonds are cyclopropanated.

For example, docosahexaenoic acid ("DHA") methyl ester has six carbon-carbon double bonds and thus can have one to six cyclopropane rings. Shown below are the CP1 and CP6 forms. With respect to compounds that are not completely cyclopropanated (e.g. DHA-CP1), the cyclopropane group(s) can occur at any of the carbon-carbon double bonds.

DESCRIPTION OF THE EMBODIMENTS

The present disclosure relates to PKC activators and combinations thereof. The present disclosure further relates to compositions, kits, and methods of treatment using the PKC activators and combinations thereof.

The disclosure relates to the discovery that selective PKC activators, and/or combinations of at least one selective or non-selective PKC activator, can cause differentiation, extensive neurite outgrowth, formation of synapses, and even synaptic networks. This result is especially surprising because such results may occur even in an in vitro setting, such as a tissue culture plate. Under such harsh conditions, non-selective PKC activators are not known to create such networks. Similarly, other agents (e.g., retinoids) do not create such networks alone.

In addition, the use of selective PKC activators, and/or combinations of at least non-selective or selective PKC activator, may result in sustained PKC activation as compared to non-selective PKC activator(s) alone. The use of at least one selective PKC activator, or combinations of at least one non-selective or selective PKC activator, may also restore synapses and create synaptic networks in situations where synaptic loss has been caused by toxic agents such as amylospheriods ("ASPD"). Restoration of synapses and/or creation of synaptic networks may allow for faster recovery from disorders and conditions associated with synaptic loss. Creation of synaptic networks may also afford for the creation of an in vitro method for screening potential drugs.

Additionally, the selective PKC activators, or combinations of at least one non-selective or selective PKC activator, may achieve the same result as administration of a non-selective PKC activator alone but at a reduced concentration. The reduced concentration may be advantageous in that it may result in lower incidences of side effects.

Moreover, selective PKC activators, or combinations of at least one selective or non-selective PKC activator, may result in prolonged activation of PKC. Sustained activity is highly desirable for long-term clinical use.

PKC Activators

Activation of PKC generally involves binding to the DAG and/or the PS binding sites. Alternatively, PKC may be

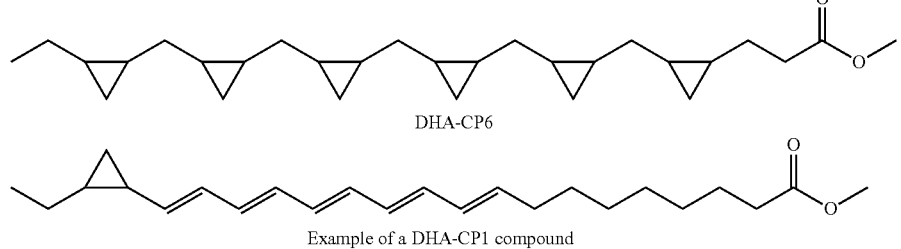

DHA-CP6

Example of a DHA-CP1 compound

As used herein, the word "cholesterol" refers to cholesterol and derivatives thereof. For example, "cholesterol" is understood to include the dihydrocholesterol species.

As used herein, the word "synaptogenesis" refers to a process involving the formation of synapses.

As used herein, the word "synaptic networks" refer to a multiplicity of neurons and synaptic connections between the individual neurons. Synaptic networks may include extensive branching with multiple interactions. Synaptic networks can be recognized, for example, by confocal visualization, electron microscopic visualization, and electrophysiologic recordings.

activated indirectly, e.g., by activating phospholipases such as phospholipase Cγ, by stimulating the Ser/Thr kinase Akt by way of phosphatidylinositol 3-kinase (PI3K), or by increasing the levels of DAG, the endogenous activator. Nelson et al., *Trends in Biochem. Sci.* (2009) vol. 34, pp. 136-145. Diacylglycerol kinase inhibitors, for example, may enhance the levels of the endogenous ligand diacylglycerol, thereby producing activation of PKC. Meinhardt et al., *Anti-Cancer Drugs* (2002), vol. 13, pp. 725-733. Phorbol esters are not suitable compounds for eventual drug development because of their tumor promotion activity. Ibarreta et al. *Neuroreport* (1999), vol. 10, pp. 1035-1040.

PKC activators suitable for the methods, compositions, and kits disclosed herein take a variety of forms.

One class of PKC activators is polyunsaturated fatty acids ("PUFAs"). These compounds are essential components of the nervous system and have numerous health benefits. In general, PUFAs increase membrane fluidity, rapidly oxidize to highly bioactive products, produce a variety of inflammatory and hormonal effects, and are rapidly degraded and metabolized. The inflammatory effects and rapid metabolism is likely the result of their active carbon-carbon double bonds. These compounds may be potent activators of PKC, most likely by binding the PS site.

In one embodiment, the PUFA is chosen from linoleic acid (shown below).

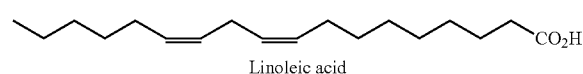

Linoleic acid

Another class of PKC activators is PUFA and MUFA derivatives, and cyclopropanated derivatives in particular. Certain cyclopropanated PUFAs, such as DCPLA (i.e., linoleic acid with cyclopropane at both double bonds), may be able to selectively activate PKC-ε. See *Journal of Biological Chemistry*, 2009, 284(50): 34514-34521; see also U.S. Patent Application Publication No. 2010/0022645 A1. Like their parent molecules, PUFA derivatives are thought to activate PKC by binding to the PS site.

Cyclopropanated fatty acids exhibit low toxicity and are readily imported into the brain where they exhibit a long half-life ($t_{1/2}$). Conversion of the double bonds into cyclopropane rings prevents oxidation and metabolism to inflammatory byproducts and creates a more rigid U-shaped 3D structure that may result in greater PKC activation. Moreover, this U-shape may result in greater isoform specificity. For example, cyclopropanated fatty acids may exhibit potent and selective activation of PKC-ε.

The Simmons-Smith cyclopropanation reaction is an efficient way of converting double bonds to cyclopropane groups. This reaction, acting through a carbenoid intermediate, preserves the cis-stereochemistry of the parent molecule. Thus, the PKC-activating properties are increased while metabolism into other molecules like bioreactive eicosanoids, thromboxanes, or prostaglandins is prevented.

One class of PKC-activating fatty acids is Omega-3 PUFA derivatives. In one embodiment, the Omega-3 PUFA derivatives are chosen from cyclopropanated docosahexaenoic acid, cyclopropanated eicosapentaenoic acid, cyclopropanated rumelenic acid, cyclopropanated parinaric acid, and cyclopropanated linolenic acid (CP3 form shown below).

Another class of PKC-activating fatty acids is Omega-6 PUFA derivatives. In one embodiment, the Omega-6 PUFA derivatives are chosen from cyclopropanated linoleic acid ("DCPLA," CP2 form shown below),

cyclopropanated arachidonic acid, cyclopropanated eicosadienoic acid, cyclopropanated dihomo-gamma-linolenic acid, cyclopropanated docosadienoic acid, cyclopropanated adrenic acid, cyclopropanated calendic acid, cyclopropanated docosapentaenoic acid, cyclopropanated jacaric acid, cyclopropanated pinolenic acid, cyclopropanated podocarpic acid, cyclopropanated tetracosatetraenoic acid, and cyclopropanated tetracosapentaenoic acid.

Vernolic acid is a naturally occurring compound. However, it is an epoxyl derivative of linoleic acid and therefore, as used herein, is considered an Omega-6 PUFA derivative. In addition to vernolic acid, cyclopropanated vernolic acid (shown below) is an Omega-6 PUFA derivative.

Another class of PKC-activating fatty acids is Omega-9 PUFA derivatives. In one embodiment, the Omega-9 PUFA derivatives are chosen from cyclopropanated eicosenoic acid, cyclopropanated mead acid, cyclopropanated erucic acid, and cyclopropanated nervonic acid.

Yet another class of PKC-activating fatty acids is monounsaturated fatty acid ("MUFA") derivatives. In one embodiment, the MUFA derivatives are chosen from cyclopropanated oleic acid (shown below),

and cyclopropanated elaidic acid (shown below).

PKC-activating MUFA derivatives include epoxylated compounds such as trans-9,10-epoxystearic acid (shown below).

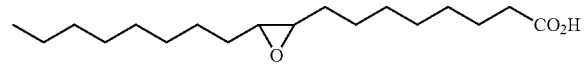 [SMILES: CCCCCCCCC1OC1CCCCCCCC(=O)O]

Another class of PKC-activating fatty acids is Omega-5 and Omega-7 PUFA derivatives. In one embodiment, the Omega-5 and Omega-7 PUFA derivatives are chosen from cyclopropanated rumenic acid, cyclopropanated alpha-elostearic acid, cyclopropanated catalpic acid, and cyclopropanated punicic acid.

Another class of PKC activators is fatty acid alcohols and derivatives thereof, such as cyclopropanated PUFA and MUFA fatty alcohols. It is thought that these alcohols activate PKC by binding to the PS site. These alcohols can be derived from different classes of fatty acids.

In one embodiment, the PKC-activating fatty alcohols are derived from Omega-3 PUFAs, Omega-6 PUFAs, Omega-9 PUFAs, and MUFAs, especially the fatty acids noted above. In one embodiment, the fatty alcohol is chosen from cyclopropanated linolenyl alcohol (CP3 form shown below),

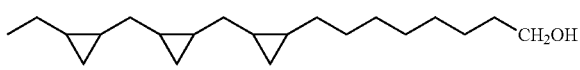 [SMILES: CCC1CC1CC1CC1CC1CC1CCCCCCCCO]

cyclopropanated linoleyl alcohol (CP2 form shown below),

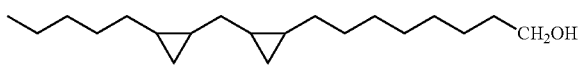 [SMILES: CCCCCC1CC1CC1CC1CCCCCCCCO]

cyclopropanated elaidic alcohol (shown below),

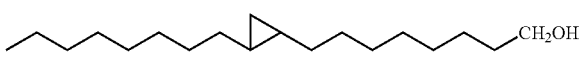 [SMILES: CCCCCCCCC1CC1CCCCCCCCO]

cyclopropanated DCPLA alcohol, and cyclopropanated oleyl alcohol.

Another class of PKC activators is fatty acid esters and derivatives thereof, such as cyclopropanated PUFA and MUFA fatty esters. In one embodiment, the cyclopropanated fatty esters are derived from Omega-3 PUFAs, Omega-6 PUFAs, Omega-9 PUFAs, MUFAs, Omega-5 PUFAs, and Omega-7 PUFAs. These compounds are thought to activate PKC through binding on the PS site. One advantage of such esters is that they are generally considered to be more stable that their free acid counterparts.

In one embodiment, the PKC-activating fatty acid esters derived from Omega-3 PUFAs are chosen from cyclopropanated eicosapentaenoic acid methyl ester (CP5 form shown below)

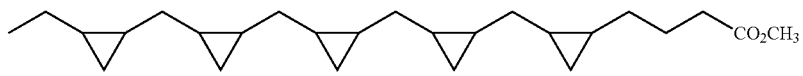 [SMILES: CCC1CC1CC1CC1CC1CC1CC1CC1CC1CC1CCCC(=O)OC]

and cyclopropanated linolenic acid methyl ester (CP3 form shown below).

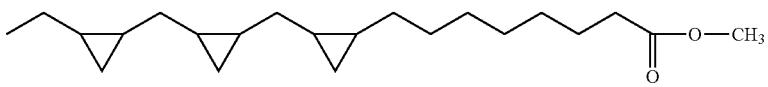 [SMILES: CCC1CC1CC1CC1CC1CC1CCCCCCCC(=O)OC]

In another embodiment, the Omega-3 PUFA esters are chosen from esters of DHA-CP6 and aliphatic and aromatic alcohols. In one embodiment, the ester is cyclopropanated docosahexaenoic acid methyl ester (CP6 form shown below).

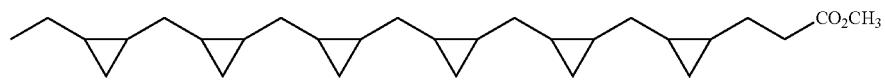 [SMILES: CCC1CC1CC1CC1CC1CC1CC1CC1CC1CC1CC1CC1CCC(=O)OC]

DHA-CP6, in fact, has been shown to be effective at a concentration of 10 nM. See, e.g., U.S. Patent Application Publication No. 2010/0022645.

In one embodiment, PKC-activating fatty esters derived from Omega-6 PUFAs are chosen from cyclopropanated arachidonic acid methyl ester (CP4 form shown below),

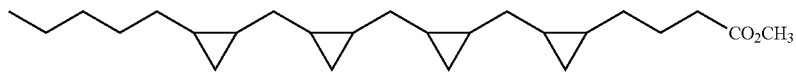 [SMILES: CCCCCC1CC1CC1CC1CC1CC1CC1CC1CCCC(=O)OC]

cyclopropanated vernolic acid methyl ester (CP1 form shown below), and

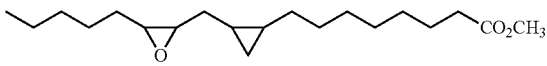

vernolic acid methyl ester (shown below).

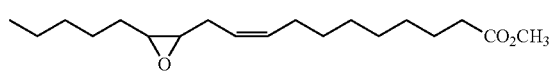

One particularly interesting class of esters are derivatives of DCPLA (CP6-linoleic acid). See, e.g., U.S. Provisional Patent Application No. 61/559,117 and applications claiming priority thereof. In one embodiment, the ester of DCPLA is an alkyl ester. The alkyl group of the DCPLA alkyl esters may be linear, branched, and/or cyclic. The alkyl groups may be saturated or unsaturated. When the alkyl group is an unsaturated cyclic alkyl group, the cyclic alkyl group may be aromatic. The alkyl group, in one embodiment, may be chosen from methyl, ethyl, propyl (e.g., isopropyl), and butyl (e.g., tert-butyl) esters. DCPLA in the methyl ester form ("DCPLA-ME") is shown below.

In another embodiment, the esters of DCPLA are derived from a benzyl alcohol (unsubstituted benzyl alcohol ester shown below). In yet another embodiment, the esters of DCPLA are derived from aromatic alcohols such as phenols used as antioxidants and natural phenols with pro-learning ability. Some specific examples include estradiol, butylated hydroxytoluene, resveratrol, polyhydroxylated aromatic compounds, and curcumin.

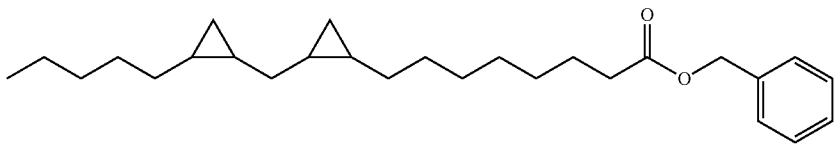

DCPLA-benzyl alcohol ester

Another class of PKC activators is fatty esters derived from cyclopropanated MUFAs. In one embodiment, the cyclopropanated MUFA ester is chosen from cyclopropanated elaidic acid methyl ester (shown below),

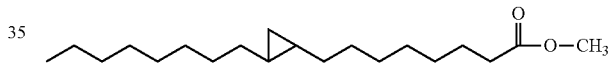

and cyclopropanated oleic acid methyl ester (shown below).

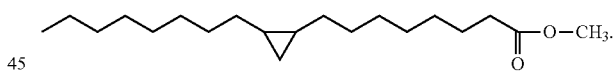

Another class of PKC activators is sulfates and phosphates derived from PUFAs, MUFAs, and their derivatives. In one embodiment, the sulfate is chosen from DCPLA sulfate and DHA sulfate (CP6 form shown below).

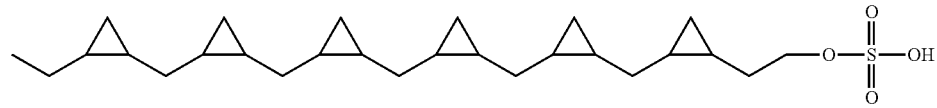 [SMILES: CCC1CC1CC1CC1CC1CC1CC1CC1CC1CC1CC1CC1CCOS(=O)(=O)O]

In one embodiment, the phosphate is chosen from DCPLA phosphate and DHA phosphate (CP6 form shown below).

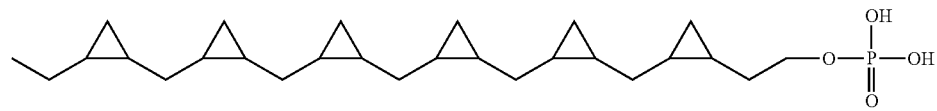 [SMILES: CCC1CC1CC1CC1CC1CC1CC1CC1CC1CC1CC1CC1CCOP(=O)(O)O]

Another class of PKC activators is macrocyclic lactones, e.g., the bryostatin and neristatin classes, which act to stimulate PKC. Macrocyclic lactones (also known as macrolides) generally comprise 14-, 15-, or 16-membered lactone rings. Macrolides belong to the polyketide class of natural products. Macrocyclic lactones and derivatives thereof are described, for example, in U.S. Pat. Nos. 6,187,568; 6,043,270; 5,393,897; 5,072,004; 5,196,447; 4,833,257; and 4,611,066; and 4,560,774; each incorporated by reference herein in its entirety. Those patents describe various compounds and various uses for macrocyclic lactones including their use as an anti-inflammatory or anti-tumor agent. See also Szallasi et al. *J. Biol. Chem.* (1994), vol. 269, pp. 2118-2124; Zhang et al., *Cancer Res.* (1996), vol. 56, pp. 802-808; Hennings et al. *Carcinogenesis* (1987), vol. 8, pp. 1343-1346; Varterasian et al. *Clin. Cancer Res.* (2000), vol. 6, pp. 825-828; Mutter et al. *Bioorganic & Med. Chem.* (2000), vol. 8, pp. 1841-1860; each incorporated by reference herein in its entirety.

Of the bryostatin class of compounds, Bryostatin-1 is particularly interesting. It has been shown to activate PKC without tumor promotion. Further, its dose response curve is biphasic. In addition, Bryostatin-1 demonstrates differential regulation of PKC isoforms including PKC-α, PKC-δ and PKC-ε. Given this potential, Bryostatin-1 has undergone toxicity and safety studies in animals and humans, and is actively being investigated as an anti-cancer agent as an adjuvant with other potential anti-cancer agents.

Bryostatins as a class are thought to bind to the C1a site (one of the DAG binding sites) and cause translocation like a phorbol ester, but unlike the phorbol esters, does not promote tumors. Bryostatin-1 exhibits no toxicity at 20 μg/week, although the use of more than 35 μg/week may be associated with muscle pain. In rats, the acute $LD_{50}$ value for Bryostatin-1 is 68 μg/kg, and the acute $LD_{10}$ value is 45 μg/kg. Death in high doses results from hemorrhage.

Bryostatin crosses the blood-brain barrier and is slowly eliminated from the brain, exhibiting slow dissociation kinetics ($t_{1/2}$>12 hr). In the blood stream, bryostatin has a short half life ($t_{1/2}$=1 hr). However, of an initial dose (via intravenous injection), 1% is in the blood at 100 hrs and is detectable in the blood for 14 days after a single injection. Bryostatin tends to accumulate in fatty tissues and is likely detoxified though glycolysation of OH groups and other well known pathways for detoxification of xenobiotic compounds.

In one embodiment of the present disclosure, the macrocyclic lactone is a bryostatin. Bryostatins include, for example, Bryostatin-1, Bryostatin-2, Bryostatin-3, Bryostatin-4, Bryostatin-5, Bryostatin-6, Bryostatin-7, Bryostatin-8, Bryostatin-9, Bryostatin-10, Bryostatin-11, Bryostatin-12, Bryostatin-13, Bryostatin-14, Bryostatin-15, Bryostatin-16, Bryostatin-17, and Bryostatin-18.

In at least one embodiment, the bryostatin is Bryostatin-1 (shown below).

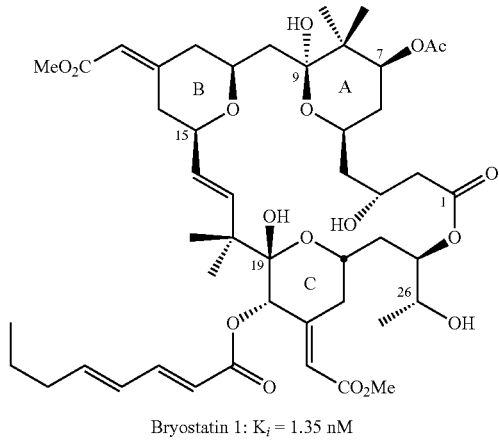

Bryostatin 1: $K_i$ = 1.35 nM

In another embodiment, the bryostatin is Bryostatin-2 (shown below; R=COC$_7$H$_{11}$, R'=H).

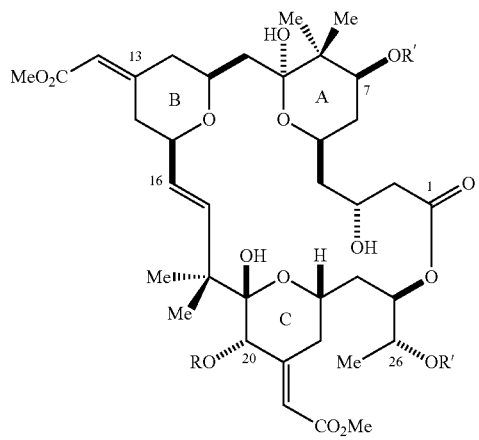

In one embodiment of the present disclosure, the macrocyclic lactone is a neristatin. In one embodiment, the neristatin is chosen from neristatin-1. In another embodiment, the macrocyclic lactone is chosen from macrocyclic derivatives of cyclopropanated PUFAs such as, 24-octaheptacyclononacosan-25-one (cyclic DHA-CP6) (shown below).

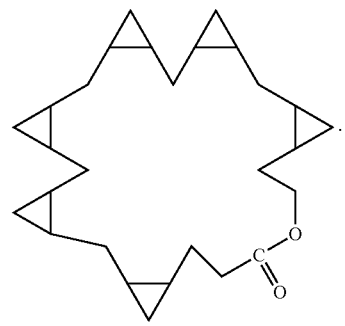 [SMILES: O=C1CCC2CC2CC2CC2CC2CC2CC2CC2CC2CC2CC2CC2CCO1]

In another embodiment, the macrocyclic lactone is a bryolog. Bryologs (analogs of bryostatin) are another class of PKC activators that are suitable for use in the present disclosure. Bryologs can be chemically synthesized or produced by certain bacteria. Different bryologs exist that modify, for example, the rings A, B, and C (see Bryostatin-1, figure shown above) as well as the various substituents. As a general overview, brylogs are considered less specific and less potent than bryostatin but are easier to prepare. It was found that the C-ring is important for binding to PKC while the A-ring is important for non-tumorigenesis. Further, the hydrophobic tail appears to be important for membrane binding.

Table 1 summarizes structural characteristics of several bryologs and demonstrates variability in their affinity for PKC (ranging from 0.25 nM to 10 μM). Structurally, they are all similar. While Bryostatin-1 has two pyran rings and one 6-membered cyclic acetal, in most bryologs one of the pyrans of Bryostatin-1 is replaced with a second 6-membered acetal ring. This modification reduces the stability of bryologs, relative to Bryostatin-1, for example, in both strong acid or base, but has little significance at physiological pH. Bryologs also have a lower molecular weight (ranging from about 600 g/mol to 755 g/mol), as compared to Bryostatin-1 (988), a property which facilitates transport across the blood-brain barrier.

TABLE 1
Bryologs.

| Name | PKC Affin (nM) | MW | Description |
| --- | --- | --- | --- |
| Bryostatin-1 | 1.35 | 988 | 2 pyran + 1 cyclic acetal + macrocycle |
| Analog 1 | 0.25 | 737 | 1 pyran + 2 cyclic acetal + macrocycle |
| Analog 2 | 6.50 | 723 | 1 pyran + 2 cyclic acetal + macrocycle |
| Analog 7a | — | 642 | 1 pyran + 2 cyclic acetals + macrocycle |
| Analog 7b | 297 | 711 | 1 pyran + 2 cyclic acetals + macrocycle |
| Analog 7c | 3.4 | 726 | 1 pyran + 2 cyclic acetals + macrocycle |
| Analog 7d | 10000 | 745 | 1 pyran + 2 cyclic acetals + macrocycle, acetylated |
| Analog 8 | 8.3 | 754 | 2 cyclic acetals + macrocycle |
| Analog 9 | 10000 | 599 | 2 cyclic acetals |

Analog 1 exhibits the highest affinity for PKC. Wender et al., *Curr. Drug Discov. Technol.* (2004), vol. 1, pp. 1-11; Wender et al. *Proc. Natl. Acad. Sci.* (1998), vol. 95, pp. 6624-6629; Wender et al., *J. Am. Chem. Soc.* (2002), vol. 124, pp. 13648-13649, each incorporated by reference herein in their entireties. Only Analog 1 exhibits a higher affinity for PKC than Bryostatin-1. Analog 2, which lacks the A ring of Bryostatin-1, is the simplest analog that maintains high affinity for PKC. In addition to the active bryologs, Analog 7d, which is acetylated at position 26, has virtually no affinity for PKC.

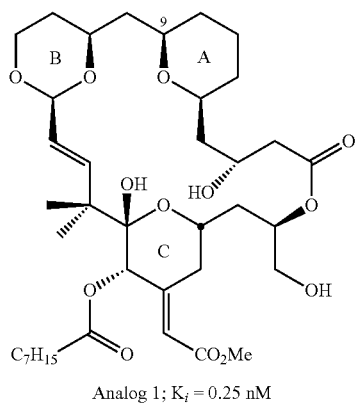

Analog 1; $K_i = 0.25$ nM

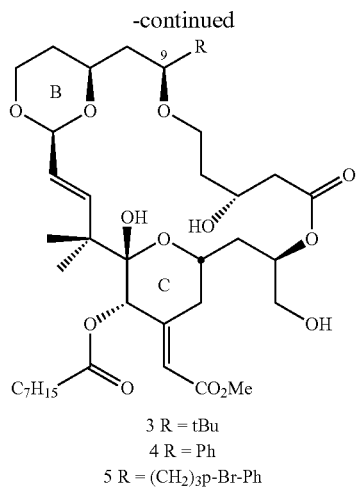

3 R = tBu
4 R = Ph
5 R = (CH$_2$)$_3$p-Br-Ph

B-ring bryologs may also be used in the present disclosure. These synthetic bryologs have affinities in the low nanomolar range. Wender et al., *Org Lett.* (2006), vol. 8, pp. 5299-5302, incorporated by reference herein in its entirety. B-ring bryologs have the advantage of being completely synthetic, and do not require purification from a natural source.

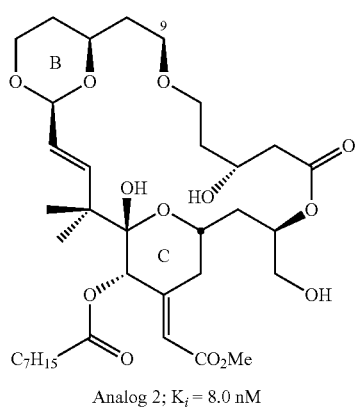

Analog 2; $K_i = 8.0$ nM

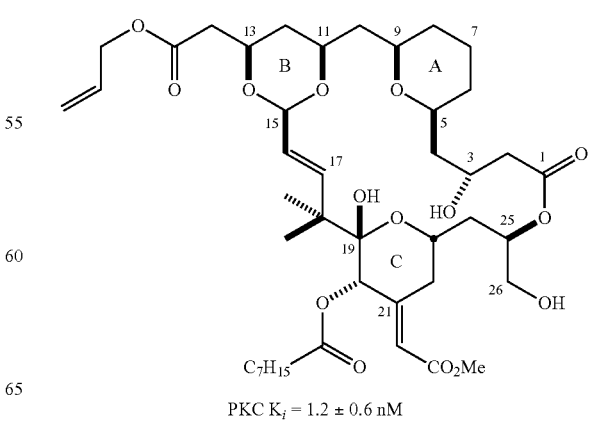

PKC $K_i = 1.2 \pm 0.6$ nM

-continued

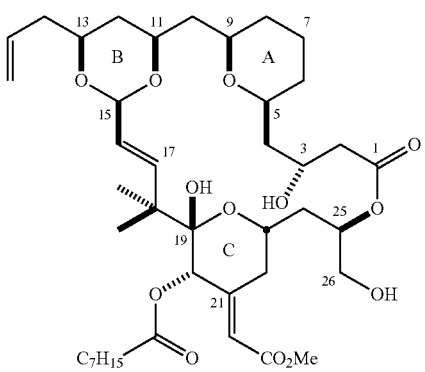

PKC $K_i = 0.67 \pm 0.5$ nM

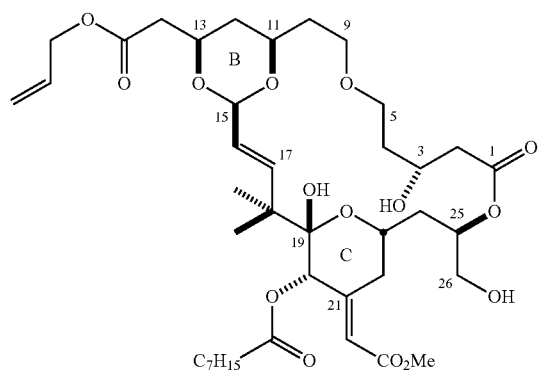

PKC $K_i = 3.0 \pm 0.5$ nM

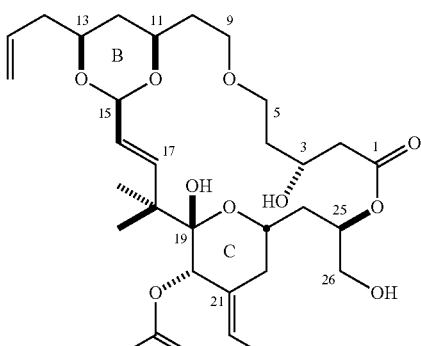

PKC $K_i = 2.6 \pm 0.5$ nM

A third class of suitable bryostatin analogs are the A-ring bryologs. These bryologs have slightly lower affinity for PKC than Bryostatin-1 (6.5 nM, 2.3 nM, and 1.9 nM for bryologs 3, 4, and 5, respectively) and a lower molecular weight. A-ring substituents are important for non-tumorigenesis.

Bryostatin analogs are described, for example, in U.S. Pat. Nos. 6,624,189 and 7,256,286. Methods using macrocyclic lactones to improve cognitive ability are also described in U.S. Pat. No. 6,825,229 B2.

Another class of PKC activators is derivatives of diacylglycerols that bind to and activate PKC. See, e.g., Niedel et al., *Proc. Natl. Acad. Sci.* (1983), vol. 80, pp. 36-40; Mori et al., *J. Biochem.* (1982), vol. 91, pp. 427-431; Kaibuchi et al., *J. Biol. Chem.* (1983), vol. 258, pp. 6701-6704. Activation of PKC by diacylglycerols is transient, because they are rapidly metabolized by diacylglycerol kinase and lipase. Bishop et al. *J. Biol. Chem.* (1986), vol. 261, pp. 6993-7000; Chuang et al. *Am. J. Physiol.* (1993), vol. 265, pp. C927-C933; incorporated by reference herein in their entireties. The fatty acid substitution on the diacylglycerols derivatives determines the strength of activation. Diacylglycerols having an unsaturated fatty acid are most active. The stereoisomeric configuration is important; fatty acids with a 1,2-sn configuration are active while 2,3-sn-diacylglycerols and 1,3-diacylglycerols do not bind to PKC. Cis-unsaturated fatty acids may be synergistic with diacylglycerols. In at least one embodiment, the term "PKC activator" expressly excludes DAG or DAG derivatives.

Another class of PKC activators is isoprenoids. Farnesyl thiotriazole, for example, is a synthetic isoprenoid that activates PKC with a $K_d$ of 2.5 µM. Farnesyl thiotriazole, for example, is equipotent with dioleoylglycerol, but does not possess hydrolyzable esters of fatty acids. Gilbert et al., *Biochemistry* (1995), vol. 34, pp. 3916-3920; incorporated by reference herein in its entirety. Farnesyl thiotriazole and related compounds represent a stable, persistent PKC activator. Because of its low molecular weight (305.5 g/mol) and absence of charged groups, farnesyl thiotriazole would be expected to readily cross the blood-brain barrier.

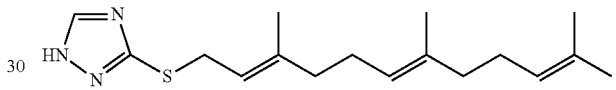

Yet another class of activators includes octylindolactam V, gnidimacrin, and ingenol. Octylindolactam V is a non-phorbol protein kinase C activator related to teleocidin. The advantages of octylindolactam V (specifically the (−)-enantiomer) include greater metabolic stability, high potency ($EC_{50}=29$ nM) and low molecular weight that facilitates transport across the blood brain barrier. Fujiki et al. *Adv. Cancer Res.* (1987), vol. 49 pp. 223-264; Collins et al. *Biochem. Biophys. Res. Commun.* (1982), vol. 104, pp. 1159-4166, each incorporated by reference herein in its entirety.

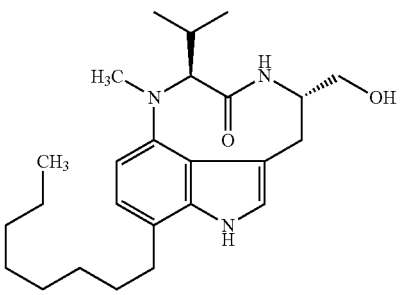 [SMILES: CCCCCCCCc1ccc2c3c(c[nH]c13)C[C@@H](CO)NC(=O)[C@H](C(C)C)N2C]

Gnidimacrin is a daphnane-type diterpene that displays potent antitumor activity at concentrations of 0.1 nM-1 nM against murine leukemias and solid tumors. It acts as a PKC activator at a concentration of 0.3 nM in K562 cells, and regulates cell cycle progression at the G1/S phase through the suppression of Cdc25A and subsequent inhibition of cyclin dependent kinase 2 (Cdk2) (100% inhibition achieved at 5 ng/ml). Gnidimacrin is a heterocyclic natural product similar to Bryostatin-1, but somewhat smaller (MW=774.9 g/mol).

Iripallidal is a bicyclic triterpenoid isolated from *Iris pallida*. Iripallidal displays anti-proliferative activity in a NCI 60 cell line screen with $GI_{50}$ (concentration required to inhibit growth by 50%) values from micromolar to nanomolar range. It binds to PKCα with high affinity ($K_i$=75.6 nM). It induces phosphorylation of Erk1/2 in a RasGRP3-dependent manner. Its molecular weight is 486.7 g/mol. Iripallidal is about half the size of Bryostatin-1 and lacks charged groups.

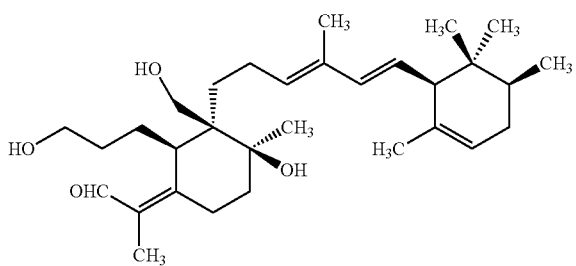

Ingenol is a diterpenoid related to phorbol but less toxic. It is derived from the milkweed plant *Euphorbia peplus*. Ingenol 3,20-dibenzoate, for example, competes with [3H] phorbol dibutyrate for binding to PKC ($K_i$=240 nM). Winkler et al., *J. Org. Chem.* (1995), vol. 60, pp. 1381-1390, incorporated by reference herein. Ingenol-3-angelate exhibits antitumor activity against squamous cell carcinoma and melanoma when used topically. Ogbourne et al. *Anticancer Drugs* (2007), vol. 18, pp. 357-362, incorporated by reference herein.

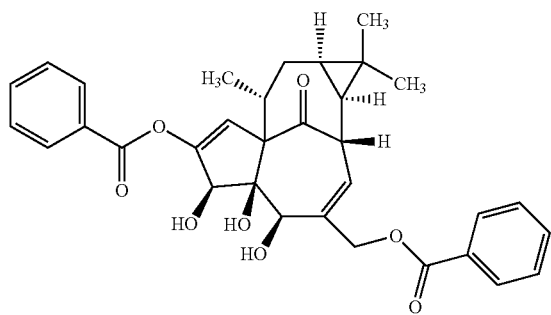 [SMILES: C[C@@H]1C[C@@H]2[C@H]([C@@H]3C=C(COC(=O)c4ccccc4)[C@@H](O)[C@]4(O)[C@@H](O)C(OC(=O)c5ccccc5)=CC14C3=O)C2(C)C]

Another class of PKC activators is napthalenesulfonamides, including N-(n-heptyl)-5-chloro-1-naphthalenesulfonamide (SC-10) and N-(6-phenylhexyl)-5-chloro-1-naphthalenesulfonamide. SC-10 activates PKC in a calcium-dependent manner, using a mechanism similar to that of phosphatidylserine. Ito et al., *Biochemistry* (1986), vol. 25, pp. 4179-4184, incorporated by reference herein. Naphthalenesulfonamides act by a different mechanism than bryostatin and may show a synergistic effect with bryostatin or member of another class of PKC activators. Structurally, naphthalenesulfonamides are similar to the calmodulin (CaM) antagonist W-7, but are reported to have no effect on CaM kinase.

Yet another class of PKC activators is diacylglycerol kinase inhibitors, which indirectly activate PKC. Examples of diacylglycerol kinase inhibitors include, but are not limited to, 6-(2-(4-[(4-fluorophenyl)phenylmethylene]-1-piperidinyl)ethyl)-7-methyl-5H-thiazolo[3,2-a]pyrimidin-5-one (R59022) and [3-[2-[4-(bis-(4-fluorophenyl)methylene] piperidin-1-yl)ethyl]-2,3-dihydro-2-thioxo-4(1H)-quinazolinone (R59949).

Still another class of PKC activators is growth factors, such as fibroblast growth factor 18 (FGF-18) and insulin growth factor, which function through the PKC pathway. FGF-18 expression is up-regulated in learning, and receptors for insulin growth factor have been implicated in learning. Activation of the PKC signaling pathway by these or other growth factors offers an additional potential means of activating PKC.

Another class of PKC activators is hormones and growth factor activators, including 4-methyl catechol derivatives like 4-methylcatechol acetic acid (MCBA) that stimulate the synthesis and/or activation of growth factors such as NGF and BDNF, which also activate PKC as well as convergent pathways responsible for synaptogenesis and/or neuritic branching.

PKC-Activating Combinations

PKC-activating compounds may also be used in combination form. As used herein, a "combination" refers to mixtures, conjugates, and/or use combinations. Each of these types of combinations comprises at least one PKC activator and another PKC activator(s) or other agent(s), such as a retinoid or cholesterol.

"Mixtures" refer to a mix of at least one PKC activator and at least one other PKC activator or at least one other agent. In one embodiment, a mixture may comprise at least one PKC activator and at least one retinoid.

In one embodiment, the present disclosure relates to mixtures comprising at least two PKC activators. The PKC activators can be chosen from cyclopropanated polyunsaturated fatty acids, cyclopropanated monounsaturated fatty acids, cyclopropanated polyunsaturated fatty alcohols, cyclopropanated monounsaturated fatty alcohols, cyclopropanated polyunsaturated fatty acid esters, cyclopropanated monounsaturated fatty acid esters, cyclopropanated polyunsaturated fatty acid sulfates, cyclopropanated monounsaturated fatty acid sulfates, cyclopropanated polyunsaturated fatty acid phosphates, cyclopropanated monounsaturated fatty acid phosphates, macrocyclic lactones, DAG derivatives, isoprenoids, octylindolactam V, gnidimacrin, iripallidal, ingenol, napthalenesulfonamides, diacylglycerol kinase inhibitors, fibroblast growth factor 18 (FGF-18), insulin growth factor, hormones, growth factor activators, cyclopropanated polyunsaturated fatty acid conjugates, cyclopropanated monounsaturated fatty acid conjugates, bryostatin conjugates, bryolog conjugates, and retinoic acid conjugates.

In one embodiment, the mixture comprises a DCPLA ester and a bryostatin. In another embodiment, the mixture comprises DCPLA methyl ester and Bryostatin-1. In another embodiment, the mixture comprises a DHA-CP6 ester and a DHA-CP6 diacylglycerol ester. In yet another embodiment, the mixture comprises Bryostatin-1 and DHA-CP6 methyl ester.

In another embodiment, the present disclosure relates to mixtures comprising at least one PKC activator and at least one retinoid. A retinoid is any natural or synthetic analog of Vitamin A. These analogs include the metabolites of Vitamin A, such as all-trans retinoic acid. Other examples of retinoids include N-(4-hydroxyphenyl) retinamide ("4-HPR"); 4-(5,5,8,8-Tetramethyl-5,6,7,8-tetrahydronaphthalen-2-yl-ethynyl)benzoic acid ("ec23"); 9-cis retinoic acid (shown below);

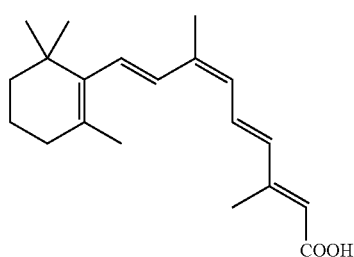 [SMILES: CC1=C(/C=C/C(C)=C\C=C\C(C)=C\C(=O)O)C(C)(C)CCC1]
13-cis retinoic acid (shown below);
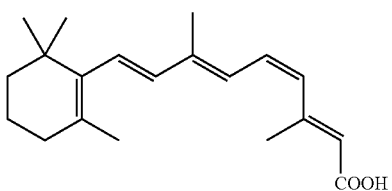 [SMILES: CC1=C(/C=C/C(C)=C/C=C\C(C)=C\C(=O)O)C(C)(C)CCC1]
all-trans-4-hydroxyretinoic acid (shown below);
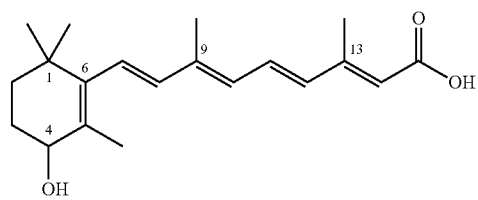 [SMILES: CC1=C(/C=C/C(C)=C/C=C/C(C)=C/C(=O)O)C(C)(C)CCC1O]
all-trans-4-oxoretinoic acid (shown below);
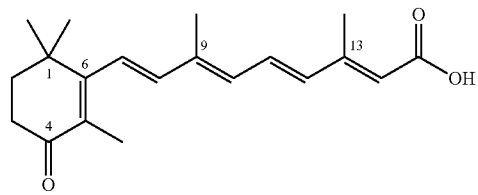 [SMILES: CC1=C(/C=C/C(C)=C/C=C/C(C)=C/C(=O)O)C(C)(C)CCC1=O]
3,4, didehydroretinoic acid (shown below);
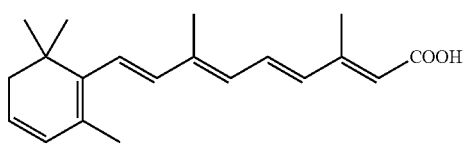 [SMILES: CC1=C(/C=C/C(C)=C/C=C/C(C)=C/C(=O)O)C(C)(C)CC=C1]
retinol (shown below);
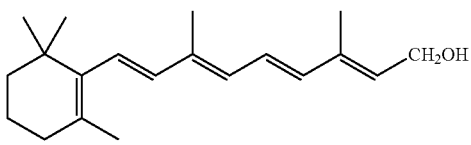 [SMILES: CC1=C(/C=C/C(C)=C/C=C/C(C)=C/CO)C(C)(C)CCC1]
retroretinol (shown below);
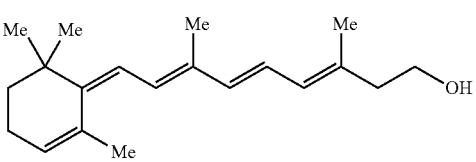 [SMILES: CC1=CCCC(C)(C)/C1=C/C=C(C)/C=C/C=C(\C)CCO]
all-trans-4-hydroxyretinol (shown below);
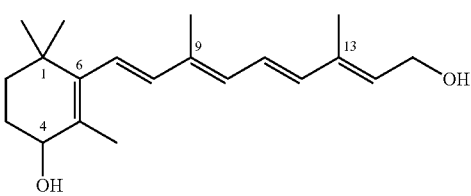 [SMILES: CC1=C(/C=C/C(C)=C/C=C/C(C)=C/CO)C(C)(C)CCC1O]
all-trans-4-oxoretinol (shown below);
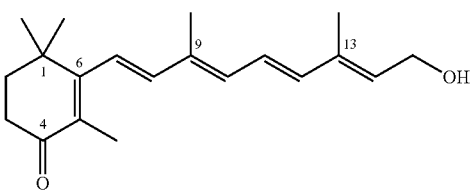 [SMILES: CC1=C(/C=C/C(C)=C/C=C/C(C)=C/CO)C(C)(C)CCC1=O]
14-hydroxy-4, 14-retroretinol (shown below);
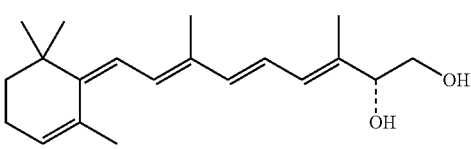 [SMILES: CC1=CCCC(C)(C)/C1=C/C=C(C)/C=C/C=C(\C)[C@@H](O)CO]
retinaldehyde (shown below);
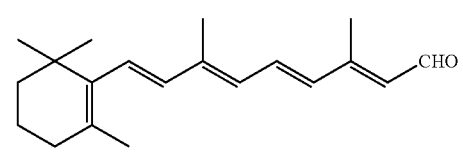 [SMILES: CC1=C(/C=C/C(C)=C/C=C/C(C)=C/C=O)C(C)(C)CCC1]
lycopene (shown below);

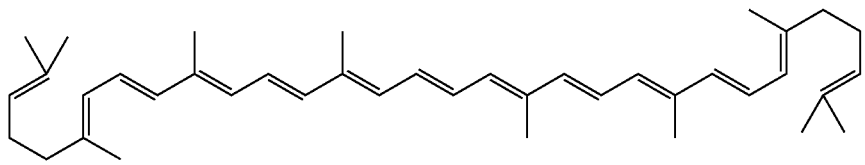 [SMILES: CC(C)=CCC/C(C)=C/C=C/C(C)=C/C=C/C(C)=C/C=C/C=C(C)/C=C/C=C(C)/C=C/C=C(\C)CCC=C(C)C]

apo-10'-lycopenoic acid (shown below);

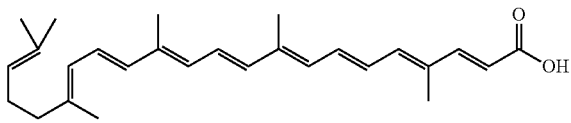 [SMILES: CC(C)=CCC/C(C)=C/C=C/C(C)=C/C=C/C(C)=C/C=C/C=C(C)/C=C/C(=O)O]

and acycloretinoic acid (shown below).

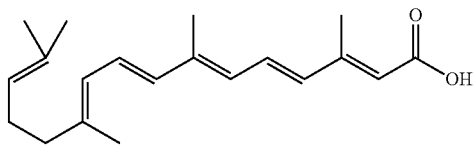 [SMILES: CC(C)=CCC/C(C)=C/C=C/C(C)=C/C=C/C(C)=C/C(=O)O]

A person with skill in the art understands that the acidic retinoids also have alcohol and anhydride forms.

In one embodiment, the at least one PKC activator of the retinoid mixture is chosen from cyclopropanated polyunsaturated fatty acids, cyclopropanated monounsaturated fatty acids, cyclopropanated polyunsaturated fatty alcohols, cyclopropanated monounsaturated fatty alcohols, cyclopropanated polyunsaturated fatty acid esters, cyclopropanated monounsaturated fatty acid esters, cyclopropanated polyunsaturated fatty acid sulfates, cyclopropanated monounsaturated fatty acid sulfates, cyclopropanated polyunsaturated fatty acid phosphates, cyclopropanated monounsaturated fatty acid phosphates, macrocyclic lactones, DAG derivatives, isoprenoids, octylindolactam V, gnidimacrin, iripallidal, ingenol, napthalenesulfonamides, diacylglycerol kinase inhibitors, fibroblast growth factor 18 (FGF-18), insulin growth factor, hormones, growth factor activators, cyclopropanated polyunsaturated fatty acid conjugates, cyclopropanated monounsaturated fatty acid conjugates, bryostatin conjugates, bryolog conjugates, and retinoic acid conjugates.

In one embodiment, the mixture comprises Bryostatin-1 and retinoic acid. In another embodiment, the mixture comprises DCPLA-methyl ester and retinoic acid. In yet another embodiment the mixture comprises DHA-CP6 methyl ester and retinoic acid.

In yet another embodiment, the present disclosure relates to mixtures comprising at least one LDL particle and at least one PKC activator. LDL particles can mediate transport of drugs across the blood-brain barrier. It is thought that, once the drug is associated with an LDL particle, the apolipoprotein receptors on the surface of the LDL particle target the apolipoprotein receptors on the blood-brain barrier surface. The LDL particle is presumably taken up by endothelial cells through transcytosis, and as cholesterol is absorbed by the cell, the drug is automatically released, thus enhancing the distribution of the drug in the brain, through release by endogenous esterases. Artificial LDL particles can be prepared such that they are non-toxic. The use of LDL as a transport carrier is described in U.S. Pat. Nos. 7,576,055 B2, and 7,803,400 B2.

In one embodiment, the mixture comprises at least one LDL particle and at least one PKC activator chosen from cyclopropanated polyunsaturated fatty acid conjugates, cyclopropanated monounsaturated fatty acid conjugates, bryostatin conjugates, bryolog conjugates, and retinoic acid conjugates. In one embodiment, the at least one PKC activator in the mixture is chosen from bryostatin-cholesterol conjugates, DCPLA-cholesterol conjugates, and retinoid acid-cholesterol conjugates (as described below). In another embodiment, the mixture comprises at least one LDL particle, at least one bryostatin-cholesterol conjugate, and at least one retinoic acid-cholesterol conjugate. In a further embodiment, the mixture comprises at least one LDL particle, at least one bryostatin-cholesterol conjugate, and at least one DCPLA-cholesterol conjugate.

In one embodiment, the present disclosure relates to mixtures chosen from mixtures comprising brain-derived neurotrophic factor ("BDNF") and at least one LDL particle, mixtures comprising nerve growth factor ("NGF") and at least one LDL particle, mixtures comprising glial cell derived neurotrophic factor ("GDNF") and at least one LDL particle, mixtures comprising basic fibroblast growth factor ("bFGF") and at least one LDL particle, and mixtures comprising retinoids and at least one LDL particle.

In one embodiment, the at least one LDL particle is an artificial LDL particle. In another embodiment, the at least one LDL particle is associated with apolipoprotein B. In yet another embodiment, the at least one LDL particle is associated with apolipoprotein E.

"Conjugates" refer to molecules comprising at least one PKC activator covalently bound to at least one other molecule. In one embodiment, a conjugate might be two PKC activators bound together. In another embodiment, a conjugate is a PKC activator bound to another agent (e.g., a retinoid or cholesterol).

The covalent bond in the conjugates can take many forms. Some forms include, but are not limited to, ester bonds, ether bonds, carbon-carbon single bonds, carbon-carbon double bonds, amide bonds, sulfur bonds, phosphate bonds, or bonds through any linker molecule.

In one embodiment, the PKC-activating conjugates are chosen from bryostatin conjugates, retinoid conjugates, cyclopropanated PUFA conjugates, and cyclopropanated MUFA conjugates. Bryostatins and bryologs are thought to bind to the DAG binding site of PKC. PUFAs and MUFAs are thought to bind to the PS binding site of PKC. Thus, conjugates of these compounds might bind to either the DAG or PS site, and possibly both.

In one embodiment, the PKC-activating conjugates are chosen from Bryostatin-1-retinoic acid ester, Bryostatin-1-cholesterol ester, and Bryostatin-1-DCPLA ester (di-DCPLA ester shown below).

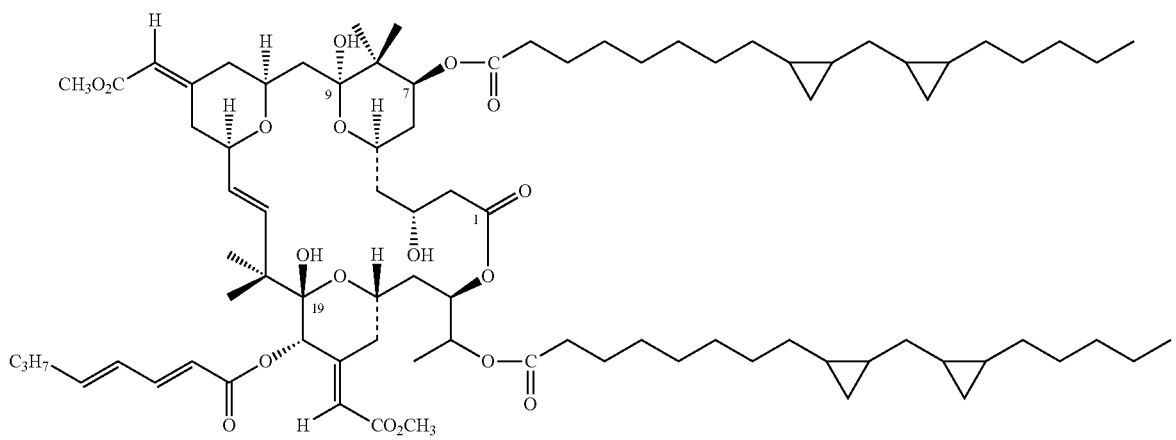

Some additional embodiments of bryostatin conjugates include, but are not limited to, bryostatin-cholesterol conjugates, fluorescent bryostatin-bodipy conjugates, and bryologs-DCPLA conjugates.

In another embodiment, the present disclosure relates to cyclopropanated PUFA and MUFA conjugates. In one embodiment, cyclopropanated PUFA and MUFA is conjugated with a cholesterol or cholesterol derivative conjugate. Exemplary conjugates include DHA-CP6 cholesteryl ester (CP6 form shown below) and

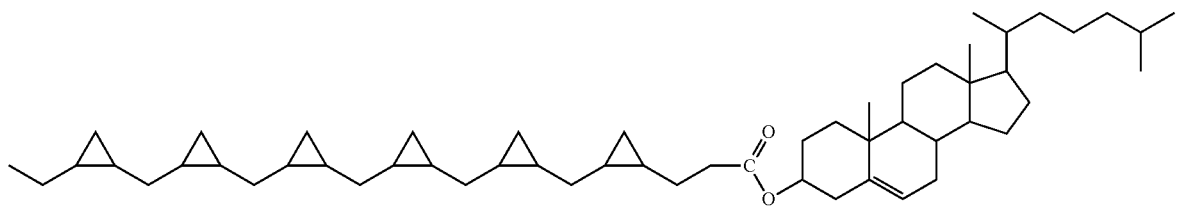 [SMILES: CCC1CC1CC1CC1CC1CC1CC1CC1CC1CC1CC1CC1CCC(=O)OC1CCC2(C)C(=CCC3C2CCC2(C)C(C(C)CCCC(C)C)CCC32)C1]

and DCPLA-cholesteryl ester (shown below).

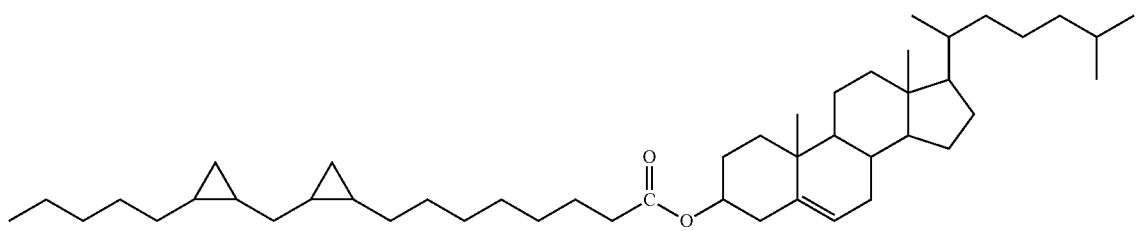 [SMILES: CCCCCC1CC1CC1CC1CCCCCCCC(=O)OC1CCC2(C)C(=CCC3C2CCC2(C)C(C(C)CCCC(C)C)CCC32)C1]

In another embodiment, the conjugate is a DHA-CP6 diacylglycerol ester (one embodiment shown below; the R group can be wherein the R group is any fatty acid chain. In one embodiment, the R group is chosen from oleic, palmitic, arachidonic, and docosahexaenoic fatty acid chains.

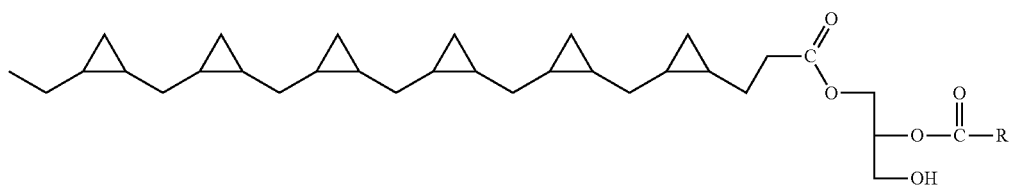

In another embodiment, the conjugate is a DHA-CP-DHA-CP ester (CP6-CP6 form shown below).

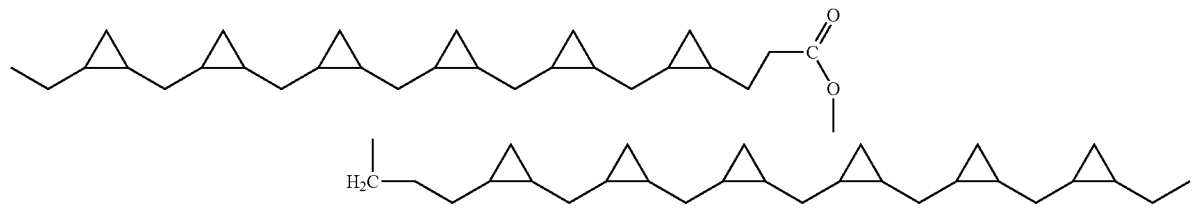

In one embodiment, the DHA-CP6 diacylglycerol ester is an ester of 1-palmitoyl-2-oleoyl-glycerol where the DHA-CP6 is bonded to the free —OH group of the glycerol backbone. In another embodiment, the conjugate is a DCPLA ester conjugate. See, e.g., U.S. Provisional Patent Application No. 61/559,117 and applications claiming priority thereof. In one embodiment, the conjugate is a DCPLA-oleyl ester (shown below). Other examples of fatty alcohols from which the DCPLA esters may be composed include linolenic alcohol, docosahexaenoic alcohol, eicosapentaenoic alcohol, and linoleic alcohol. The stereochemistry of double bonds in the fatty alcohols may be cis or trans.

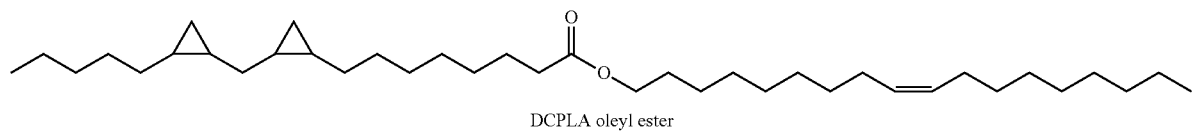 [SMILES: CCCCCCCC/C=C\CCCCCCCCOC(=O)CCCCCCCC1CC1CC1CC1CCCCC]

DCPLA oleyl ester

In another embodiment, the DCPLA ester is derived from DCPLA and a cyclopropanated PUFA or MUFA alcohol. In one embodiment, cyclopropanated fatty alcohols from which the DCPLA esters may be derived include cyclopropanated linoleic alcohol, cyclopropanated linolenic alcohol, and cyclopropanated eicosapentaenoic alcohol. When the ester is derived from cyclopropanated linoleic alcohol where all carbon-carbon double bonds have been cyclopropanated, the compound is the DCPLA-DCPLA ester (shown below).

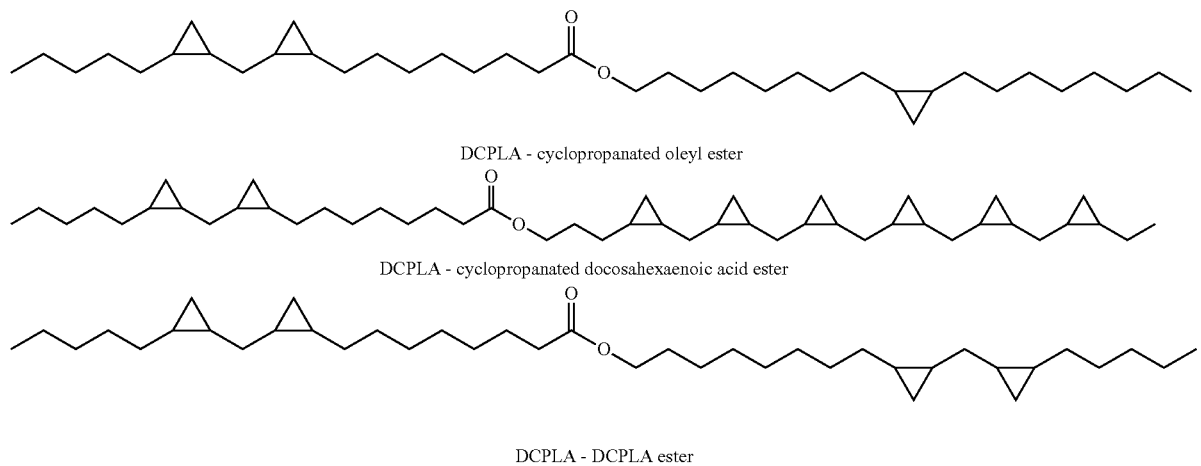

DCPLA - cyclopropanated oleyl ester

DCPLA - cyclopropanated docosahexaenoic acid ester

DCPLA - DCPLA ester

In another embodiment, the DCPLA ester is a diacylglycerol ester. For example, the DCPLA ester is derived from 1-palmitoyl-2-oleoyl-glycerol (shown below).

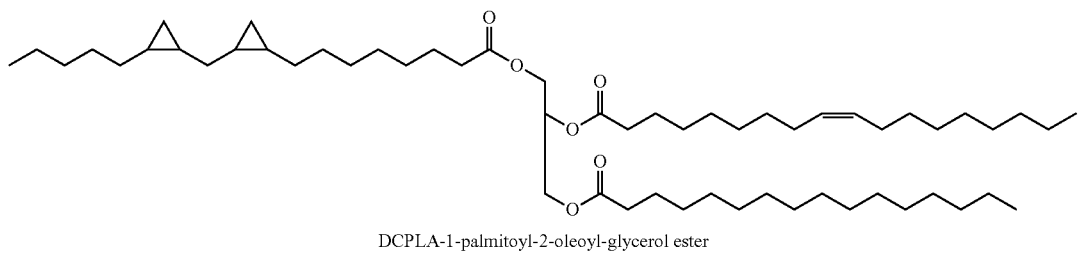 [SMILES: CCCCCCCC/C=C\CCCCCCCC(=O)OC(COC(=O)CCCCCCCCCCCCCCC)COC(=O)CCCCCCCC1CC1CC1CC1CCCCC]

DCPLA-1-palmitoyl-2-oleoyl-glycerol ester

In yet another embodiment, the DCPLA ester may be DCPLA-phosphatidyl serine (shown below) wherein the R group is any fatty acid chain. In one embodiment, the R group is chosen from oleic, palmitic, arachidonic, and docosahexaenoic fatty acid chains.

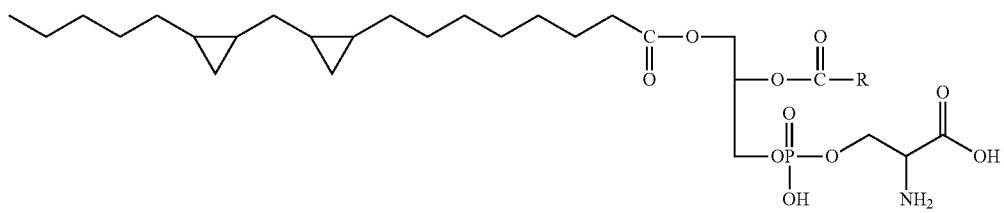

In one embodiment, the PKC-activating conjugates are derived from retinoids. In one embodiment, the conjugates are chosen from retinoic acid-cholesterol ester and cyclopropanated PUFAs with retinol or retinoic acid. In one embodiment, the retinoid conjugate is the DHA-retinol ester (CP6 form shown below).

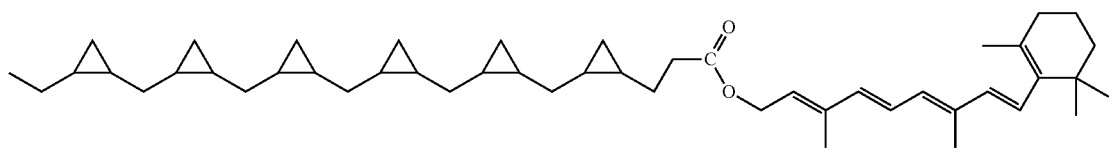 [SMILES: CCC1CC1CC1CC1CC1CC1CC1CC1CC1CC1CC1CC1CCC(=O)OC/C=C(C)/C=C/C=C(C)/C=C/C1=C(C)CCCC1(C)C]

In another embodiment, the retinoid conjugate is the retinoic acid-DHA ester (CP6 forms shown below).

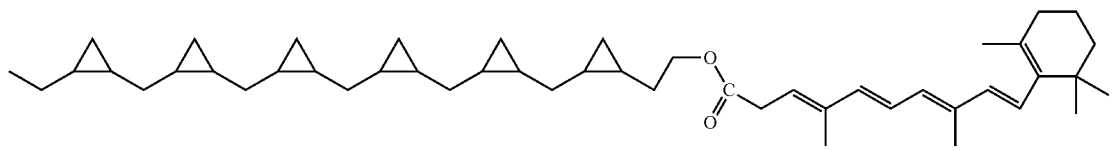 [SMILES: CCC1CC1CC1CC1CC1CC1CC1CC1CC1CC1CC1CC1CCOC(=O)C/C=C(C)/C=C/C=C(C)/C=C/C1=C(C)CCCC1(C)C]

In yet another embodiment, the retinoid conjugate is chosen from DCPLA-retinol ester and retinoic acid-DCPLA ester.

In another embodiment, the PKC-activating conjugates are derived from LDL particles. In one embodiment, the conjugate is an LDL particle bound to a PKC activator chosen from cyclopropanated PUFAs, cyclopropanated MUFAs, cyclopropanated PUFA alcohols, cyclopropanated MUFA alcohols, cyclopropanated PUFA esters, cyclopropanated MUFA esters, cyclopropanated PUFA sulfates, cyclopropanated MUFA sulfates, cyclopropanated PUFA phosphates, cyclopropanated MUFA phosphates, macrocyclic lactones, DAG derivatives, isoprenoids, octylindolactam V, gnidimacrin, iripallidal, ingenol, napthalenesulfonamides, diacylglycerol kinase inhibitors, fibroblast growth factor 18 (FGF-18), insulin growth factor, hormones, and growth factor activators. In another embodiment, the conjugate is an LDL particle bound to a PKC activator chosen from bryostatin, bryostatin conjugates, bryolog conjugates, and retinoic acid conjugates. In one embodiment, the LDL particle is artificial.

"Use combinations" refer to the administration of at least two components—e.g., (1) a PKC activator and (2) another PKC activator(s) or other agent(s) (such as a retinoid or cholesterol). In a use combination, the at least two components are administered to the same subject but need not be administered in the same composition and at the same time. In one embodiment, in a two-component use combination, one component may be administered before the other component. In another embodiment, the at least two components are administered at the same time in the same composition. In yet another embodiment, the at least two components are administered at the same time but are formulated into different compositions In this embodiment, the at least one PKC activator in the use combination is chosen from cyclopropanated polyunsaturated fatty acids, cyclopropanated monounsaturated fatty acids, cyclopropanated polyunsaturated fatty alcohols, cyclopropanated monounsaturated fatty alcohols, cyclopropanated polyunsaturated fatty acid esters, cyclopropanated monounsaturated fatty acid esters, cyclopropanated polyunsaturated fatty acid sulfates, cyclopropanated monounsaturated fatty acid sulfates, cyclopropanated polyunsaturated fatty acid phosphates, cyclopropanated monounsaturated fatty acid phosphates, macrocyclic lactones, DAG derivatives, isoprenoids, octylindolactam V, gnidimacrin, iripallidal, ingenol, napthalenesulfonamides, diacylglycerol kinase inhibitors, fibroblast growth factor 18 (FGF-18), insulin growth factor, hormones, growth factor activators, cyclopropanated polyunsaturated fatty acid conjugates, cyclopropanated monounsaturated fatty acid conjugates, bryostatin conjugates, bryolog conjugates, and retinoic acid conjugates. The other agent is chosen from PKC activators and other compounds like retinoids or cholesterols.

In one embodiment, the use combination comprises Bryostatin-1 and/or DCPLA methyl ester and retinoic acid administered in the same composition at the same time. In another embodiment, the use combination comprises Bryostatin-1 and/or DCPLA methyl ester being administered after retinoic acid. In yet another embodiment, the use combination comprises Bryostatin-1 and/or DCPLA methyl ester, and retinoic acid being administered at the same time but formulated into different compositions.

The present disclosure also relates to methods of treatment using at least one PKC activator or a combination thereof (i.e., a mixture, conjugate, or use combination). For example, the present disclosure provides a method for treating at least one neurodegenerative or neuroaffective disorder or condition comprising administering to a patient in need thereof at least one PKC activator or combination thereof. In one embodiment, the neurodegenerative disorder or condition is chosen from Alzheimer's disease and Parkinson's disease. In another embodiment, the at least one neurodegenerative disorder or condition is caused by exposure to at least one neurotoxic chemical. The at least one neurotoxic chemical may be, for example, a heavy metal. In another embodiment, the neuroaffective disorder or condition is chosen from depression, bipolar disorder, and schizophrenia. In still another embodiment, the present disclosure provides a method for treating ischemia and/or hypoxia as a result of open-heart surgery comprising administering to a patient in need thereof at least one PKC activator or combination thereof, with administration being before or after surgery.

The present disclosure further relates to methods for treating stroke comprising administering to a patient in need thereof at least one PKC activator or a combination thereof. The disclosure also relates to methods for treating brain trauma comprising administering to a patient in need thereof at least one PKC activator or a combination thereof. In one embodiment, the brain injury is chosen from traumatic brain injury and brain injury induced by irradiation.

A further aspect of the disclosure relates to methods of improving learning comprising administering to a patient in need thereof at least one PKC activator or a combination thereof. In another embodiment, the disclosure relates to methods of improving memory comprising administering to a patient in need thereof at least one PKC activator or a combination thereof.

The at least one PKC activator or combination of at least one PKC activator may be administered to a patient in need thereof by conventional methods such as oral, parenteral, transmucosal, intranasal, inhalation, or transdermal administration. Parenteral administration includes intravenous, intra-arteriolar, intramuscular, intradermal, subcutaneous, intraperitoneal, intraventricular, intrathecal, and intracranial administration.

The present disclosure relates to compositions comprising at least one protein kinase C activator or combinations thereof and a carrier. The present disclosure further relates to a composition of at least one protein kinase C activator and a carrier, and a composition of at least one combination and a carrier, wherein the two compositions are administered together to a patient in need thereof. In one embodiment, the composition of at least one protein kinase C activator may be administered before or after the administration of the composition of the combination to a patient in need thereof.

The formulations of the compositions described herein may be prepared by any suitable method known in the art. In general, such preparatory methods include bringing at least one of active ingredients into association with a carrier. If necessary or desirable, the resultant product can be shaped or packaged into a desired single- or multi-dose unit.

Although the descriptions of compositions provided herein are principally directed to compositions suitable for ethical administration to humans, it will be understood by a skilled artisan that such compositions are generally suitable for administration to animals of all sorts. Modification of pharmaceutical compositions suitable for administration to humans or to render the compositions suitable for administration to various animals is well understood, and the ordinarily skilled veterinary pharmacologist can design and perform such modification with merely ordinary, if any, experimentation. Subjects to which administration of the compositions of the disclosure is contemplated include, but are not limited to, humans and other primates, and other mammals.

As discussed herein, carriers include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other additional ingredients that may be included in the compositions of the disclosure are generally known in the art and may be described, for example, in *Remington's Pharmaceutical Sciences*, Genaro, ed., Mack Publishing Co., Easton, Pa., 1985, and *Remington's Pharmaceutical Sciences, 20$^{th}$ Ed.*, Mack Publishing Co. 2000, both incorporated by reference herein.

In one embodiment, the carrier is an aqueous or hydrophilic carrier. In a further embodiment, the carrier can be water, saline, or dimethylsulfoxide. In another embodiment, the carrier is a hydrophobic carrier. Hydrophobic carriers include inclusion complexes, dispersions (such as micelles, microemulsions, and emulsions), and liposomes. Exemplary hydrophobic carriers include inclusion complexes, micelles, and liposomes. See, e.g., Remington's: The Science and Practice of Pharmacy 20th ed., ed. Gennaro, Lippincott: Philadelphia, Pa. 2003, incorporated by reference herein. In addition, other compounds may be included either in the hydrophobic carrier or the solution, e.g., to stabilize the formulation.

The compositions disclosed herein may be administered to a patient in need thereof by any suitable route including oral, parenteral, transmucosal, intranasal, inhalation, or transdermal routes. Parenteral routes include intravenous, intra-arteriolar, intramuscular, intradermal, subcutaneous, intraperitoneal, intraventricular, intrathecal, and intracranial administration. A suitable route of administration may be chosen to permit crossing the blood-brain barrier. See e.g., *J. Lipid Res.* (2001) vol. 42, pp. 678-685, incorporated by reference herein.

In one embodiment, the compositions described herein may be formulated in oral dosage forms. For oral administration, the composition may take the form of a tablet or capsule prepared by conventional means with, for example, carriers such as binding agents (e.g., pregelatinized maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods generally known in the art.

In another embodiment, the compositions herein are formulated into a liquid preparation. Such preparations may take the form of, for example, solutions, syrups or suspensions, or they may be presented as a dry product for constitution with water or other suitable vehicle before use. Such liquid preparations may be prepared by conventional means with, for examples, pharmaceutically acceptable carriers such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl p-hydroxybenzoates, or sorbic acid). The preparations may also comprise buffer salts, flavoring, coloring, and sweetening agents as appropriate. In one embodiment, the liquid preparation is for oral administration.

In another embodiment of the present disclosure, the compositions herein may be formulated for parenteral administration such as bolus injection or continuous infusion. Formulations for injection may be presented in unit dosage form, e.g., in ampoules, or in multi-dose containers, with an added preservative. The compositions may take such forms as suspensions, solutions, dispersions, or emulsions in oily or aqueous vehicles, and may contain formulatory agents such as suspending, stabilizing, and/or dispersing agents.

In another embodiment, the compositions herein may be formulated as depot preparations. Such formulations may be administered by implantation (for example, subcutaneously or intramuscularly) or by intramuscular injection. For example, the compositions may be formulated with a suitable polymeric or hydrophobic material (for example, as an emulsion in an acceptable oil) or ion exchange resin, or as a sparingly soluble derivative, for example, as a sparingly soluble salt.

In another embodiment, at least one PKC activator or combination thereof is delivered in a vesicle, such as a micelle, liposome, or an artificial low-density lipoprotein (LDL) particle. See, e.g., U.S. Pat. No. 7,682,627.

In one embodiment, the at least one PKC activator or combination thereof is present in a composition in an amount effective for treating at least one neurodegenerative disorder or condition such as Alzheimer's disease and Parkinson's disease, treating stroke, treating brain injury such as traumatic brain injury and brain injury induced by irradiation, and treating at least one neuroaffective disorder or condition chosen from depression, bipolar disorder, or schizophrenia. In another embodiment, the at least one PKC activator or combination thereof is present in a composition in an amount effective for improving learning and improving memory.

In a further embodiment, the doses for administration to a patient in need thereof may suitably be prepared so as to deliver from about 1 mg to about 10 g, such as from about 5 mg to about 5 g, from about 50 mg to about 2 g, from about 100 mg to about 1.5 g, from about 150 mg to about 1 g, or from about 250 mg to about 500 mg of at least one PKC activator or combination thereof.

In one embodiment, at least one PKC activator or combination thereof may be present in the composition in an amount ranging from about 0.01% to about 100%, from about 0.1% to about 90%, from about 0.1% to about 60%, from about 0.1% to about 30% by weight, or from about 1% to about 10% by weight of the final formulation. In another embodiment, at least one PKC activator or combination thereof may be present in the composition in an amount ranging from about 0.01% to about 100%, from about 0.1% to about 95%, from about 1% to about 90%, from about 5% to about 85%, from about 10% to about 80%, and from about 25% to about 75%.

The present disclosure relates to kits that may be utilized for administering to a subject at least one PKC activator or combination thereof separately or combined in a single composition.

The kits may comprise devices for storage and/or administration. For example, the kits may comprise syringe(s), needle(s), needle-less injection device(s), sterile pad(s), swab(s), vial(s), ampoule(s), cartridge(s), bottle(s), and the like. The storage and/or administration devices may be graduated to allow, for example, measuring volumes. In one embodiment, the kit comprises at least one PKC activator in a container separate from other components in the system. In another embodiment, the kit comprises a means to combine at least one PKC activator and at least one combination separately. In yet another embodiment, the kit comprises a container comprising at least one PKC activator and a combination thereof.

The kits may also comprise one or more anesthetics, such as local anesthetics. In one embodiment, the anesthetics are in a ready-to-use formulation, for example an injectable formulation (optionally in one or more pre-loaded syringes), or a formulation that may be applied topically. Topical formulations of anesthetics may be in the form of an anesthetic applied to a pad, swab, towelette, disposable napkin, cloth, patch, bandage, gauze, cotton ball, Q-tip™, ointment, cream, gel, paste, liquid, or any other topically applied formulation. Anesthetics for use with the present disclosure may include, but are not limited to lidocaine, marcaine, cocaine, and xylocaine.

The kits may also contain instructions relating to the use of at least one PKC activator or a combination thereof. In another embodiment, the kit may contain instructions relating to procedures for mixing, diluting, or preparing formulations of at least one PKC activator or a combination thereof. The instructions may also contain directions for properly diluting a formulation of at least one PKC activator or a combination thereof in order to obtain a desired pH or range of pHs and/or a desired specific activity and/or protein concentration after mixing but prior to administration. The instructions may also contain dosing information. The instructions may also contain material directed to methods for selecting subjects for treatment with at least one PKC activator or a combination thereof.

The present disclosure relates to diagnostic methods and/or uses of at least one PKC activator and at least one retinoid. For example, the present disclosure provides methods for screening at least one drug comprising: adding at least one retinoid and at least one PKC activator to cells; allowing a synaptic network to form; adding at least one toxin that disrupts synaptic networks; adding at least one drug to be screened; and determining whether the synaptic network has been at least partially restored or whether any synaptogenesis has occurred. In one embodiment, the screening is used to determine whether the drug is able to at least partially restore synaptic networks, is able to induce synaptogenesis, and/or is able to prevent the destruction of synaptic networks.

In one embodiment, the at least one PKC activator is chosen from cyclopropanated polyunsaturated fatty acids, cyclopropanated monounsaturated fatty acids, cyclopropanated polyunsaturated fatty alcohols, cyclopropanated monounsaturated fatty alcohols, cyclopropanated polyunsaturated fatty acid esters, cyclopropanated monounsaturated fatty acid esters, cyclopropanated polyunsaturated fatty acid sulfates, cyclopropanated monounsaturated fatty acid sulfates, cyclopropanated polyunsaturated fatty acid phosphates, cyclopropanated monounsaturated fatty acid phosphates, macrocyclic lactones, DAG derivatives, isoprenoids, octylindolactam V, gnidimacrin, iripallidal, ingenol, napthalenesulfonamides, diacylglycerol kinase inhibitors, fibroblast growth factor 18 (FGF-18), insulin growth factor, hormones, growth factor activators, cyclopropanated polyunsaturated fatty acid conjugates, cyclopropanated monounsaturated fatty acid conjugates, bryostatin conjugates, bryolog conjugates, and retinoic acid conjugates. In another embodiment, the at least one PKC activator is chosen from Bryostatin-1 and DCPLA-ME.

In another embodiment, the at least one retinoid and at least one PKC activator are added to the cells separately. In one embodiment, the at least one retinoid may be added to the cells before the addition of the at least one PKC activator. Alternatively, the at least one retinoid may be added to the cells after the addition of at least one PKC activator. In one embodiment, the at least one retinoid and the at least one PKC activator are added simultaneously.

In one embodiment, the present disclosure relates to diagnostic kits comprising at least one PKC activator and at least one retinoid. The PKC activator(s) and retinoid(s) may be provided in various forms including, for example, ethanol or detergent solutions, or for example, provided as an emulsion. The kits may include items chosen from cells, tissue culture plate(es), cell medium(s), stain(s) for viewing the cells, and toxin(s). The kit may further include instructions for use.

The present disclosure further relates to diagnostic methods and/or uses of at least one selective PKC activator or mixtures or conjugates thereof. For example, the present disclosure provides methods for screening at least one drug comprising: adding at least one selective PKC activator or mixtures or conjugates thereof to cells; allowing a synaptic network to form; adding at least one toxin that disrupts synaptic networks; adding at least one drug to be screened; and determining whether the synaptic network has been at least partially restored or whether any synaptogenesis has occurred. In one embodiment, the screening is used to determine whether the drug is able to at least partially restore synaptic networks, is able to induce synaptogenesis, and/or is able to prevent the destruction of synaptic networks. In one embodiment, the selective PKC activator is a cyclopropanated PUFA or alcohol or ester thereof, a cyclopropanated MUFA or alcohol or ester thereof. In one embodiment, the selective PKC activator is chosen from DCPLA methyl ester and DHA-CP6 methyl ester.

In another embodiment, a mixture of at least one selective PKC activator is chosen from DCPLA and retinoic acid, and DHA-CP6 and retinoic acid. In yet another embodiment, a conjugate of the at least one selective PKC activator is chosen from DCPLA-cholesteryl ester or DHA-CP6-cholesteryl ester.

In another embodiment, the present disclosure further relates to diagnostic kits comprising at least one PKC activator or mixtures or conjugates thereof. The PKC activator or mixtures or conjugates thereof may be provided in various forms including, for example, ethanol or detergent solution, or for example, provided as an emulsion. The kits may include items chosen from cells, a tissue culture plate(es), cell medium(s), stain(s) for viewing the cells, and toxin(s). The kit may further include instructions for use.

In one embodiment, the diagnostic methods comprise the use of a tissue culture plate. For example, cells may be cultured on a tissue culture plate or flask in a medium that is appropriate for the cell type, for example neurobasal medium for neurons, MEM/F12 for neuroblastoma cells, or DMEM containing suitable additives or serum for other types of cells. For example, Eagle's medium can be used. In another embodiment, the cells can be human SH-SY5Y neuroblastoma cells or primary neurons.

In one embodiment, the at least one toxin that disrupts the synaptic network is chosen from β-amyloids, ADDLs, and ASPDs. β-amyloid ("Aβ"), a 4 kDa peptide produced by the proteolytic cleavage of amyloid precursor protein ("APP") by β- and γ-secretases. Oligomers of Aβ are considered to be most toxic. Aβ derived diffusible ligands (ADDLs) are also toxic. ADDLs can be produced following previously disclosed methods. See Lambert, M. P et al., *Proc. Natl. Acad. Sci. USA*, 1998, 95: 6448-6453. Amylospheroids (ASPDs) have been shown to be even more toxic than ADDLs. ASPDs can be produced following known methods. See Hoshi, M., et al. (2003) *Proc Natl Acad Sci USA* 100, 6370-6375, and Noguchi, A., et al. (2009) *J Biol Chem* 284, 32895-32905

In another embodiment, the at least one toxin that disrupts synaptic networks is chosen from taipoxin, okadaic acid, pertussis toxin, and botulinum toxin. In another embodiment, the at least one toxin can be a disease in the cells.

In yet another embodiment, the efficacy of the test drug compound may be determined using electron microscopy. Further evidence of efficacy of the test drug compound may be confocal microscopy, electron microscopy, and electrophysiological recordings.

EXAMPLES

The PKC activators and conjugates above, if not commercially available, may be prepared by methods known to those skilled in the art. For example, Bryostatin-1 can be isolated from natural sources or prepared according to published methods. See, e.g., Keck et al., (2011) *J. Am. Chem. Soc.* 133(4): 744-747. In another example, Bryostatin-16 can be prepared using atom-economical and chemoselective approaches. See, e.g., Trost et al., (2008) *Nature* 456: 485-488. Moreover, bryostatin can be produced by bacteria hosted by bryophytes.

PUFAs and MUFAs are generally commercially available and cyclopropanation of these compounds is known in the art. See, e.g., Nelson et al. (2009) *J Biol Chem* 274, 34514-34521. Esters can be prepared as known in the art—e.g., through esterification of an alcohol and a carboxylic acid. For alcohols that are unstable in acid (e.g., retinol, bryostatin), enzymes can be used to perform the esterification.

The PKC activator mixtures can also be prepared using known methods. For example, LDL mixtures can be prepared according to procedures in U.S. Pat. Nos. 7,576,055 and 7,803,400.

All numbers used in herein are to be understood as being modified in all instances by the term "about."

General Procedures:

Materials—

Cell culture media were obtained from Invitrogen, USA (F12K, Neurobasal, and B27) and K.D. Medical, USA (MEM). Bryostatin-1 was purchased from Biomol International, USA. All-trans retinoic acid ("RA") and other reagents were purchased from Sigma-Aldrich. $A\beta_{1-42}$ was purchased from Anaspec (San Jose, Calif.). Primary antibodies (PKC-ε, PKC-α, PKC-β, PKC-δ, β-actin, RACK1, synaptophysin, and PSD-95) were obtained from Santa Cruz Biotechnology, Inc, USA. β-Tubulin III, Synapsin-1, and Neurologin-1 were purchased from Millipore, USA. All secondary antibodies were purchased from Jackson laboratories, USA.

Cell Culture and Treatments—

Human SH-SY5Y neuroblastoma cells (ATCC) were cultured in 45% F12K, 45% minimum Eagle's medium, 10% fetal calf serum. Cells were incubated with 0.27 nM Bryostatin-1 for 0, 5, 15, 30, and 60 min to study isoform specific PKC activation. For differentiation of SH-SY5Y cells were maintained at 2% serum and treated with 10 μM RA for 72 hr. Thereafter, the cells were treated with 0.27 nM Bryostatin-1 in all following experiments. Medium was changed every 3 days with fresh supplementation of RA. Rat hippocampal neurons from 18-day-old embryonic Sprague-Dawley rat brains were plated on 24-well plates coated with poly-D-lysine (Sigma-Aldrich) in neurobasal medium supplemented with B-27 containing 0.5 mM glutamine and 25 μM glutamate (Invitrogen). The neuronal cells were grown under 5% $CO_2$ for 14 days in an incubator maintained at 37° C.

Amylospheroids ("ASPDs") were prepared following Noguchi et al. (2009) *J Biol Chem* 284, 32895-32905. See also Hoshi et al. (2003) *Proc Natl Acad Sci USA* 100, 6370-6375. Briefly, $A\beta_{1-42}$ was dissolved in 1,1,1,3,3,3-hexafluoro-2-propanol and incubated overnight at 4° C. and then for 3 hr at 37° C. The dissolved $A\beta_{1-42}$ was then lyophilized at 40 nmol/tube concentration. For preparing the ASPDs, the lyophilized $A\beta_{1-42}$ was dissolved in phosphate buffered saline (PBS) without $Ca^{2+}$ or $Mg^{2+}$ at less than 50 μM concentration and rotated for 14 hr at 4° C. After incubation, the Aβ solution was purified using a 100 kDa molecular mass cutoff filter (Amicon Ultra, Millipore) and the high-molecular weight fraction was saved to obtain the most toxic ASPDs. Aβ derived diffusible ligands ("ADDLs") were produced as previously described. See Lambert, M. P et al., *Proc. Natl. Acad. Sci. USA,* 1998, 95: 6448-6453. Briefly, $A\beta_{1-42}$ was solubilized at 5 mM in dimethyl sulfoxide, diluted to 100 μM in F12k medium, and incubated at 4° C. for 24 hr. The solution was centrifuged at 14000×g for 10 min at 4° C. and the supernatant was used as the ADDLs.

Size-Exclusion Chromatography (SEC)—

The prepared ASPDs and ADDLs were separated by SEC to estimate the molecular weight of the assemblies. SEC was performed using a HPLC (Shimadzu) connected with TSK-gel Super SW2000 column (Supelco). Molecular weight calibration was conducted using both high and low molecular weight proteins. Aβ assemblies were separated with buffer containing 0.1 M $Na_2PO_4$ and 0.1 M $Na_2SO_4$ adjusted to pH 6.65 with $H_3PO_4$ at 0.1 ml/min, with absorbance being monitored at 280 nm.

Cell Lysis and Western Blot Analysis—

Cells were harvested in homogenizing buffer containing 10 mM Tris-Cl (pH 7.4), 1 mM PMSF (phenylmethylsulfonyl fluoride), 1 mM EGTA, 1 mM EDTA, 50 mM NaF, and 20 μM leupeptin and were lysed by sonication. The homogenate was centrifuged at 100,000×g for 15 min at 4° C. to obtain the cytosolic fraction (supernatant) and membrane (pellet). The pellet was resuspended in the homogenizing buffer by sonication. Protein concentration was measured using the Coomassie Plus (Bradford) Protein Assay kit (Pierce, USA). Following quantification, 20 μg of protein from each sample was subjected to SDS-PAGE analysis in 4-20% gradient Tris-Glycine gel (Invitrogen, USA). The separated protein was then transferred to nitrocellulose membrane. The membrane was blocked with BSA at room temperature for 15 min and was incubated with primary antibody over night at 4° C. After the incubation, it was washed three times with TBS-T (Tris Buffered saline-Tween 20) and further incubated with alkaline phosphatase conjugated secondary antibody (Jackson Immunoresearch Laboratories, USA) at 1:10,000 dilution for 45 min. The membrane was finally washed three times with TBS-T and developed using the 1-step NBT-BCIP substrate (Pierce, USA). Western Blot was imaged in the ImageQuant RT-ECL (GE Life Sciences, Piscataway, N.J.) and densitometric quantification was performed using the IMAL software (Blanchette Rockefeller Neurosciences Institute, Morgantown, W. Va.). For translocation assays, PKC activation was represented as the percentage of total protein in the membrane (membrane/cytosol+membrane).

Immunofluorescence and Confocal Microscopy—

Cells were grown in two chambered slides (Nunc, USA) at low density. For immunofluorescence staining, the cells were washed with PBS (pH 7.4) and fixed with 4% paraformaldehyde for 4 min. Following fixation, the cells were blocked and permeabilized with 5% serum and 0.3% Triton X 100 in 1×PBS for 30 min. The cells were washed three times with 1×PBS and incubated with primary antibodies for 1 hr at 1:100 dilution. The incubation slides were then washed again three times in 1×PBS and were incubated with the FITC anti-rabbit IgG and Rhodamine anti-mouse IgG for 1 hr at 1:400 dilution. The cells were further washed and treated with DAPI (4',6-diamidino-2'-phenylindole, dihydrochloride) (Thermo Scientific, USA) to stain the nucleus. Finally, the slides were washed and mounted in Pro Long Gold antifade mounting solution (Invitrogen, USA) and were viewed under the LSM 710 Meta confocal microscope (Zeiss) at 350 nm, 490 nm, and 540 nm excitation and 470 nm, 525 nm, and 625 nm emission for DAPI, FITC, and Rhodamine respectively. Six individual fields at 63× oil lens magnification were analyzed for the mean fluorescence intensity (MFI) in each channel. The co-localization correlation generated by the ZEN software (Zeiss).

Coimmunoprecipitation—

Coimmunoprecipitation was done following protocol described Besson et al. with slight modification. See Besson et al. (2002) *J Biol Chem* 277, 22073-22084. Following treatment with Bryostatin-1, the cells were washed three times with 1×PBS and were incubated with 25 mM dithiobis [succinimidylpropionate] (DSP) for 30 min at room temperature to crosslink the intracellular proteins following the manufacturer's protocol. After crosslinking the proteins, the cells were lysed in the homogenizing buffer mentioned above. For immunoprecipitation, 500 µg of protein was incubated with 4 µg of appropriate antibody and 25 µl of Protein-A Sepharose beads (Invitrogen, USA) for 3 hr at 4° C. Immunoprecipitates were rinsed three times in the homogenizing buffer and were subjected to Western blot as described earlier.

Reverse Transcription Polymerase Chain Reaction (RT-PCR)—

RNA was isolated from the cells using Trizol reagent (Invitrogen, USA) following the manufacturer's protocol. Briefly, 5 µg of total RNA was reverse transcribed using oligo (dT) and Superscript III (Invitrogen, USA) at 50° C. for 1 hr. Two µl of the cDNA product was amplified using primers for PKC-ε (Forward Primer—AGCCTCGT-TCACGGTTCTATGC, Reverse primer—GCAGTGACCT-TCTGCATCCAGA), and β-tubulin (Forward Primer—TTGGGAGGTGATCAGCGATGAG, Reverse primer—CTCCAGATCCACGAGCACGGC) (Origene, Rockville, Md.) for 25 cycles following standard PCR protocols and 55° C. annealing temperature. The PCR amplicons were analyzed in an E-Gel (Invitrogen, USA). The gel image was documented using a Fuji Image gel scanner (FLA-9000, Fuji Film) and densitometric quantification was performed using the IMAL software (Blanchette Rockefeller Neurosciences Institute, Morgantown, W. Va.). Data were represented as normalized ratio of PKC-ε OD (Optical Density) against β-tubulin OD for three independent experiments.

PKC Assay—

To measure PKC activity, 10 µg of protein from either cytosol or membrane was incubated for 15 min at 37° C. in the presence of 10 µM histones, 4.89 mM $CaCl_2$, 1.2 µg/µl phosphatidyl-L-serine, 0.18 µg/µl 1,2-dioctanoyl-sn-glycerol, 10 mM $MgCl_2$, 20 mM HEPES (pH 7.4), 0.8 mM EDTA, 4 mM EGTA, 4% glycerol, 8 µg/ml aprotinin, 8 µg/ml leupeptin, 2 mM benzamidine, and 0.5 µCi of [γ-$^{32}$P] ATP. [$^{32}$P]Phosphoprotein formation was measured by adsorption onto phosphocellulose as described previously. See Nelson et al. (2009) *J Biol Chem* 284, 34514-34521. For measurements of activation by RA, PKC activity was measured in the absence of diacylglycerol (DAG) and phosphatidylserine, as described by Nelson et al. (2009) *J Biol Chem* 284, 34514-34521. PKC-δ and PKC-ε were measured in the absence of added EGTA and $CaCl^2$, as described by Kanno et al. (2006) *J Lipid Res* 47, 1146-1156. The enzyme was provided as a purified isozyme for in vitro experiments.

Synaptosome Preparation—

Synaptosomes from undifferentiated and differentiated cells were prepared following the method described earlier (29). See Nagy et al. (1984) *J Neurochem* 43, 1114-1123. Briefly, the cells were washes in 1×PBS and homogenized in 10 volumes of buffer ("buffer1") containing 0.32 M sucrose, 5 mM HEPES pH 7.2, and 0.1 mM EDTA in a Teflon homogenizer. The homogenate was centrifuged at 1000×g for 10 min to remove the nuclear fraction. The supernatant obtained was again spun at 12000×g for 20 min at 4° C. The pellet thus obtained was resuspended in 3 volumes of buffer1 and was layered on to the 16%/10%/8.5% Percoll gradient prepared from the stock isoosmotic percoll containing 9 parts 100% percoll, and 1 part 2.5 M sucrose. The preparation was centrifuged at 15000×g for 20 min at 4° C. Synaptosomes collected from the layer between 10% and 16% gradient was washed with 1×PBS and was centrifuged at 20000×g for 15 min. The purified synaptosomes were homogenized in homogenizing buffer and were subjected to western blot as described before.

Viability Assay—

Viability of cells was measured by MTT assay. MTT (3-(4,5-Dimethylthiazol-2-yl)-2,5-diphenyltetrazolium bromide) is a tetrazolium salt that is cleaved to formazan by the succinate dehydrogenase, which is only active in viable cells. After solubilization of the formazan, the amount of dye can be quantified with a microplate reader at 570 nm along with a reference of 630 nm. For MTT assay, 5×10$^4$ primary rat hippocampal neurons from 18-day-old embryonic Sprague-Dawley rat brains were plated on each well of 24-well plates coated with poly-D-lysine. After treatment, the cells were washed with 1×PBS and were incubated with 200 µl of 1 mg/ml MTT solution (Sigma, USA) at 37° C. for 2 hr. Then the MTT-solution was removed and the cells were lysed with 200 µl isopropanol containing 0.04 M HCl and 160 mM NaOH for 10 min. Finally, the reading was done at 570 nm and 630 nm. All the samples were done in triplicates and the data was represented as the percentage of control.

Statistical Analysis—

All the experiments were performed in triplicates or more. Data are represented as mean±SE. Statistical analysis was performed by Student's t-test using GraphPad Prism 5 software with $p<0.05$ considered statistically significant.

Synthesis of DCPLA and DCPLA-ME:

DCP-LA and DCPLA-ME (i.e., methyl 8-(2-((2-pentyl-cyclopropyl)methyl)cyclopropyl)octanoate) was synthesized following an earlier described method. See Nelson et al. (2009) *J Biol Chem* 274, 34514-34521. Briefly, linoleic acid methyl ester (commercially available) was cyclopropanated using the modified Simmons-Smith reaction using chloroiodomethane and diethylzinc. See Tanaka et al. (2003) *Bioorg Med Chem Lett,* 13: 1037-1040; Furukawa et al. (1967) *Tetrahedron,* 24: 53-58; and Denmark et al. (1991) *J Org Chem,* 56: 6974-6981.

All apparatus was baked at 60° C. for 1 hr and flame-dried while passing dry nitrogen through the apparatus. A 100-ml three-neck round-bottom flask with a stirring bar and a temperature probe was surrounded by a dry ice mixture and filled with 1.25 g (4.24 mmol) of linoleic acid methyl ester in 25 ml of dichloromethane and bubbled with $N_2$. A 1 M solution of diethylzinc (51 ml, 54.94 mmol) in hexane was added anaerobically using a 24-inch-long 20-gauge needle, and the solution was cooled to −5° C. Chloroiodomethane ($ClCH_2I$, 8.02 ml, 109.88 mmol) was added dropwise, 1 drop/s, with constant stirring. The rate of addition was decreased if necessary to maintain the reaction mixture below 2° C. The reaction mixture became cloudy during the reaction, and an insoluble white zinc product was produced. The flask was sealed, and the mixture was allowed to react further for 1 hr and then allowed to come to room temperature gradually over 2 hr.

To prevent the formation of an explosive residue in the hood, diethylzinc was not evaporated off. The mixture was poured slowly into 100 ml of water under stirring to decompose any excess diethylzinc. Ethane was evolved. The mixture was centrifuged at 5000 rpm in glass centrifuge tubes, and the upper aqueous layer was discarded. The white precipitate was extracted with $CH_2Cl_2$ and combined with the organic phase. The organic phase was washed with water and centrifuged. The product was analyzed by Silica Gel G TLC using hexane +1% ethyl acetate and purified by chromatography on silica gel using increasing concentrations of 1-10% ethyl acetate in n-hexane and evaporated under nitrogen, leaving the DCPLA-ME as a colorless oil. The Simmons-Smith reaction preserved the stereochemistry of the starting materials.

To obtain DCPLA, 0.15 g of DCPLA-ME was dissolved in 1 ml of 1 N LiOH and 1 ml of dioxane. Dioxane and methanol were added until it became homogeneous, and the solution was stirred 60° C. overnight to 3 days. The product was extracted in $CH_2Cl_2$ and centrifuged. The aqueous layer and white interface were reextracted with water and washed until the white layer no longer formed. The product was evaporated under $N_2$ and purified by chromatography on silica gel. The product, a colorless oil, eluted in 20% EtOAc in n-hexane. Its purity was checked by TLC in 10% EtOAc/hexane and by C18 reversed phase HPLC with UV detection at 205 nm, using 95% acetonitrile as the mobile phase.

Synthesis of $H^3$-DCPLA-ME:

Methylation of 3H-Linoleic acid: Linoleic acid[9,10,12,13]$^3$H (120 Ci/mmol) was evaporated to dryness in a 2 ml ReactiVial. Thionyl chloride (0.5 ml) was immediately added and the sealed vial was incubated at 60° C. overnight. Methanol (1 ml) was added and the mixture was evaporated and dissolved in dichloromethane.

Cyclopropanation:

Simmons-Smith cyclopropanation was carried out using $ClCH_2I$ as described above and the DCPLA-ME product was extracted into $CH_2Cl_2$ and purified by column chromatography. The radioactive lipid fractions were combined, evaporated, and stored in 100 µl EtOH to prevent radioactive decomposition.

Column Chromatography:

A glass column (22 mm i.d.×200 mm long or 36 mm i.d.×200 mm long) with a coarse frit was filled with silica gel 130-270 mesh, 60 Angstrom, pore volume 0.74 $cm^3$/g. The sample was applied and washed with 50 ml hexane. The product was eluted by sequential addition of 50 ml solvent of gradually increasing polarity (hexane, followed by increasing concentrations of ethyl acetate in hexane, then ethanol). Fractions containing product were evaporated under nitrogen.

Thin-Layer Chromatography:

TLC was performed on 5×20 cm silica gel G TLC plates containing fluorescent indicator. Solvents were hexane+1% ethyl acetate. Detection was by UV absorbance, colorimetric detection with $I_2$ and charring (spraying with 10% $H_2SO_4$ followed by heat).

Synthesis of DHA-CP6:

3-(2-((2-((2-(2-((2-((2-ethyl-cyclopropyl)methyl)-cyclopropyl)methyl)cyclopropyl)methyl)cyclopropyl)methyl)cyclopropyl)methyl)cyclopropyl)propanoic acid ("DHA-CP6") was prepared according to the procedures above for preparing DCPLA except that docosahexaenoic acid methyl ester (commercially available) was used in place of the linoleic acid methyl ester. See Nelson et al., *J. Biol. Chem.*, 2009, 274, 34514-34521.

Synthesis of DCPLA-Ethyl Ester:

Methyl linoleate (2 g) was incubated with anhydrous ethanol (20 ml), KOH (0.2 g), and 4 g of molecular sieves for 20 minutes at 60° C. with stirring. The reaction mixture was neutralized acetic acid and the ethyl linoleate product was extracted with ethyl acetate. Ethyl linoleate was cyclopropanated as described above using the Simmons-Smith reaction to produce DCPLA-ethyl ester. All reactions were carried out under a nitrogen atmosphere Synthesis of DCPLA-Isopropyl Ester:

Isopropyl linoleate (commercially available) was prepared by refluxing methyl linoleate (3 g) with isopropanol (20 ml) and lithium hydroxide (1 g) for 2 hours in a 50 ml round bottom flask with condenser. The product was purified by flash chromatography. The resultant isopropyl linoleate was then subject to the Simmons-Smith reaction described above to generate the DCPLA-isopropyl ester.

Alternative Synthesis of DCPLA-Isopropyl Ester:

Methyl linoleate (2 g) was transesterified by reacting with isopropanol (20 ml) and KOH (0.2 g) over 4 g molecular sieves at 60° C. in a sealed bottle under a nitrogen atmosphere. After 20 minutes, the mixture was neutralized with acetic acid and isopropyl linoleate product was extracted into ethyl acetate. The resultant isopropyl linoleate was then subjected to the Simmons-Smith reaction described above to produce DCPLA-isopropyl ester Synthesis of DCPLA-Tert-Butyl Ester:

DCPLA (100 mg) and N,N-dimethylformamide di-tert-butyl acetal (0.25 ml) were incubated with toluene (0.4 ml) at 60° C. for several days. The resultant DCPLA-tert-butyl ester was extracted with hexane and purified by flash chromatography (10% EtOAc/hexane).

Synthesis of DCPLA-Cyclopropanated Oleyl Ester:

Oleyl linoleate was prepared by refluxing linoleic acid (1 g) and oleyl alcohol (1 ml) in $CH_2Cl_2$ (20 ml) and concentrated $H_2SO_4$ (10 µl) overnight. The product was slightly pink and was purified by flash chromatography. The resultant oleyl linoleate was subjected to the Simmons-Smith procedure described above to generate DCPLA-oleyl ester.

Synthesis of DCPLA-Retinyl Ester:

DCPLA-ME (50 mg) and retinol (50 mg) were evaporated to dryness. Hexane (1 ml) was added along with lipase acrylic beads from *Candida antarctica* (0.2 g), and the mixture was incubated overnight at 60° C., protected from light. The product was purified by thin layer chromatography using 50 hexane: 5 ethyl acetate: 5 acetone.

Synthesis of DCPLA-Cholesteryl Ester and Cholesteryl Linoleate:

DCPLA (1 g), cholesterol (1 g), $CH_2Cl_2$ (20 ml), and concentrated $H_2SO_4$ (1 µl) were combined and refluxed overnight. The product was washed with sodium phosphate (pH 7.0, 5 ml) and purified by flash chromatography to yield the DCPLA-cholesteryl ester. Linoleic acid (1 g), cholesterol (1 g), $CH_2Cl_2$ (20 ml), and concentrated $H_2SO_4$ (20 µl) were combined and refluxed overnight. The product was washed with sodium phosphate (pH 7.0, 5 ml) and purified by flash chromatography to yield the cholesteryl linoleate.

Alternative Synthesis of DCPLA-Cholesteryl Ester:

DCPLA-ME (0.1 g), cholesterol (0.1 g), hexane (10 ml), and *Candida antarctica* lipase acrylic beads (1 g) can be combined and incubated at 60° C. overnight. The produce can be washed with sodium phosphate (pH 7.0, 5 ml) and can be purified by flash chromatography to yield DCPLA-cholesteryl ester.

Synthesis of DCPLA-Bryostatin Ester:

DCPLA-ME (1 mg) and Bryostatin-1 (1 mg) can be evaporated to dryness. Hexane (1 ml) can be added along with lipase acrylic beads from *Candida antarctia* (0.2 g), and the mixture can be incubated overnight at 60° C. The product can be purified by flash chromatography.

Synthesis of ASPDs:

Amylospheroids (ASPDs) were prepared following Hoshi, M., et al. (2003) *Proc Natl Acad Sci USA* 100, 6370-6375, and Noguchi, A., et al. (2009) *J Biol Chem* 284, 32895-32905. Briefly, $A\beta_{1-42}$ was dissolved in 1,1,1,3,3,3-hexafluoro-2-propanol and incubated overnight at 4° C. and then 3 hr at 37° C. The dissolved $A\beta_{1-42}$ was then lyophilized in 1.5 ml polypropylene centrifuge tubes at 40 nmol/tube concentration. For preparing the ASPDs, the lyophilized $A\beta$ was dissolved in phosphate buffered saline (PBS) without $Ca^{2+}$ or $Mg^{2+}$ at less than 50 µM concentration and rotated for 14 hr at 4° C. After incubation, the $A\beta$ solution was purified using a 100 kDa molecular mass cutoff filter (Amicon Ultra, Millipore) and the high-molecular weight fraction was saved to obtain the most toxic ASPDs.

Example 1

DCPLA-ME Had a Less Inhibitory Effect on PKC-δ than DCPLA and DHA-CP6

(A) Measure of Total PKC Activity in Cultured Cells—

After removal of culture medium, cells were scraped in 0.2 ml homogenization buffer (20 mM Tris-HCl, pH 7.4, 50 mM NaF, 1 µg/ml leupeptin, and 0.1 mM PMSF) and immediately homogenized in the cell culture plate by sonication in a Marsonix microprobe sonicator (5 sec, 10 W). Aliquots were transferred immediately after sonication to 0.5 ml centrifuge tubes and frozen at −80°.

(B) Measure of PKC Activation—

To measure PKC, 10 µl of cell homogenate or purified PKC isoform was incubated for 15 min at 37° C. in the presence of 10 µM histones, 4.89 mM $CaCl_2$, 1.2 µg/µl phosphatidyl-L-serine, 0.18 µg/µl 1,2-dioctanoyl-sn-glycerol, 10 mM $MgCl_2$, 20 mM HEPES (pH 7.4), 0.8 mM EDTA, 4 mM EGTA, 4% glycerol, 8 µg/ml aprotinin, 8 µg/ml leupeptin, and 2 mM benzamidine. [γ32P]ATP (0.5 µCi) was added and 32P-phosphoprotein formation was measured by adsorption onto phosphocellulose as described previously. See Nelson et al., *J. Neurochemistry*, 1995, 65: 2350-2357.

(C) Measure of Activation of PKC Isozymes by PKC Activators—

PKC activity of each compound was measured in the absence of diacylglycerol and phosphatidylserine and PKC-δ and PKC-ε were measured in the absence of added EGTA and $CaCl_2$, as described by Kanno et al., *J. Lipid Res.*, 2006, 47: 1146-1156. Low concentrations of $Ca^{2+}$ were needed because high $Ca^{2+}$ can interact with the PKC phosphatidylserine binding site and prevents activation. Freeze-thawing of the samples more than once was avoided because it was found to greatly reduce the PKC activity and the degree of activation. To determine their PKC isoform specificity, the compounds were pre-incubated with purified isoforms of PKC for five minutes and the PKC activity was measured radiometrically.

Figure 1:
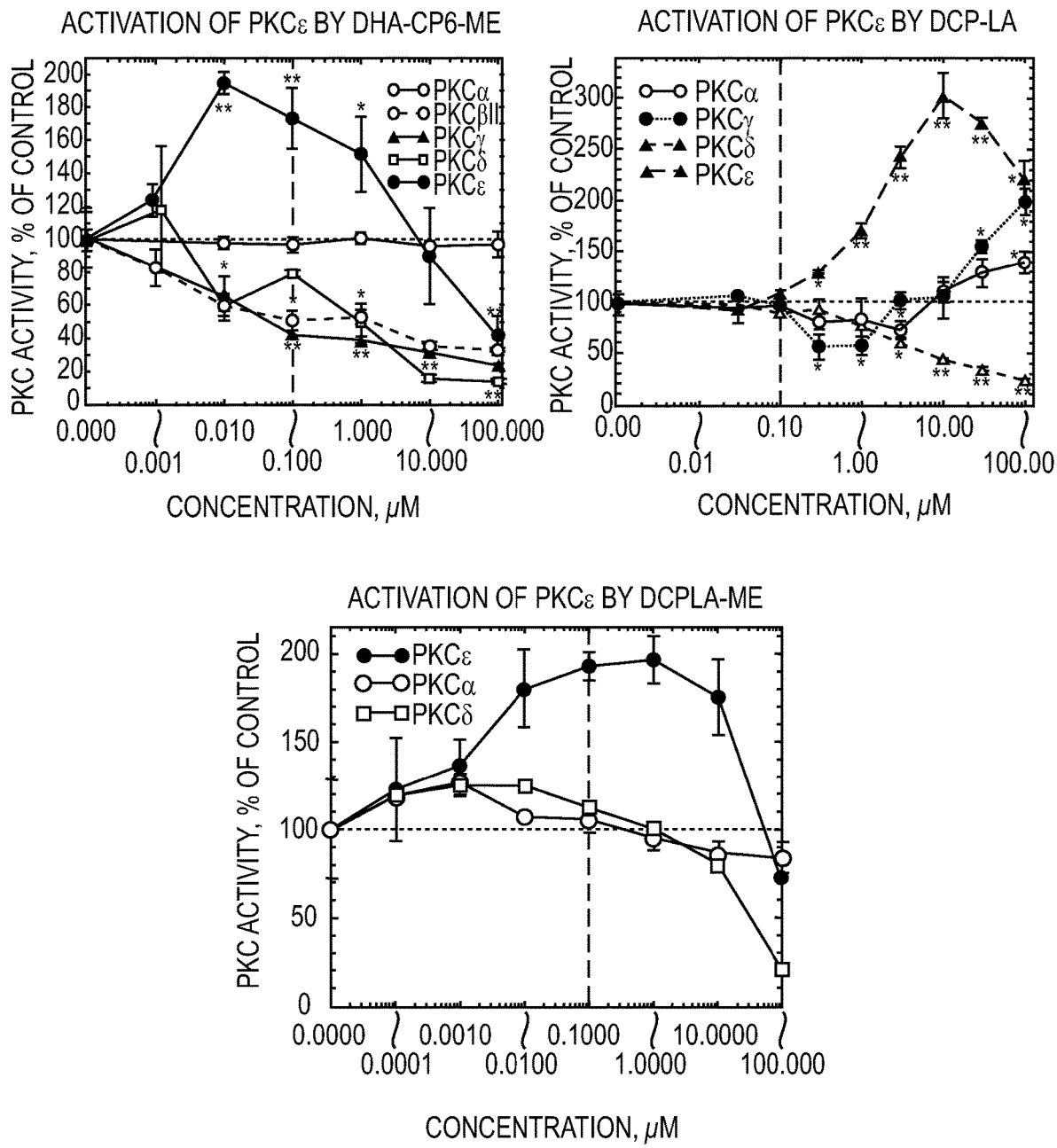
FIG. 1: PKC activation by DCPLA methyl ester ("DCPLA-ME") compared to DCPLA and DHA-CP6.

DCPLA-ME was found to activate PKC-ε (but not PKC-α or PKC-δ). FIG. 1 shows that DCPLA-ME produced maximal activity at 0.1 and 1 µM and is relatively specific for PKC-ε. Indeed, DCPLA-ME did not have a major effect on either PKC-α or PKC-δ at the same concentrations. DCPLA-ME activated PKC-ε by more than 50% in a range of 0.01-10 µM, with maximum activation at 100 nM and 1 µM concentrations. At its peak, DCPLA-ME activated PKC-ε up to 190% of control.

Further, DCPLA-ME had a less inhibitory effect on PKC-δ than DHA-CP6 and DCPLA This may be an important advantage because downregulation of PKC-δ by PKC activators that bind to the diacylglycerol site (such as phorbol ester) may result in tumor-promoting effects. Further, because PKC-ε and PKC-δ generally have antagonistic effects, inhibition of PKC-δ may be desirable because it may contribute to the efficacy of the drug. In general, PKC-ε and PKC-δ have antagonistic activities in many pathways. As such, it may be desirable to activate PKC-ε while minimizing activation and downregulation of PKC-δ.

Example 2

Figure 2:
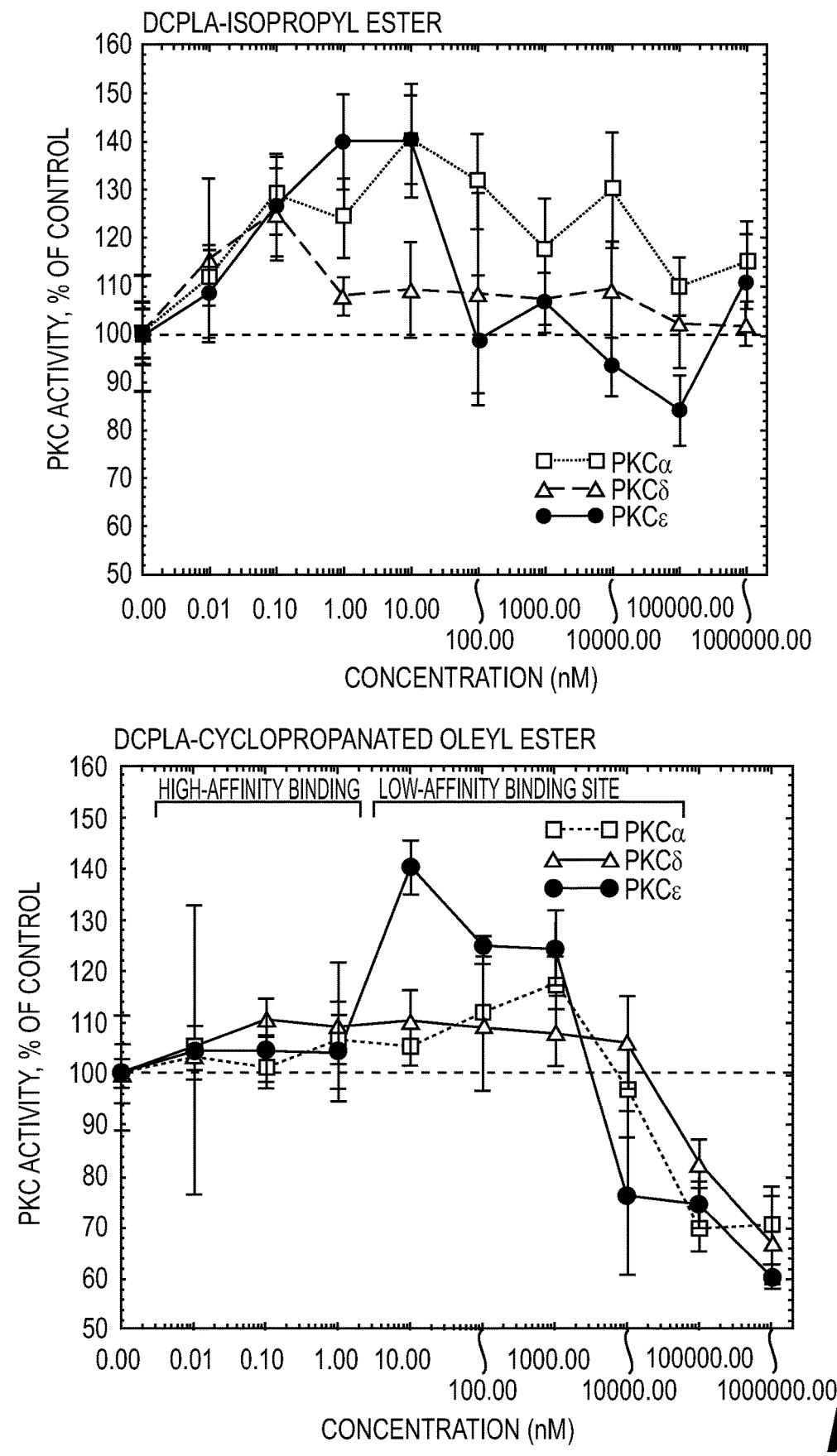
FIG. 2: PKC activation and selectivity of DCPLA-isopropyl ester and DCPLA-cyclopropanated oleyl ester.

PKC Activation by DCPLA-Isopropyl Ester and DCPLA-Cyclopropanated Oleyl Ester Following the procedure in Example 1, the activation and PKC isoform specificity of DCPLA-isopropyl ester and DCPLA-cyclopropanated oleyl ester were measured (FIG. 2). DCPLA-isopropyl ester activated both PKC-α and PKC-ε up to 40% of control and only slightly activated PKC-δ. Maximal activation was seen at 10 nM. DCPLA-cyclopropanated oleyl ester was found to be relatively specific for PKC-ε, exhibiting activation 140% of control. Maximal activation was seen at 10 nM.

Example 3

Figure 3:
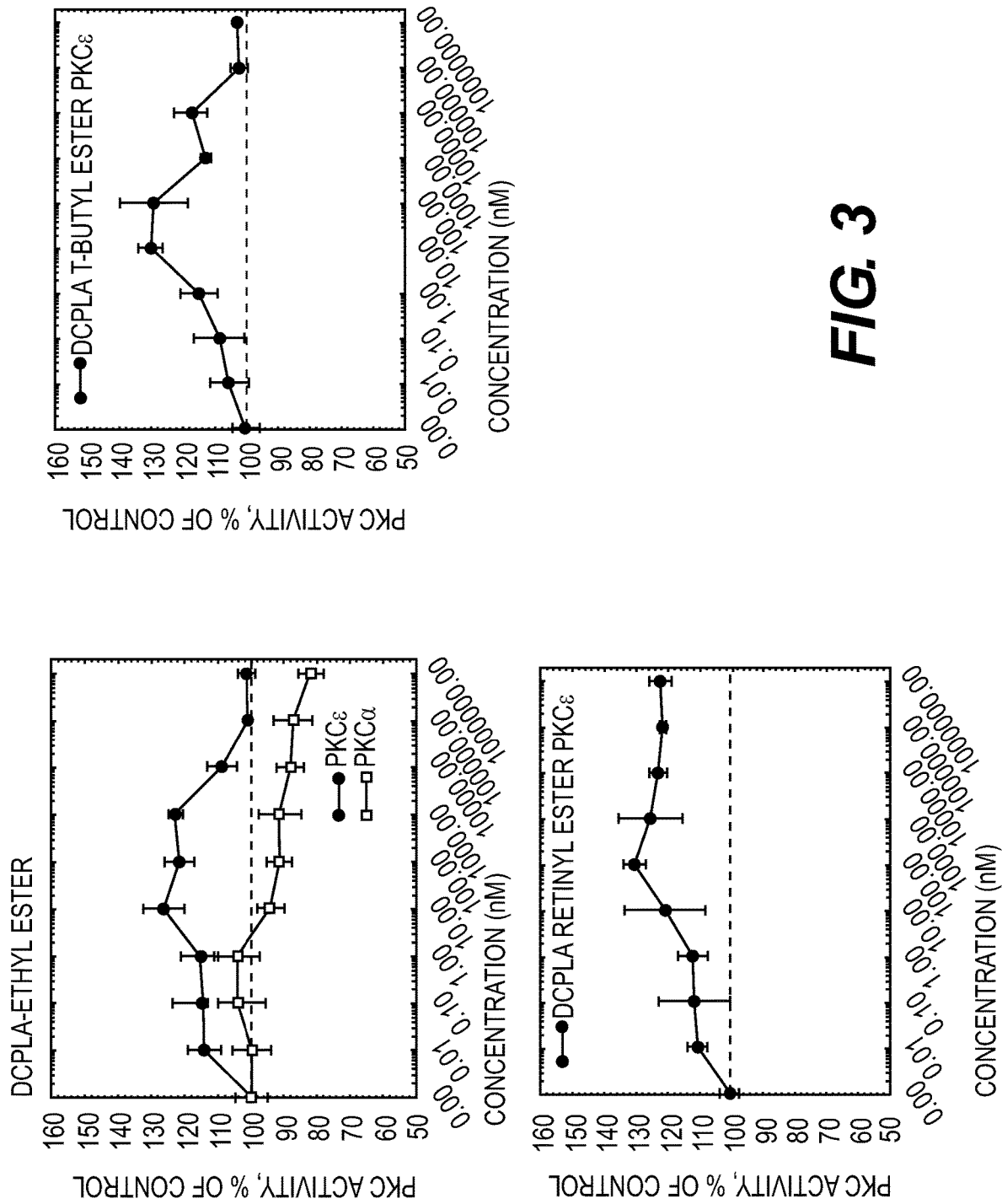
FIG. 3: PKC activation and selectivity of DCPLA-ethyl ester, DCPLA-tert-butyl ester, and DCPLA retinyl ester.

PKC Activation by DCPLA-Ethyl Ester, DCPLA-Tert-Butyl Ester, and DCPLA-Retinyl Ester The activation and PKC isozyme specificity of DCPLA-ethyl ester was measured following the procedures in Example 1(B) and (C), except that 9 ng of the purified isozyme was used and it was pre-incubated for 5 minutes at room temperature (FIG. 3). PKC-ε activation by DCPLA-tert-butyl ester and DCPLA-retinyl ester was measured in the same manner as DCPLA-ethyl ester (FIG. 3).

Example 4

Figure 4:
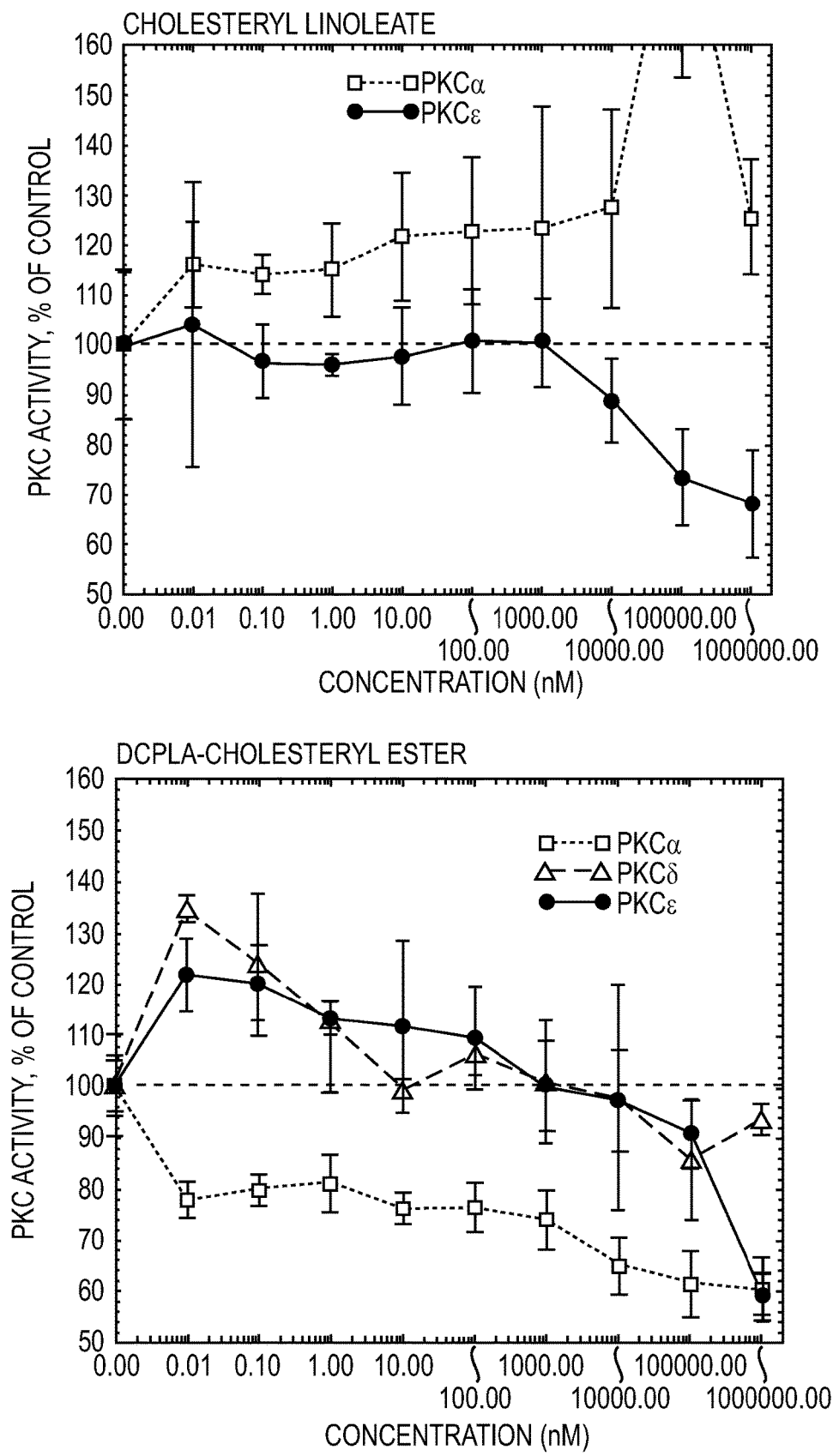
FIG. 4: PKC activation and selectivity of DCPLA-cholesteryl ester compared to cholesteryl linoleate.

DCPLA-Cholesteryl Ester Activated PKC-ε to a Greater Extent than Cholesteryl Linoleate Following the procedure in Example 1, the activation and PKC isoform specificity of DCPLA-cholesteryl ester and cholesteryl linoleate were measured (FIG. 4). DCPLA-cholesteryl ester activated both PKC-ε and PKC-δ in a biphasic manner by up to 130% of control. PKC-α was inhibited at all concentrations. This ester showed extremely high affinity for PKCPKC-ε and PKC-δ. Maximal activity was seen at 0.01 nM, which is 18× more potent than know PKC activator Bryostatin-1. Cholesteryl linoleate, by contrast, produced little or no activation of PKC-ε and only 20% activation of PKC-α.

Example 5

$EC_{50}$ Values, Specificity and Activation of Select DCPLA Esters

The $EC_{50}$ values, PKC specificity, and activation for a select number of DCPLA esters was determined (see Table 1). $EC_{50}$ values were determined by measuring the lowest concentration that activates by 50% of maximum activation. Generally, drugs with lower $EC_{50}$ values are considered more potent. As can be seen in Table 1, the esters of DCPLA show much lower $EC_{50}$ values that the corresponding acid, DCPLA. The specificity and activation of PKC by the various esters of DCPLA were calculated from the measurements of activation of PKC isozymes.

| Activator | EC50, nM | Specificity[1] ε/α | Activation[2] |
|---|---|---|---|
| DCP-LA | 1000 | 7.4 | 300 |
| DCPLA-methyl ester | 3 | 12.1 | 195 |

-continued

| Activator | EC50, nM | Specificity[1] ε/α | Activation[2] |
|---|---|---|---|
| DCPLA-ethyl ester | 3 | 4.2 | 126 |
| DCPLA-isopropyl ester | 0.1 | 1.4 | 140 |
| DCPLA-t-butyl ester | 1 | ND | 130 |
| DCPLA-cyclopropanated oleyl ester | 3 | 8.1 | 140 |
| DCPLA-retinyl ester | 10 | ND | 129 |
| DCPLA-cholesteryl ester | 0.005 | 0.94 | 122 |

[1]Activation of PKC-ε ÷ activation or inhibition of PKCα at 3 × EC$_{50}$.
[2]% of control of PKCε at maximum.
ND = not determined.

Considering the activation data of the various DCPLA esters as a whole, it appears that the DCPLA esters fall into two groups: low-affinity activators (e.g., DCPLA-ME, tert-butyl ester, retinyl ester, and cyclopropanated oleyl ester), which generally activate PKC-ε at 100-1000 nM, and high-affinity activators (e.g., DCPLA-isopropyl ester and cholesteryl ester), which generally activate PKC-ε at 0.1-1 nM. The compounds generally showed a biphasic response, activating PKC-ε at lower concentrations and inhibiting PKC-ε and other isoforms at higher concentrations.

Some DCPLA esters (e.g., DCPLA-tert-butyl ester and cholesteryl ester) also exhibited a bimodal activation, displaying two distinct levels of PKC activation in the activity vs. concentration plot, suggesting that PKC-ε may possess two phosphatidylserine binding sites of differing affinity.

Example 6

DCPLA-ME Binds to the Phosphatidylserine (C2) Binding Site

To determine the binding site of DCPLA-ME, $^3$H-DCPLA-ME was incubated with rat brain slices in the absence and presence of known C1 and C2 competitors. More specifically, rat brain sections were fixed with formaldehyde, sliced, and incubated with (1) $^3$H-DCPLA-ME alone; (2) $^3$H-DCPLA-ME with DCPLA; (3) $^3$H-DCPLA-ME with Phorbol ester; or (4) $^3$H-DCPLA-ME and Bryostatin 1. After incubation, the slices were washed with a buffer made of 130 mM NaCl, 5 mM MgCl, 5 mM KCl, 1 mM EGTA, and 0.1% bovine serum albumin in 10 mM HEPES-NaOH, pH 7.4, dried, and analyzed with film-autoradiography.

Table 2 shows that DCPLA-ME binds to the same site as DCP-LA, confirming the binding site identified by Kanno et al., *J. Lipid Res.*, 2006, 47: 1146-1156 as the phosphatidylserine (C2) site, and not C1A or C1B, since binding is only slightly inhibited by high concentrations of diacylglycerol (C1-binding-site) agonists.

TABLE 2

| Competitor | Competitor binding site | 30 nM competitor | 1 μM competitor |
|---|---|---|---|
| DCPLA | C2 | 86% | 35% |
| DCPLA methyl ester | C2 | 64% | 37% |
| Phorbol ester (PdBu) | C1 | 100% | 81% |
| Bryostatin 1 | C1 | 100% | 77% |

Example 7

Production and Size Determination of ASPDs and ADDLs

Synthetic ASPDs and ADDLs were prepared as described above. The size of the 100 kDa retentates (i.e., the ASPDs) and ADDLs were verified by SEC. The size of these ASPDs were found to be approximately 175 kDa when compared to the size standards subjected to SEC, while ADDLs showed peaks at 18, 16, and 8 kDa.

Example 8

Neurotoxic Effect of Different Aβ$_{1-42}$ Oligomers (ASPDs, <100 kDa Filtrate of ASPD, and ADDLs)

To assess the neurotoxic effect of different sized oligomers, rat primary hippocampal neurons were treated with variable concentrations of these Aβ$_{1-42}$ species for 20 hr. Viability of the treated cells was compared to untreated cells using the MTT assay.

Figure 5:
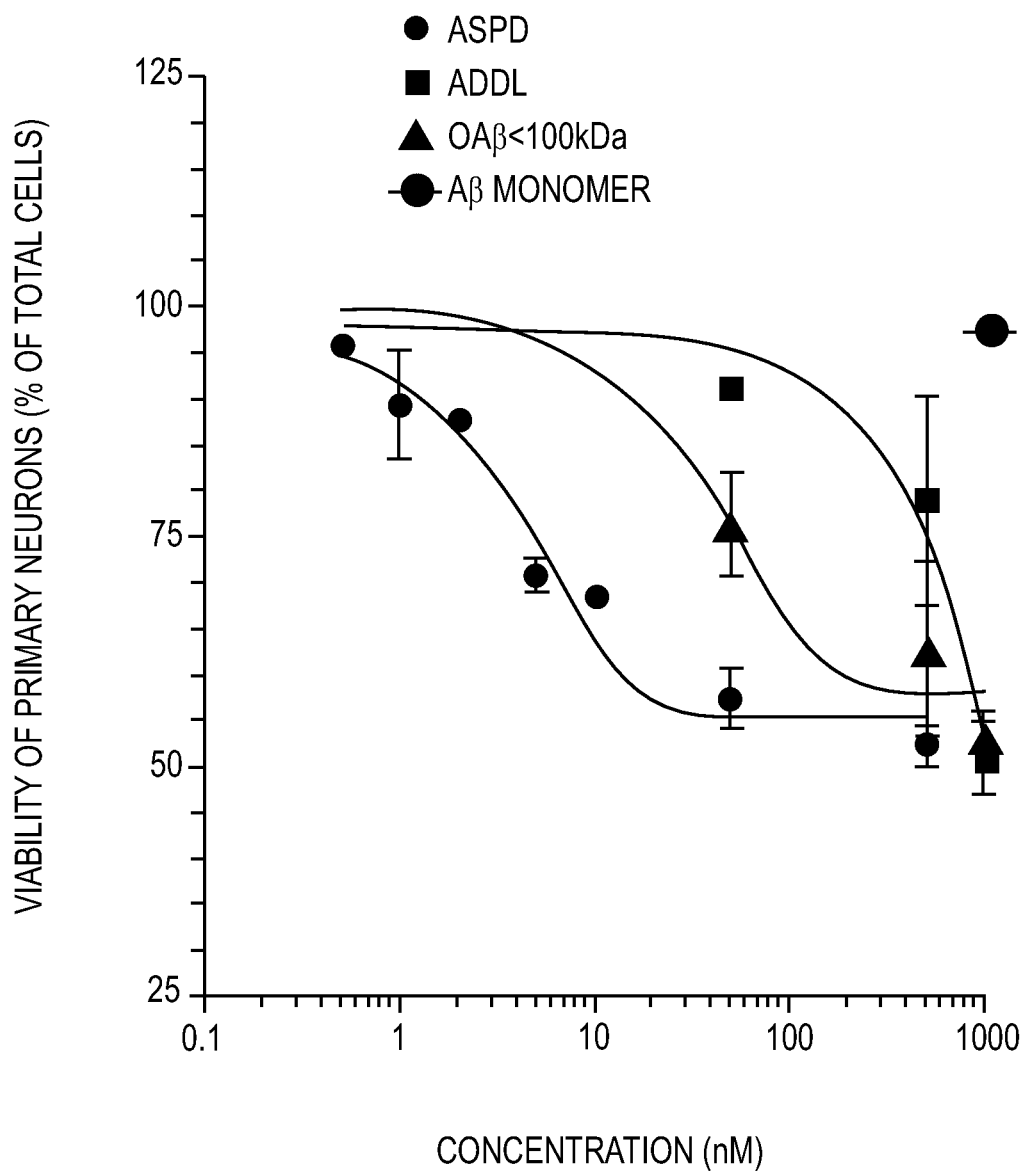
FIG. 5: Neurotoxic effect of different Aβ assemblies. ASPDs, ADDLs, OAβ<100 kDa filtrate, and monomeric Aβ were prepared as described in the Examples section herein and their toxicity on cultured primary rat hippocampal neurons after 20 hr was estimated using the MTT assay. ASPDs represent the retentate from the 100 kDa filtration and OAβ represents the filtrate.

As shown in FIG. 5, Aβ monomer at 1 μM concentration did not affect the viability of neurons (97.6%±1.3), while 1 μM ADDL (containing 6.5 monomers on average) significantly killed the neurons (50.98±3.8%, p=0.0013). ASPDs (containing 39 monomers on average) caused a significant decrease in viability at 50 nM (57.1±4.9%, p=0.0028). The OAβ<100 kDa filtrate (containing 12 monomers on average) was significantly cytotoxic at 50 nM, but less toxic than intact ASPDs. Further, it was found that ASPD can cause significant loss of viability at the very low concentrations of 2 nM, 5 nM, and 10 nM (Table 3).

TABLE 3

| | Viability of primary neuron (% of control) | | | | |
|---|---|---|---|---|---|
| Concentration | Untreated (Mean ± SEM) | Aβ Monomer (Mean ± SEM) | ASPO (Mean ± SEM) | ADDL (Mean ± SEM) | oAβ <100 kDa (Mean ± SEM) |
| 0 nM | 100 ± 4.396 | | | | |
| 0.5 nM | | | 95.12 ± 0.733 (p = 0.2166) | | |
| 1 nM | | | 89.64 ± 5.99 (p = 0.1178) | | |
| 2 nM | | | 87.75 ± 0.94 (p = 0.026) | | |
| 5 nM | | | 70.95 ± 1.89 (p = 0.0019) | | |
| 10 nM | | | 68.68 ± 0.84 (p = 0.0011) | | |
| 50 nM | | | 57.55 ± 3.35 (p = 0.0028) | 91.35 ± 1.44 (p = 0.117) | 76.01 ± 5.54 (p = 0.023) |
| 500 nM | | | 52.94 ± 3.75 (p = 0.0014) | 79.01 ± 11.32 (p = 0.089) | 62.94 ± 9.53 (p = 0.0155) |

TABLE 3-continued

| | Viability of primary neuron (% of control) | | | | |
|---|---|---|---|---|---|
| Concentration | Untreated (Mean ± SEM) | Aβ Monomer (Mean ± SEM) | ASPO (Mean ± SEM) | ADDL (Mean ± SEM) | oAβ <100 kDa (Mean ± SEM) |
| 1000 nM | | 97.60 ± 1.3 (p = 0.3614) | | 49.02 ± 7.26 (p = 0.0013) | 53.52 ± 2.43 (p = 0.0011) |

The data suggests that ASPDs are the most toxic oligomeric species and 50 nM of ASPDs causes damage equivalent to that caused by 1 μM ADDLs or 1 μM of <100 kDa filtrate (OAβ) of ASPDs. In terms of monomers, ASPDs were shown to be 6 times more toxic than ADDLs and 10 times more toxic than Aβ monomer.

All further experiments used 50 nM concentration of ASPDs unless otherwise indicated.

Example 9

Bryostatin-1, DCPLA, and DCPLA-ME Protected Against ASPD Induced Neurotoxicity

PKC activators are reported to provide neuroprotection against Aβ, possibly by activating TACE (tumor necrosis factor-α converting enzyme) and Aβ-degrading enzymes such as endothelin-converting enzyme, insulin degrading enzyme or neprilysin, or by stimulating synaptogenesis.

Figure 6A:
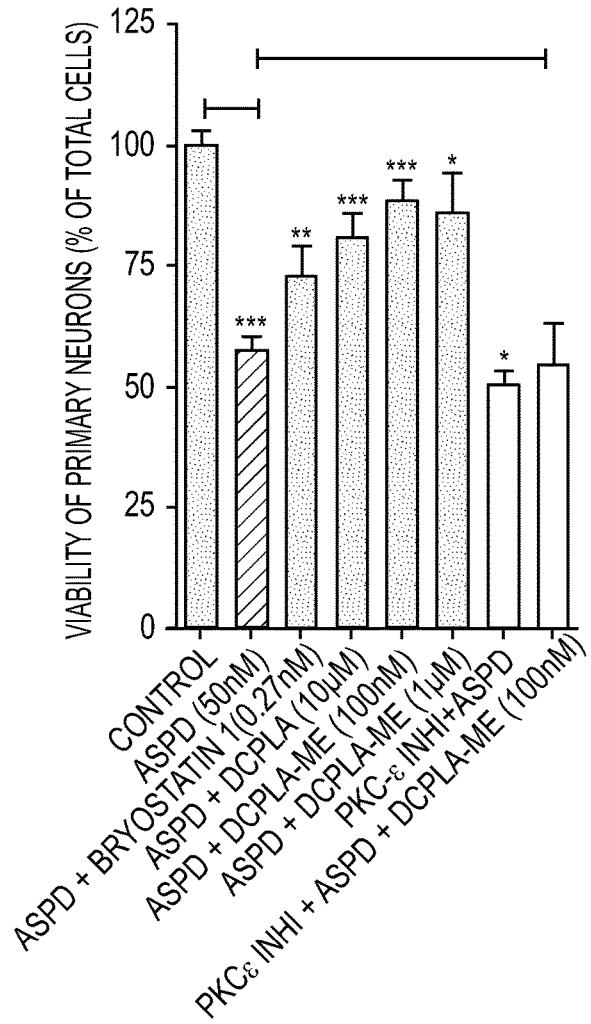
FIGS. 6A and 6B: Neuroprotection by PKC activators (Bryostatin-1, DCPLA, and DCPLA-ME) against ASPD induced toxicity. Cell viability after PKC activator (bryostatin, DCPLA, and DCPLA-ME) treatments in 50 nM ASPD-treated cultured primary rat hippocampal neurons (FIG. 6A) and SH-SY5Y cells (FIG. 6B) was measured by MTT assay as described herein. Viability of neurons and cells treated with DCPLA-ME after treatment with PKC-ε translocation inhibitor peptide [EAVSLKPT] was also measured. Among the PKC activators, DCPLA-ME (100 nM) was found most protective against ASPDs. Data represent mean±SEM. (Student's t test *. p<0.05; , p<0.005 and *, p<0.0005, n=6).

Bryostatin-1, DCPLA, and DCPLA-ME were tested against ASPD-induced cytotoxicity to determine their neuroprotective efficacy. The tested PKC-ε activators were neuroprotective against 20 hr treatment with ASPD in primary neurons (FIG. 6A). Primary neurons treated with 50 nM ASPD showed 57.6±1.6% viability. Bryostatin-1 (0.27 nM), DCPLA (10 μM), and DCPLA-ME (100 nM) treatment restored the viability to 73.23±3.6% (p=0.0083, n=6), 81.43±2.76% (p=0.0009, n=6), and 89.16±2.27% (p=0.0002, n=6), respectively. When added to the cells with DCPLA-ME, the PKC-ε translocation inhibitor peptide [EAVSLKPT] blocked DCPLA-ME's protective effect, suggesting that the neuroprotection against Aβ is mediated by PKC-ε activation.

DCPLA-ME-treated cells were 8% and 16% more viable than DCPLA-treated and Bryostatin-1-treated cells. The data show that DCPLA-ME provided better neuroprotection compared to DCPLA and Bryostatin-1.

Figure 6B:
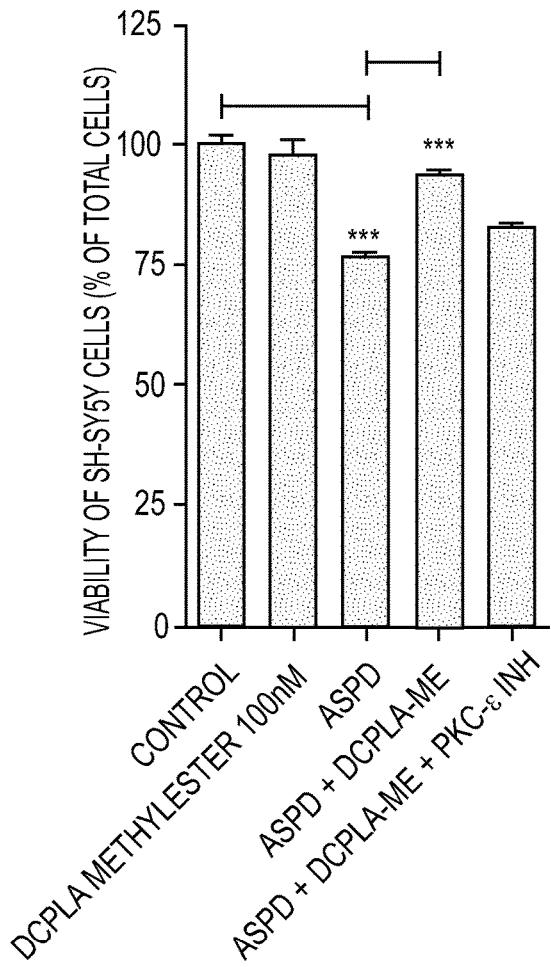

The effect of ASPD and DCPLA-ME on differentiated human SH-SY5Y cells was also studied (FIG. 6B). In ASPD-treated cells, the viability was 77.15±0.49% (p<0.0001, n=6) compared to the untreated cells. DCPLA-ME protected the SH-SY5Y cells against ASPD and restored the viability to 93.8±0.57% (p<0.0001, n=6).

Example 10

ASPD Treatment Decreased PKC-ε

PKC-ε is reported to have neuroprotective effects and is known to maintain/repair synaptic structure. See e.g., Nelson, T. J. et al., *Trends Biochem. Sci.*, 2009, 34: 136-145; Hongpaisan, J. et al., *J. Neurosci.*, 2011, 31: 630-643; Hongpaisan, J. et al., *Proc. Natl. Acad. Sci. USA*, 2007, 104: 19571-19576; and Sun, M. K. et al., *Pharmacol. Ther.*, 2010, 127: 66-77. Therefore, to assess if ASPD has an inhibitory action on PKC-ε, the PKC-ε level after ASPD treatment was measured.

Figure 7A:
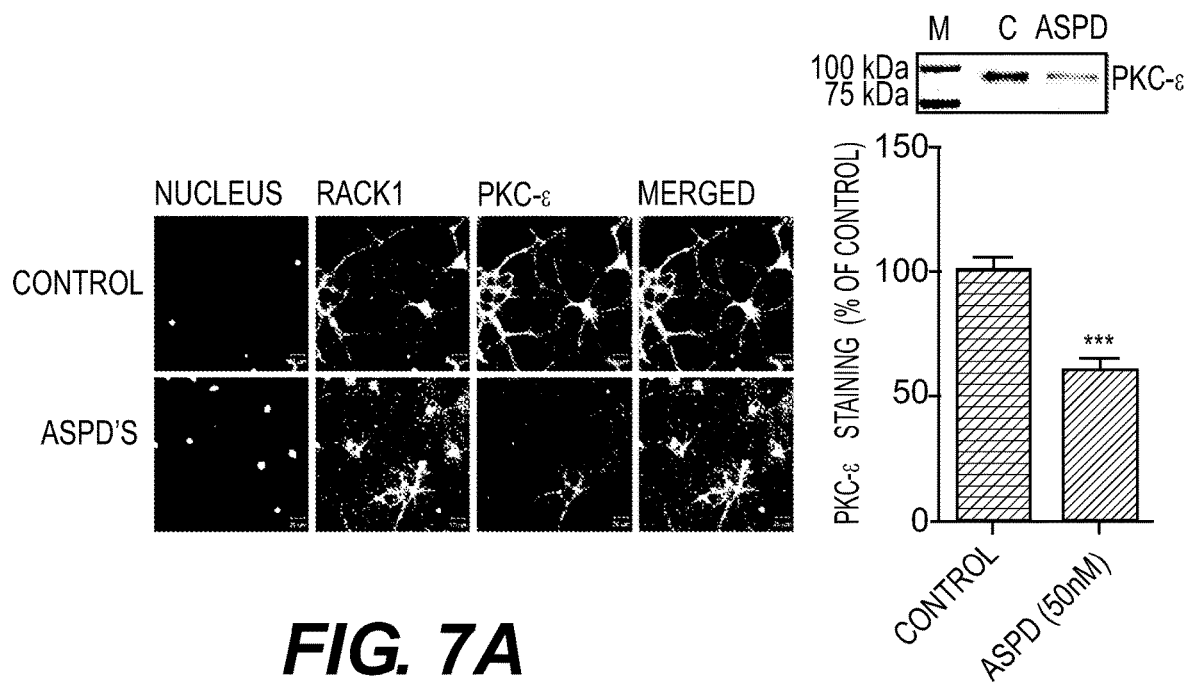
FIG. 7A: ASPD treatment reduces PKC-ε expression. PKC-ε level in cultured primary rat hippocampal neurons was measured by immunofluorescence (n=6) and Western Blot (n=3) as described in the Examples section. For cell staining, 20 hr ASPD-treated cells were washed, fixed, and permeabilized. Cells were then immunostained and imaged in a confocal microscope. Both confocal image analysis and Western Blot showed a significant decrease in PKC-ε level after ASPD treatment. "M" is the molecular weight marker; "C" is the control.

ASPD treatment reduced the PKC-ε immunofluorescence level to 60.81±5.85% compared to control (p=0.0008, n=6) in primary neurons (FIG. 7A), which was further confirmed by Western Blot. Other control proteins, including β-actin, were not affected by ASPD. This suggests that the toxic effects of Aβ multimers may be mediated in part by reduction of PKC.

Figure 7B:
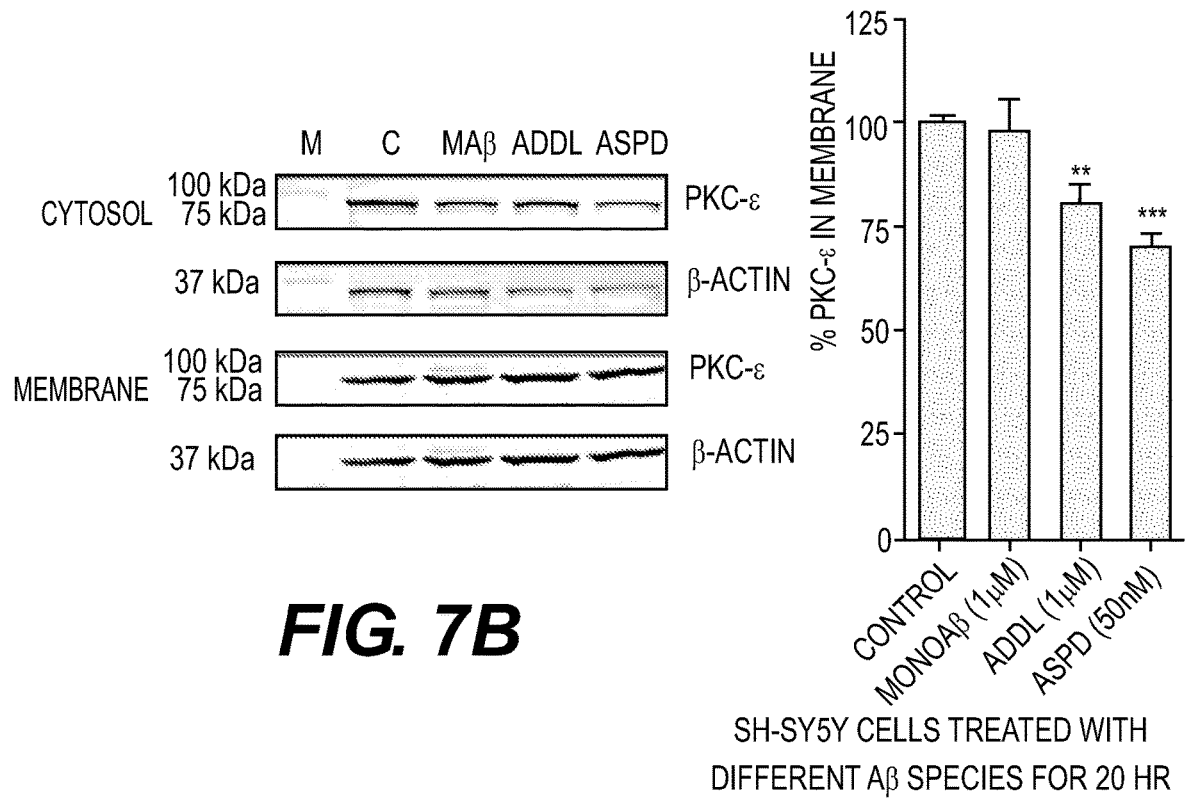
FIG. 7B: PKC-ε translocation to membrane after ASPD and ADDL treatment. Control ("C") and SH-SY5Y neuroblastoma cells treated with monomer Aβ, ADDL, or ASPD were separated into membrane and cytosol fractions and a Western Blot was performed. PKC-ε activation was measured as the percentage of total PKC-ε present in the membrane. Data are represented as mean±SEM. (Student's t test , p<0.005 and *, p<0.0005). "M" is the molecular weight marker; "C" is the control.
Figure 8B:
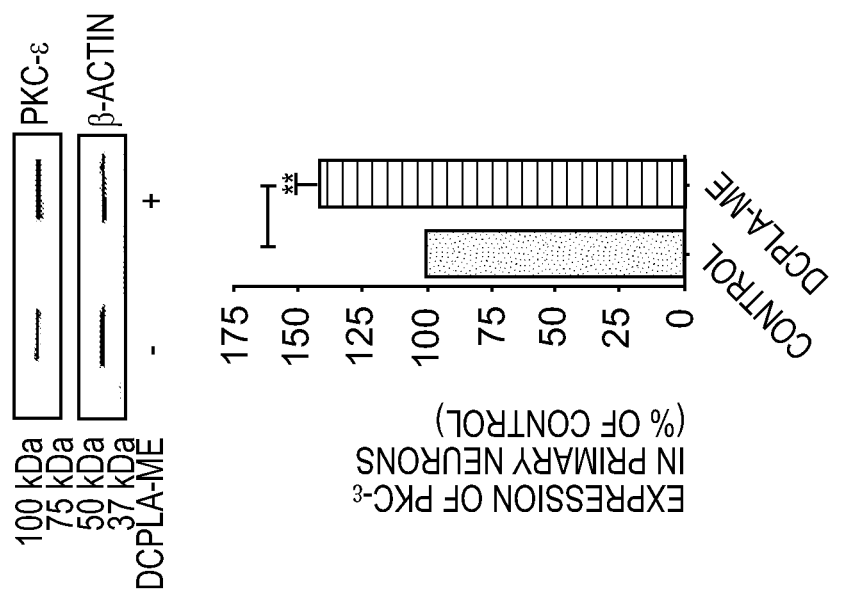
FIG. 8: DCPLA-ME prevents ASPD induced PKC-ε loss. Primary neurons were treated with ASPD and/or DCPLA-ME (FIG. 8A). Data are represented as mean±SEM of normalized PKC-ε value. Western Blot analysis was conducted on: primary neurons treated with 100 nM DCPLA-ME (FIG. 8B); 50 nM ASPD-treated primary neurons treated with DCPLA-ME in the presence and absence of 5 μM PKC-ε inhibitor [EAVSLKPT] (FIG. 8C); and PKC-ε activation in control and treated SH-SY5Y cells (FIG. 8D). PKC-ε expression was normalized to β-actin. Data are represented as mean±SEM of three independent experiments. (Student's t test *. p<0.05;, p<0.005 and *, p<0.0005).
In FIG. 8D, "soluble" represents the PKC-ε remaining in the cytosol while "particulate" represents the PKC-ε present in the membrane. PKC activation was measured as the percentage of total PKC-ε present in the membrane.
Figure 8A:
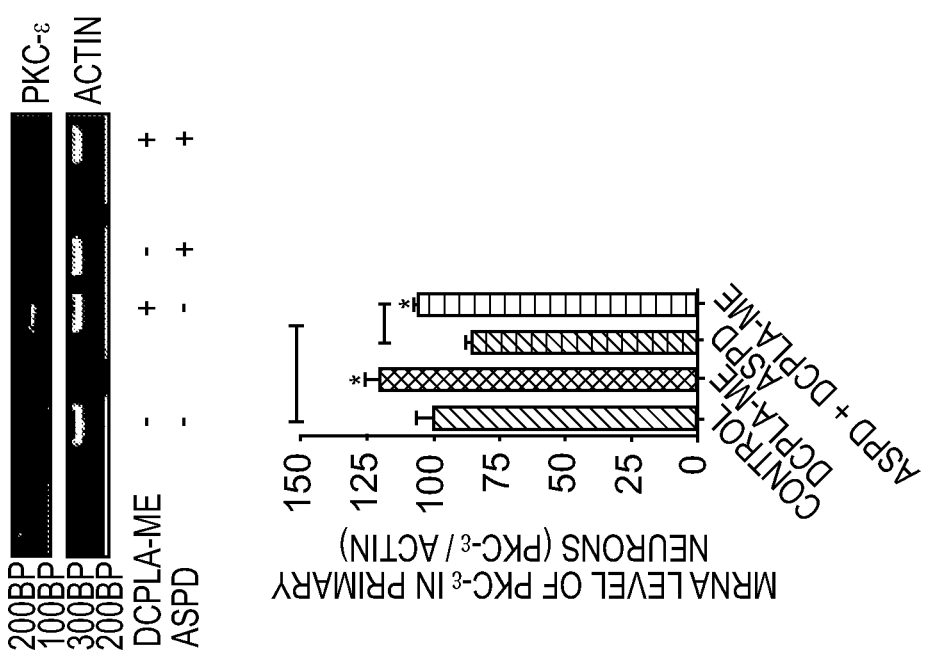
Figures 8C, 8D:
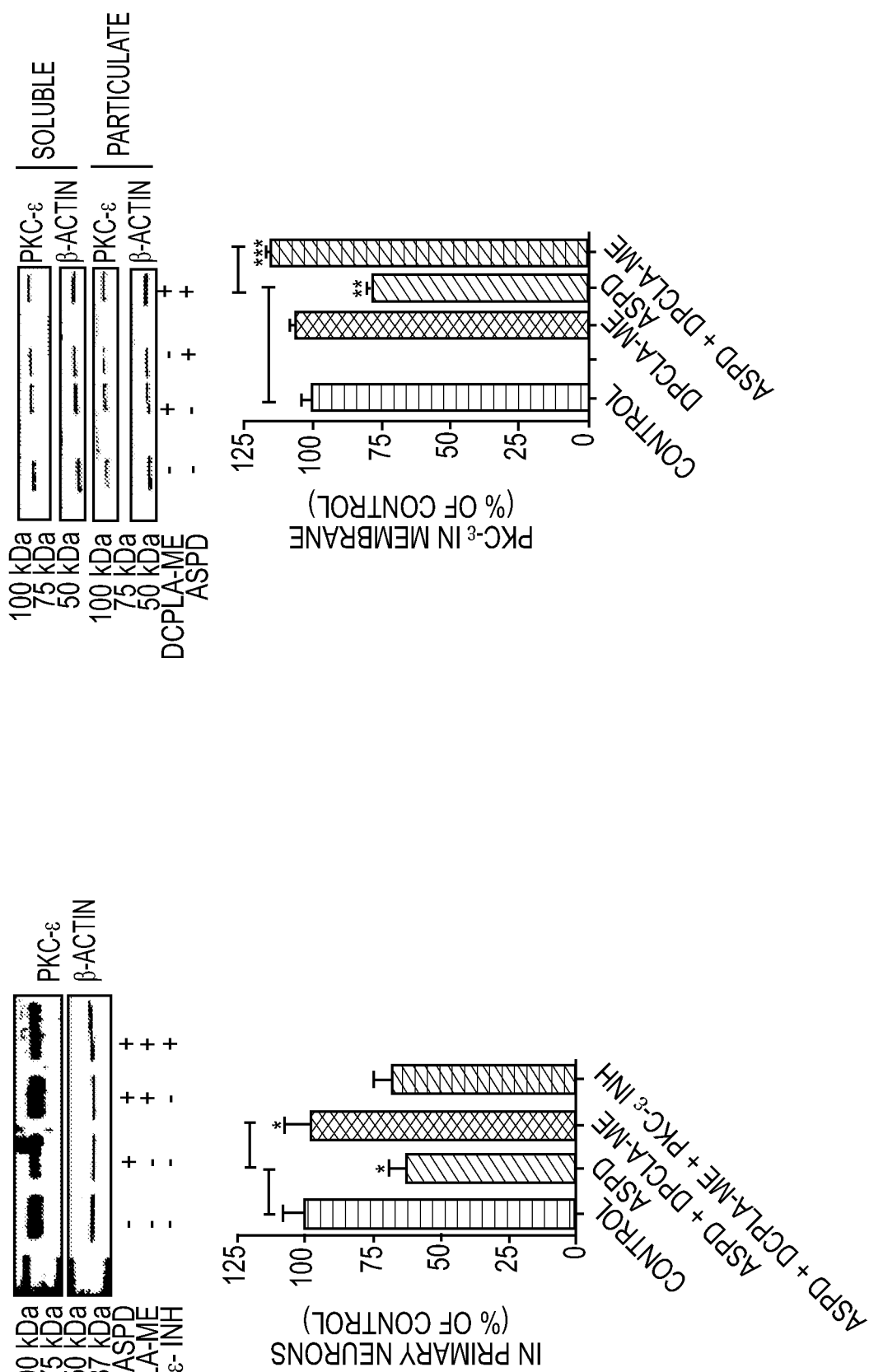

The effect of ASPDs on PKC-ε activation was analyzed by measuring the translocation of the enzyme to the membrane in SH-SY5Y neuroblastoma cells (FIG. 7B). ASPD reduced PKC-ε membrane translocation by 30% (69.98±3.27%, p=0.0006, n=3), while ADDL at 20-fold higher concentrations decreased PKC-ε by only 20% (80.82±4.025%, p=0.0058, n=3). $A\beta_{1-42}$ monomers at 1 μM did not affect translocation. This indicates that low concentrations of ASPDs target PKC-ε by interfering with an upstream signaling pathway leading to its degradation and reduced activation. Addition of DCPLA-ME restored PKC-ε translocation to normal (FIG. 8D).

Example 11

DCPLA-ME Induced Activation of PKC-ε Leading to Neuroprotection

Basal PKC-ε level and activation of the enzyme are affected by Aβ oligomers that induced neurotoxicity and that DCPLA-ME treatment helped the cells to survive. The effect of DCPLA-ME on PKC-ε protein levels and activation was next evaluated.

Primary neurons were treated with ASPD and/or DCPLA-ME. PKC-ε mRNA was quantified by RT-PCR as described above. RNA prepared from control and treated cultured primary rat hippocampal neurons were isolated and reverse transcribed. Individual cDNA was amplified for PKC-ε and β-actin. PKC-ε expression was normalized to β-actin.

In primary neurons, DCPLA-ME increased PKC-ε transcript levels both in controls and ASPD-treated cells (FIG. 8A), while ASPD alone did not change PKC-ε mRNA significantly. DCPLA-ME also restored the PKC-ε protein level to normal (FIG. 8B). This protection was completely blocked by 5 μM PKC-ε translocation inhibitor [EAVSLKPT] (FIG. 8C). In SH-SY5Y neuroblastoma cells, ASPD reduced PKC-ε translocation by 46%. DCPLA-ME restored PKC-ε translocation to normal (FIG. 8D).

Example 12

ASPD Caused Synaptic Damage

To estimate the synaptic damage caused by the ASPDs on primary hippocampal neurons, the expression of synaptophysin (a presynaptic marker) and PSD-95 (a postsynaptic marker) was measured by immunofluorescence staining. Cells grown on chambered slides were treated with vehicle (control), Aβ monomer (1 μM), ADDLs (1 μM), and ASPD (50 nM). Following a 20 hr incubation period, the cells were stained for nucleus, PSD-95, and synaptophysin. Expression levels were calculated as the change of percentage in mean fluorescence intensity compared to untreated cells.

Compared to the control, 50 nM ASPDs caused a 40% decrease in synaptophysin intensity (62.45±6.74%, p=0.0071) and 1 µM ADDLs caused a 25% decrease (75.64±4.84%, p=0.033) (FIGS. 9A and 9C). PSD-95 expression also decreased 42% (±10%) in the ASPD treated cells (FIGS. 9A and 9B). $A\beta_{1-42}$ monomer at 1 µM concentration did not change the expression of synaptophysin or PSD-95. This indicates that ASPDs disrupt synaptic integrity even at nanomolar concentrations.

Example 13

DCPLA-ME Protected Neurons Against ASPD Induced Synaptic Loss

Primary neurons, treated and untreated, were immunostained for MAP-2, synaptophysin, and PSD-95 to determine the synaptic integrity. Cells grown on chambered slides were treated with vehicle (control), 50 nM ASPD, 50 nM ASPD and 100 nM DCPLA-ME, and 50 nM ASPD and 100 nM DCPLA-ME and 5 µM PKC-ε translocation inhibitor [EAVSLKPT]. The PKC-ε inhibitor was added 30 min before adding ASPD and DCPLA-ME. Following a 20 hr incubation period, the cells were stained for MAP-2, PSD-95, and synaptophysin as described above.

Figure 10A:
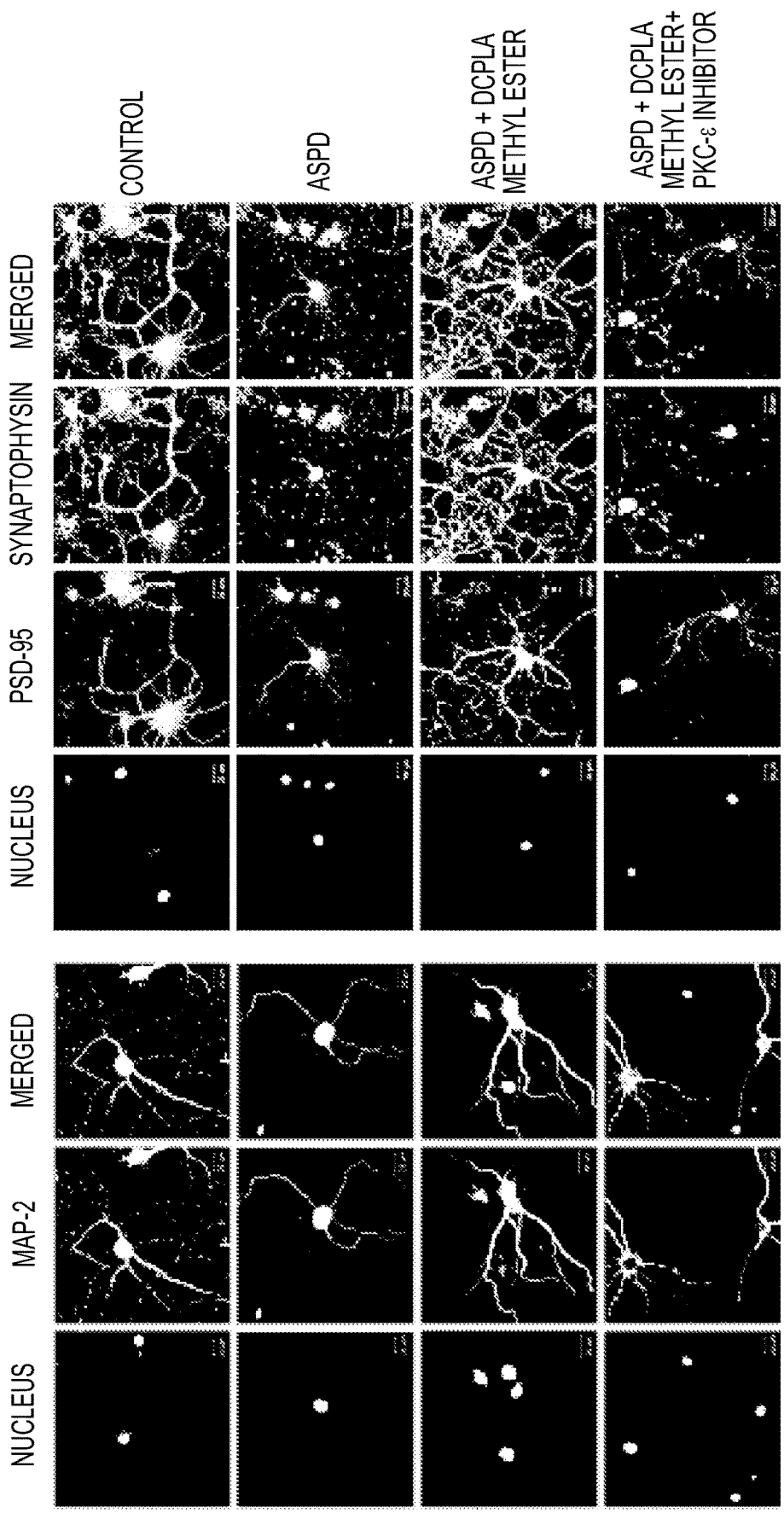
FIG. 10: DCPLA-ME protects from ASPD induced synaptic loss. Confocal images of rat hippocampal primary neurons are shown in FIG. 10A. The first "merged" column is the merge of the prior two columns—i.e., cells stained for nucleus and MAP-2. The second "merged" column is the merge of the three prior columns—i.e., cells stained for nucleus, PSD-95, and synaptophysin. Mean fluorescence intensity was calculated and was expressed as percentage of control (n=6). ASPD treatment showed marked decrease in stained neurite processes, while DCPLA-ME protected against synaptic loss.
FIG. 10C is a Western Blot analysis of synaptophysin expression in control, ASPD-treated cells, cells treated with ASPD and DCPLA-ME, and cells treated with PKC-ε inhibitor [EAVSLKPT], ASPD, and DCPLA-ME treated primary rat hippocampal neurons. Values are represented as mean±SEM. (Student's t test *. p<0.05;, p<0.005 and *, p<0.0005).

It was found that the PSD-95 and synaptophysin staining of the neurites decreased after ASPD treatment, while DCPLA-ME treatment increased their staining in neurite branches (FIG. 10A).

Figure 10C:
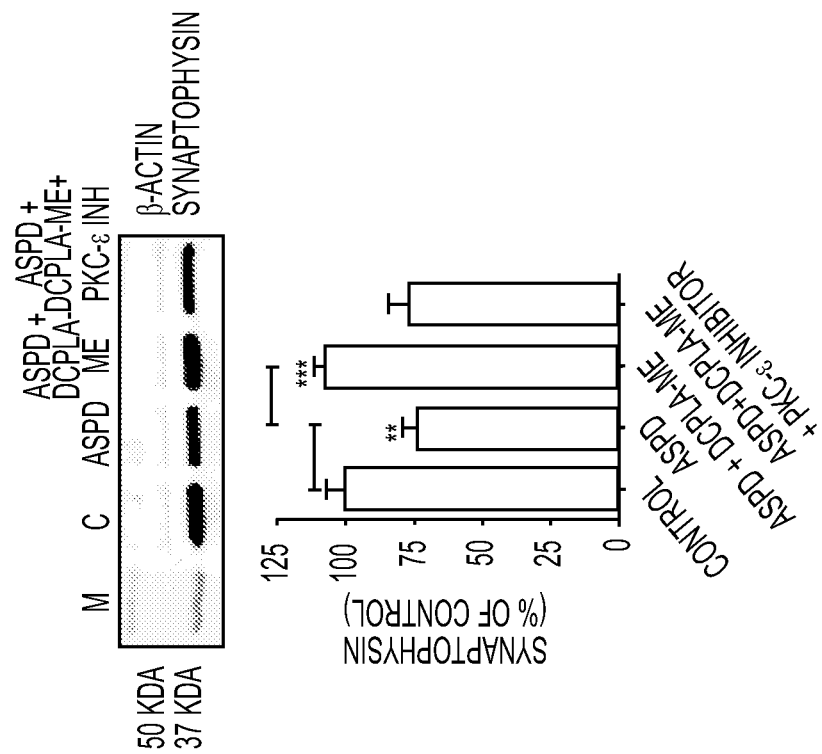
Figure 10B:
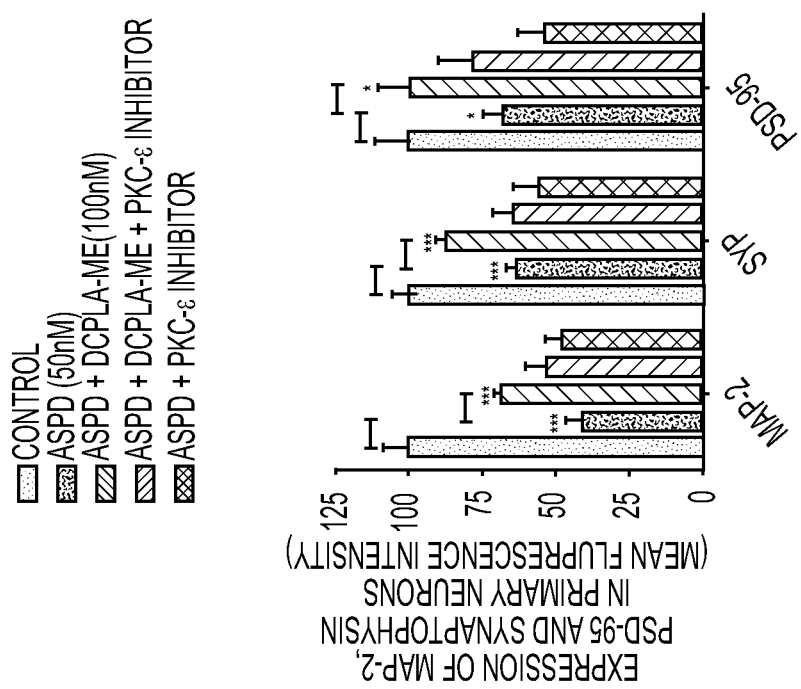

DCPLA-ME treatment increased the expression (mean fluorescence intensity) of MAP-2 in ASPD-treated cells from 40.7±6.2% to 68.87±2.0% (p=0.0007, n=5), synaptophysin from 63.3±3.8% to 87.48±3.75% (p=0.0005, n=5), and PSD-95 from 67.63±7.24% to 99.2±11.3% (p=0.02, n=5) (FIG. 10B). These results suggest that DCPLA-ME not only protected the ASPD cells from cell death but also prevented the synaptic damage by increasing expression of synaptophysin, PSD-95, and MAP-2 in synaptic networks. The expression of synaptophysin was confirmed by Western Blot, and showed that ASPD decreased the expression by 26% (73.30%±3.319, p=0.0035, n=3) and DCPLA-ME treatment maintained the expression similar to control (FIG. 10C).

Example 14

DCPLA-ME Inactivated GSK-3β in ASPD Treated Primary Neurons

Figure 11:
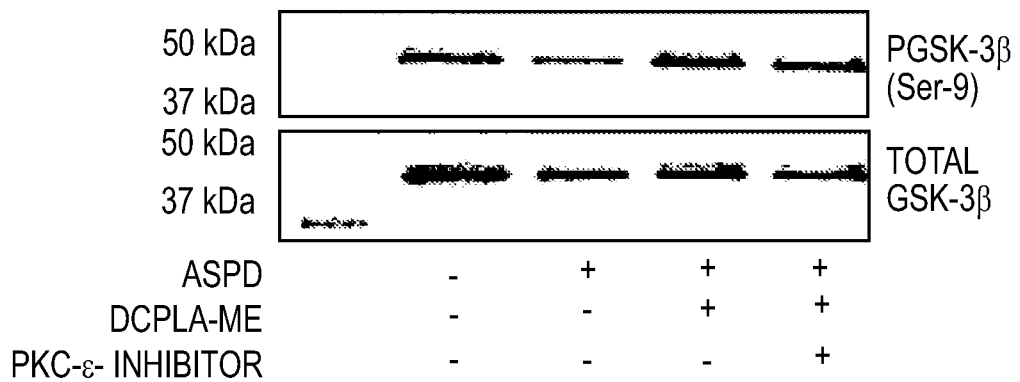
FIG. 11: DCPLA-ME inactivates GSK-3β in ASPD treated primary neurons. Western Blot analysis of phospho GSK-3β (Ser-9) and total GSK-3β protein from rat hippocampal neurons treated with vehicle (control), ASPD (50 nM), ASPD (50 nm) and DCPLA-ME (100 nM), and ASPD (50 nm), DCPLA-ME (100 nM), and PKC-ε inhibitor (5 μM) [EAVSLKPT]. Phospho GSK-3β expression was normalized against total GSK-3β expression. ASPD treatment activated GSK-3β while DCPLA-ME treatment inactivated GSK-3β. Data are represented as mean±SEM. (Student's t test *. p<0.05; and **, p<0.005 n=3).
Figure 11:
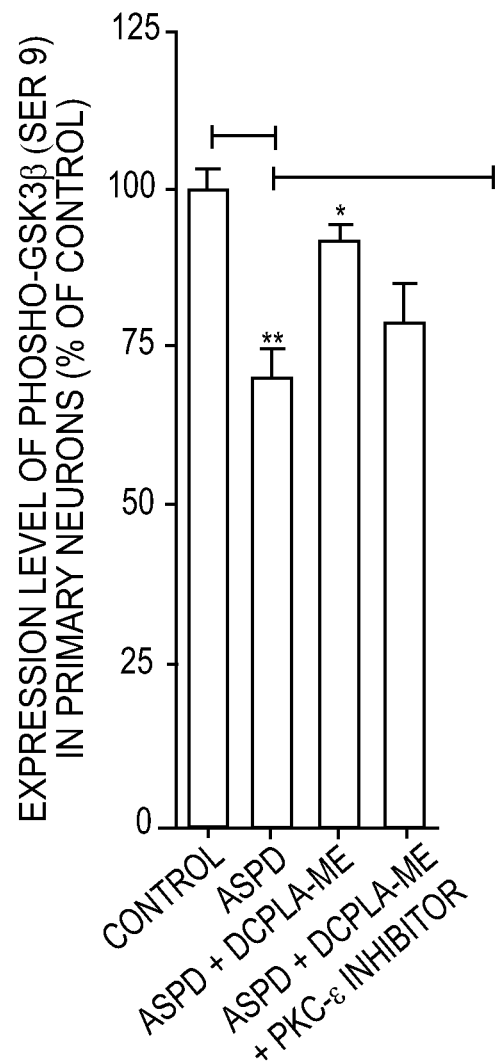

DCPLA-ME treatment of ASPD-treated cells restored phosphorylation of the Ser-9 residue of GSK-3β to normal levels, as evidenced by an increased signal in anti-phospho-Ser-9 Western Blots (FIG. 11). Since GSK-3β is a key enzyme in the production of hyperphosphorylated tau protein, and phosphorylation of the Ser-9 residue causes GSK-3β inhibition, increasing phosphorylation of GSK-3β at Ser-9 by PKC could also enhance the protective effect of DCPLA-ME.

Example 15

DCPLA-ME Leads to Synaptogenesis in Human Cortical Neurons

To examine the effects of PKC-c activation, cultured human cortical neurons in serum-free artificial medium were exposed to 100 nM DCPLA-ME or 0.27 nM Bryostatin-1 added every three days, along with 50% medium replacement, for 40 days. More specifically, human primary cortical neurons were grown in Neuronal Medium (ScienCell Cat No #1521) containing neuronal growth supplement (NGS) (Sciencell Cat No #1562).

Composition of NGS—

When a 500 ml bottle of NM is supplemented with NGS, the final concentrations of the supplement components per milliliter will be 100 ug BSA, 2.5 ug/mL catalase, 1 ug/mL glutathione (reduced), 4 ug/mL insulin, 0.0026 uM T3, 2 ug/mL L-Carnitine, 16 uM Ethanolamine, 15 ug/mL galactose, 16.1 ug/mL Putrescine, 0.01435 ug/mL Sodium Selenite, 0.02 ug/mL Corticosterone, 0.02 uM Progesterone, 3.5 nM Linoleic Acid, 1 ug/mL linolenic acid, 0.2 uM Lipoic Acod, 0.01 ug/mL Retinyl acetate, 0.1 ug/mL D,L-alpha-tocopherol acetate, and 0.1% ethanol.

Cells were plated on poly-l-lysine (0.001%) coated plates at a density of >10000 cells/cm2. Half of the media was replaced by new media every 3 days. DCPLA-ME or Bryostatin was dissolved in 100% ethanol and added at final concentration (100 nM for DCPLA-ME, 0.27 nM for Bryostatin). Fresh DCPLA-ME (100 nM) or Bryostatin (0.27 nM) was added every 3 days during media change. The experiments were continued for 40 days.

Figure 12:
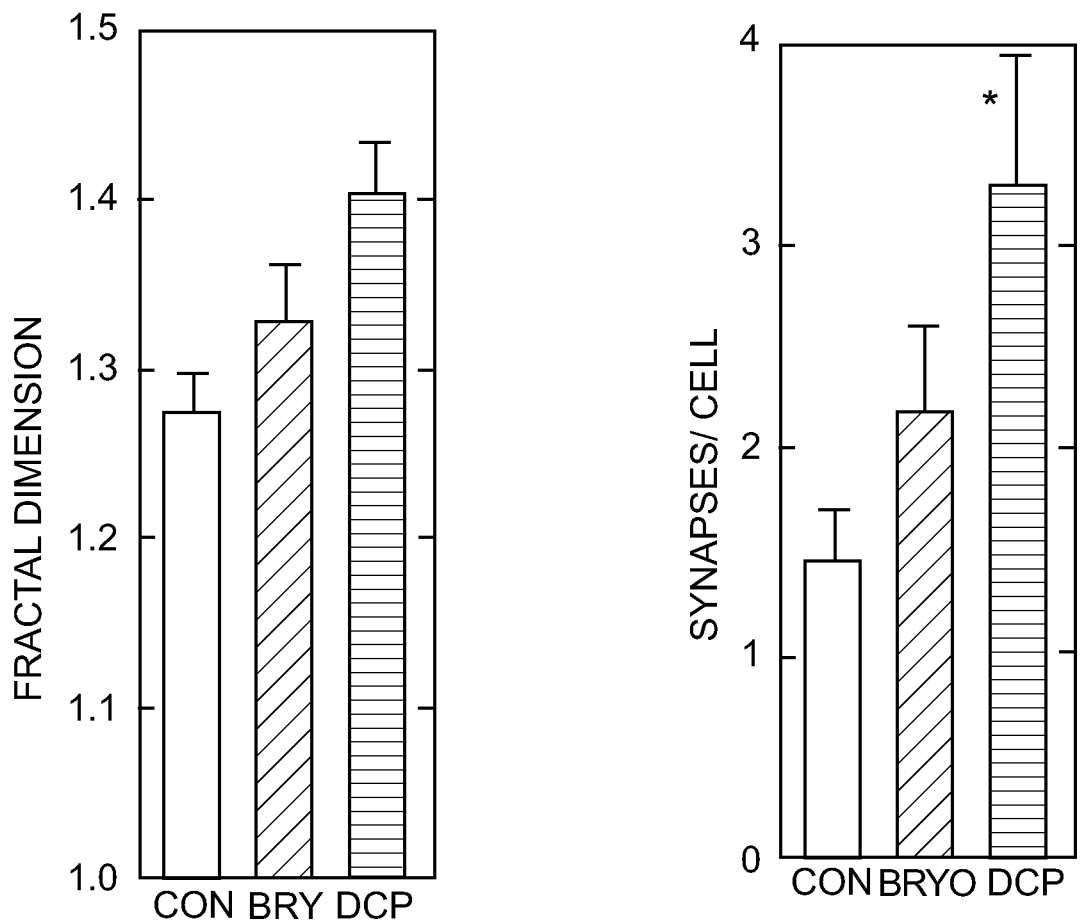
FIG. 12: Effects of DCPLA-ME and Bryostatin on cortical neurons. Left: fractal dimension in primary human cortical neurons. Right: synapses/cell in 212×212 μm field. "DCP" is DCPLA methyl ester. "Bry" is bryostatin. (*p<0.03)

DCPLA-ME increased neuronal survival from 20 to over 40 days. The DCPLA-ME-treated cells had 360±45 neurite-positive cells/field compared to 130±8 in the untreated group. DCPLA-ME increased the number of colocalized puncta of synaptophysin and PSD-95, indicative of synapses, to 230% of control (FIG. 12), indicating that PKC-ε activation can induce synaptogenesis in human neurons. Neuritic branching was also increased, as evidenced by an increase in the fractal dimension from 1.27±0.02 to 1.40±0.03 (p=0.03) (FIG. 12). The PKC-ε activation produces a marked growth in network connectivity and complexity in human neurons. Thus, DCPLA esters such as DCPLA-ME could provide a significant therapeutic benefit in a variety of neurological disorders.

Example 16

DCPLA-ME Improved Learning and Memory Retention in a Dose-Dependent Manner without Affecting Sensorimotor Ability or Motivation Water maze spatial learning and memory task (2 training trials/day for 4 days) was used to evaluate effects of oral DCPLA-ME on learning and memory in rats. A visible platform test was conducted after the end of the experiments to evaluate whether the treatment might result in an altered sensorimotor activity and escape motivation.

Male adult Wistar rats (200-250 g) were housed in a temperature-controlled (20-24° C.) room for a week, allowed free access to food and water, and kept on a 12-h light/dark cycle. Rats were anesthetized with sodium pentobarbital (60 mg/kg i.p) and placed in a stereotactic apparatus (Kopf Instruments, Tujunga, Calif.). The core temperature of rats was monitored and kept constant (38.0±0.5° C.) with warming light and pad. Two stainless steel guide cannulas were placed with the tips positioned at the coordinates (anterior-posterior, 0.5 mm; lateral, 1.5 mm; horizontal, 3.2 mm), under aseptic conditions. At the end of surgery and under appropriate anesthesia, rats received (s.c.) banamine (1 mg/kg) and ketoprofen (5 mg/kg) in lactate/Ringer's solution. A 7-day recovery period was allowed before any further experimentation.

On the first day of experiments, all rats were randomly assigned to different groups and swam for 2 min in a 1.5-(diameter)×0.6-m (depth) pool (22±1° C.). On the following day, rats were trained in a two-trial per day task for four consecutive days. Each training trial lasted for up to 2 min, during which rats learned to escape from water by finding a hidden platform that was placed at a fixed location and submerged 1 cm below the water surface. The navigation of the rats was tracked by a video camera. The escape latency and the route of rats' swimming across the pool to the platform were recorded. The quadrant test (1 min) was performed after removing the platform, 24 hr after the last training trial.

Figure 13:
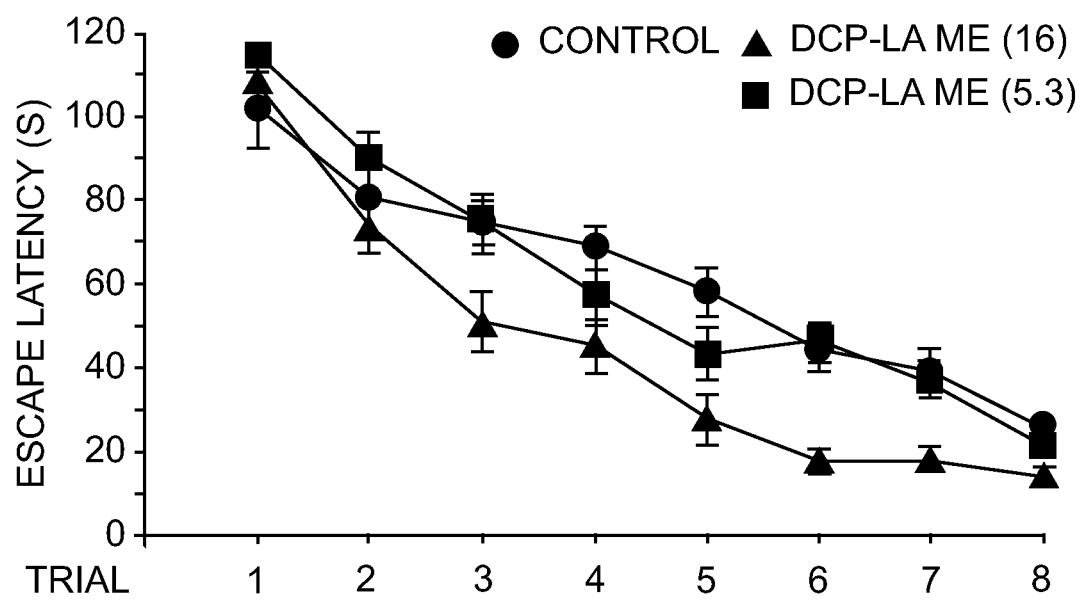
FIG. 13: DCPLA-ME exhibits dose-dependent improvements in learning. DCPLA-ME was administered at either 5.3 mg/kg or 16.0 mg/kg to rats as described in the Examples section. The effects were evaluated in a water maze spatial learning test and compared with a control group.
Figure 14A:
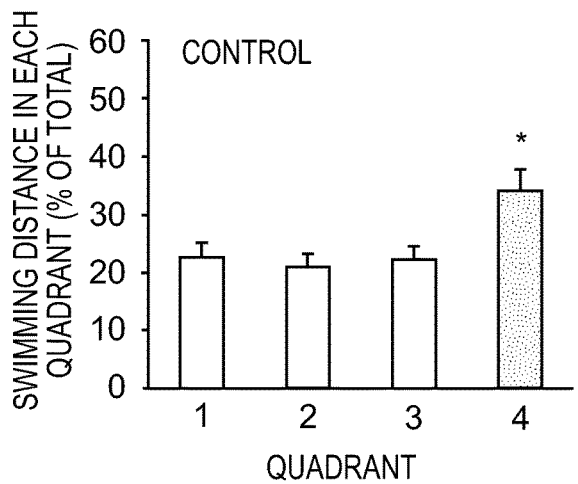
FIG. 14: DCPLA-ME exhibits dose-dependent improvements in memory. DCPLA-ME was administered at either 5.3 or 16.0 mg/kg to rats as described in the Examples section. Data were analyzed using a target quadrant ratio.
Figure 14B:
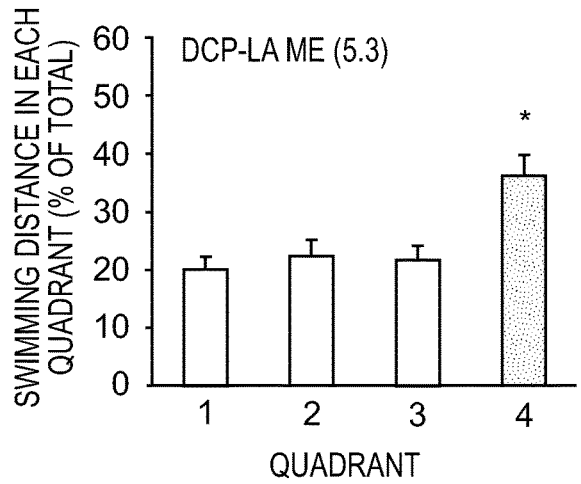
Figure 14C:
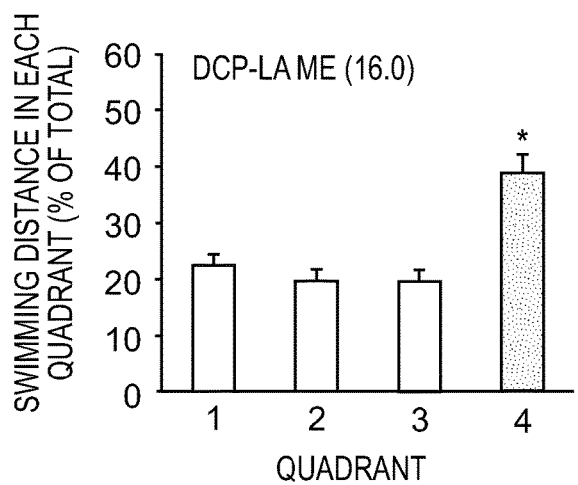
Figure 14D:
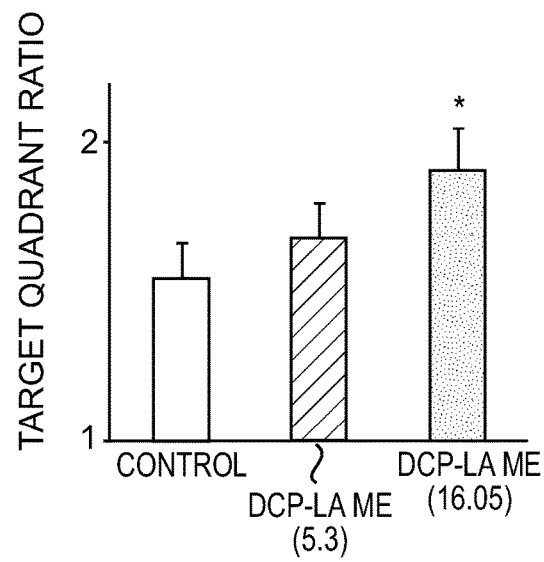

DCPLA-ME was administered at either 5.3 or 16.0 mg/kg (intragastric, 8 doses total of 2/week with the first 6 doses before the water maze task and the seventh and eighth doses 0.5 hr after the second trial of the first and third training day). As shown in FIG. 13, all the rats learned the water maze task, as evidenced by a shorter escape latency over trials ($F7,191=19.724$, $p<0.001$). There was a significant difference ($F2,191=7.717$, $p<0.001$) among the groups and a significant difference between the 16.0 mg/kg dose and control groups ($F1,127=13.389$, $p<0.001$), indicating an improved learning performance upon administration of DCPLA-ME. The learning performance improved between the 5.3 mg/kg DCPLA-ME dose and control groups, although this improvement did not reach a significant level ($F1,127=0.657$, $p>0.05$).

In the memory retention test, all the rats showed a target quadrant preference (FIG. 14). Data were analyzed using a target quadrant ratio (dividing the target quadrant distance by the average of the non-target quadrant values during the probe test; FIG. 14D). The data showed a significant difference in the target quadrant ratios between the 16.0 mg/kg DCPLA-ME dose and control groups ($F1,15=4.981$, $p<0.05$) but not between the 5.3 mg/kg dose and control groups ($F1,15=0.397$, $p>0.05$).

At the end of the experiments, the rats were also tested in a visible platform test to evaluate whether the treatment might result in an altered sensorimotor activity and escape motivation. There was no significant difference ($F_{3,31}=1.127$, $p>0.05$; not shown) among the groups in that test, indicating that the oral DCPLA-ME treatment did not affect rats' sensorimotor ability and motivation for an escape.

Example 17

PKCε Specific Activation by DCPLA-ME Protects Primary Human Neurons from Degeneration Over Time Human primary neurons (ScienCell Research Laboratories, USA) were thawed and plated on poly-L-lysine coated plates at a density of 10,000 cells per $cm^2$ and were maintained in neuronal medium (DMEM+high glucose+neuronal growth supplement, ScienCell Research Laboratories, USA) following the recommended method. Primary human neurons were then treated with either DCPLA-ME (100 nM) or bryostatin 1 (0.27 nM) for 40 days. Fresh drug was added every third day with 50% media change.

Cells treated with either DCPLA-ME or bryostatin 1 showed a better survival with neuritic branching and connections. (FIG. 15A). Untreated cells showed degeneration after 20 days, while the treated cells were healthy for at least 40 days (FIG. 15B). Expression levels of PKCε, PSD-95 and synaptophysin were significantly higher in the DCPLA-ME-treated cells compared to control or bryostatin 1-treated cells (FIGS. 15C, D, E, F & G).

Figure 15H:
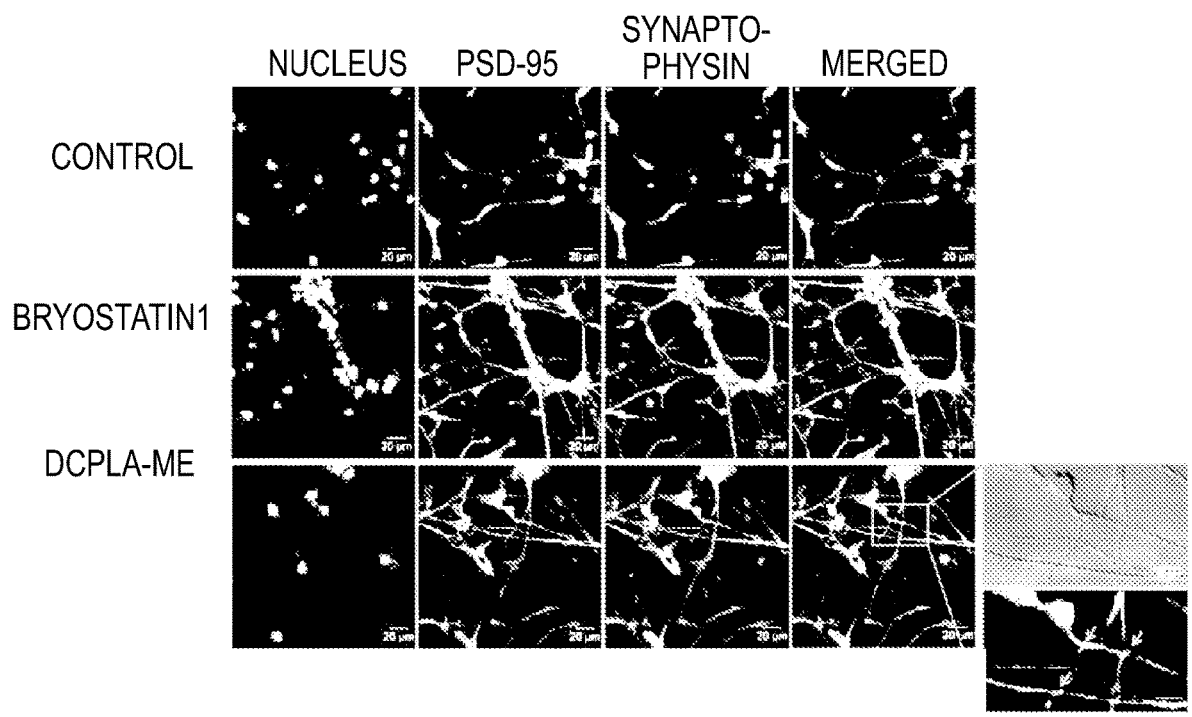
FIG. 15H—Confocal images of 30 day old neurons. DCPLA-ME and bryostatin 1 increased co-localized staining of PSD-95 and synaptophysin in puncta, indicating an increase in the number of synapses. Inset shows enlarged region illustrating a typical synapse.
Figure 15I:
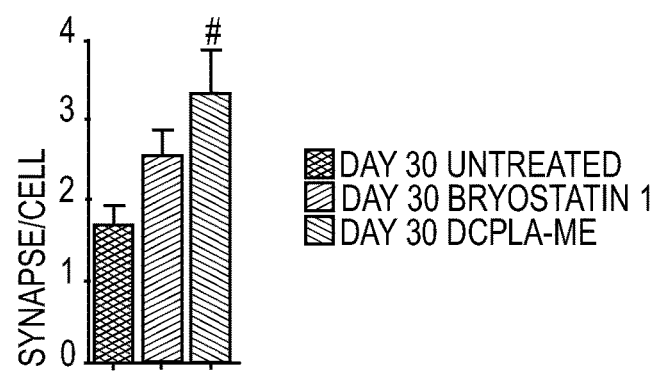
FIG. 15I—Number of synapses per cell increased in DCPLA-ME treated cells. Data are represented as mean±SE*represents significance with respect to day 1 neurons and # represents significance with respect to untreated 40 day or 30 day neurons. (* p<0.05,  p<0.005 and  p<0.0005).

Punctate colocalization of PSD-95 and synaptophysin is accepted as an indicator of synapses. See, e.g., Barker et al. (2008) *J Neurosci* 28, 8150-8160; Ippolito et al. (2010) *J Vis Exp* 16(45), 2270. FIG. 15H shows that the number of synapses was significantly increased in the DCPLA-ME treated cells, suggesting that PKC-ε and PKC-ε activation enhances synaptogenesis or synaptic maintenance.

Example 18

Bryostatin-1 Translocated PKC-ε and PKC-α to the Membrane

To study isoform specificity of Bryostatin-1, SH-SY5Y cells were treated with Bryostatin-1 (0.27 nM) for 0, 5, 15, 30, and 60 min, and the samples were prepared for SDS-PAGE as described in the above under "General Procedures." Western blot was performed on the samples as described above. Equal amounts of proteins were loaded in each lane (20 μg) for both the cytosol and membrane fractions. Activation of PKC was calculated as the percentage of total PKC in the membrane (membrane/cytosol+membrane).

Figure 16A:
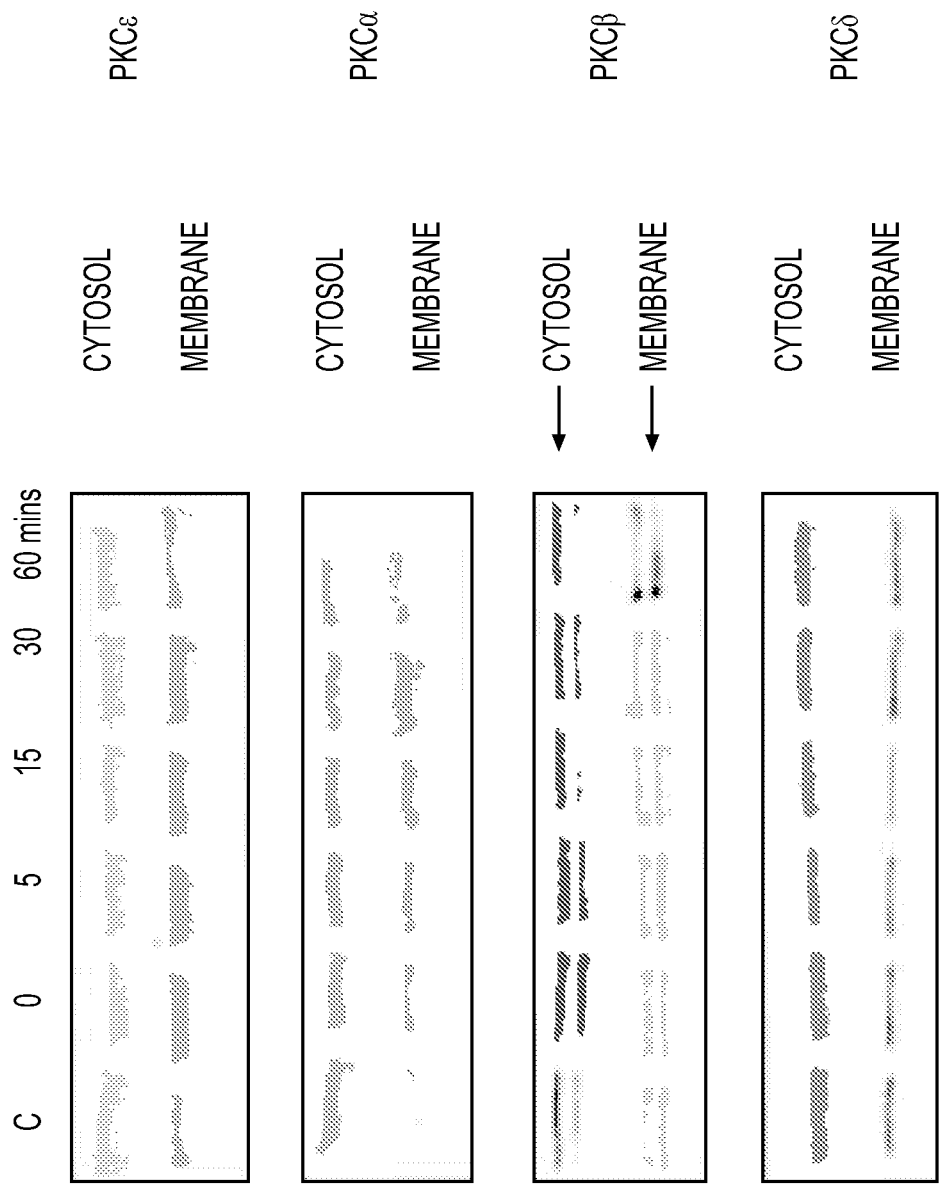
FIG. 16: Translocation of PKC isoforms in SH-SY5Y cells treated with Bryostatin-1 (0.27 nM) after 0, 5, 15, 30, and 60 min. (* represents p<0.05,  represents p<0.005, and * represents p<0.0005).
Figure 16B:
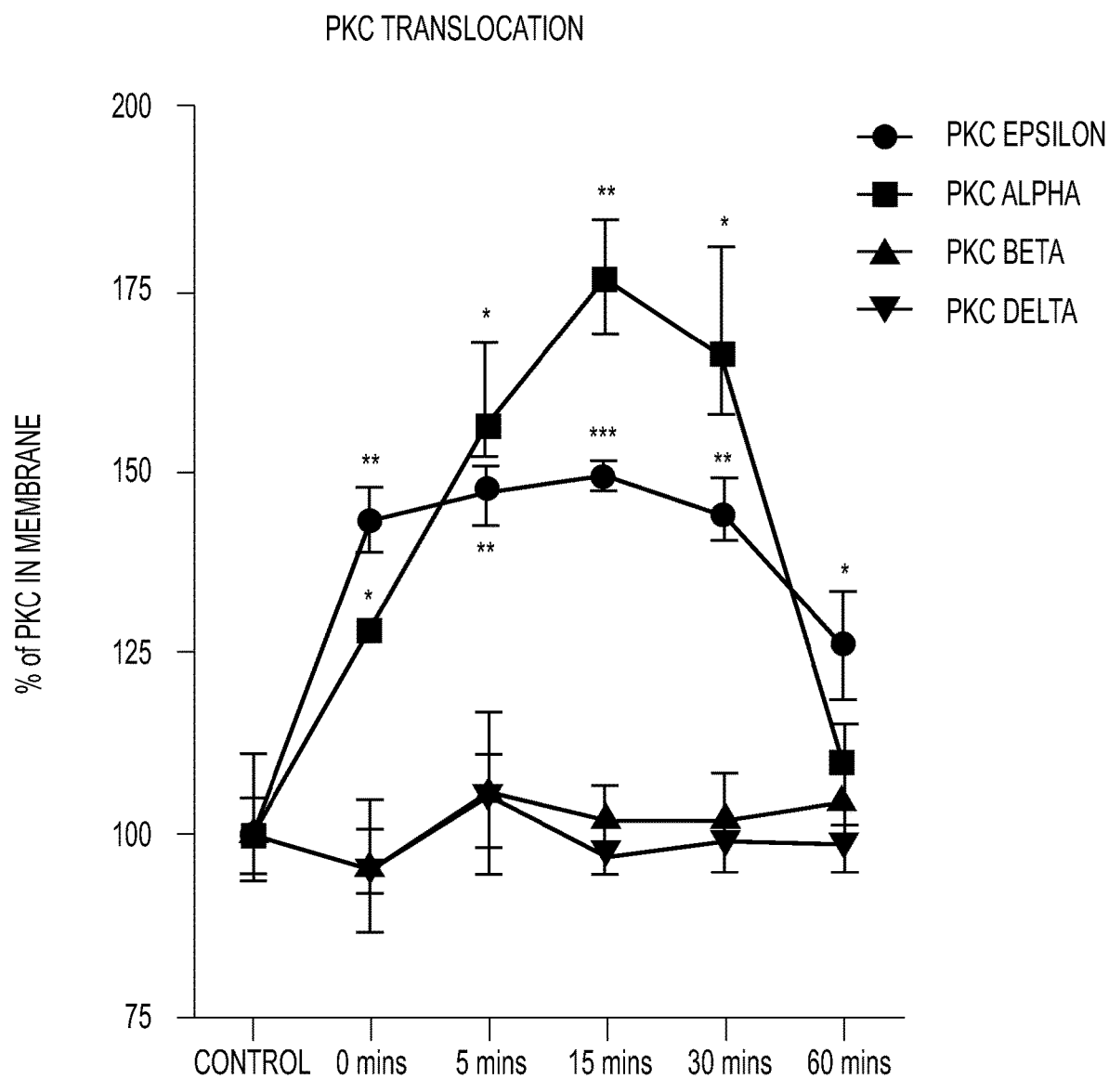

PKC-ε and PKC-α showed significant increases in translocation at 0, 5, 15, and 30 min (FIG. 16). PKC-α came down to baseline at 60 min but PKC-ε remained activated at 60 min. Three independent experiments were performed for each sample and data in the graph represents mean±SE. The data indicate that Bryostatin-1 at 0.27 nM shows isoform specificity for PKC-ε and PKC-α.

Example 19

Bryostatin-1 Induced Interaction of PKC-ε and PKC-α with RACK1

Figure 17A:
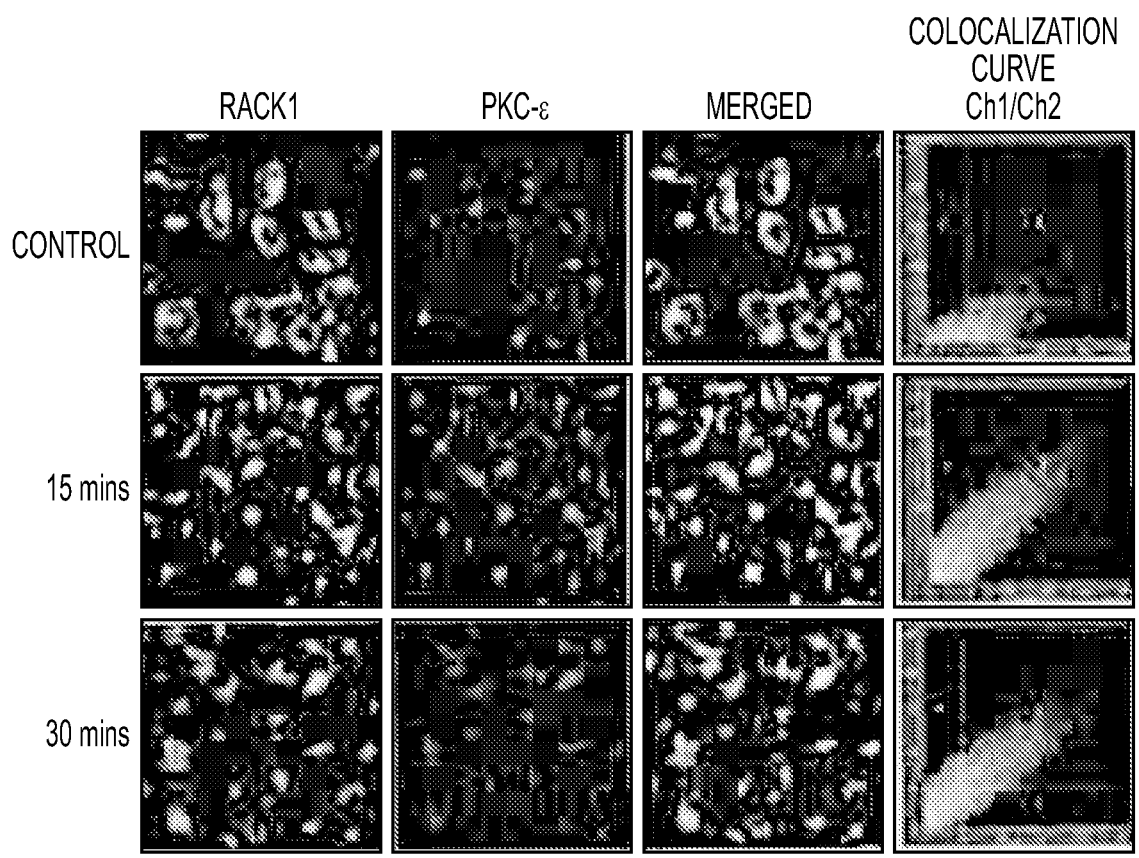
FIG. 17A: Bryostatin-1 induces interaction of PKC-α and PKC-ε with RACK1. Images of RACK1 and PKC-ε (top) or PKC-α (bottom) were taken after treatment with Bryostatin-1 (0.27 nM) at 0, 15, and 30 min and merged to reveal the colocalization of the PKC with RACK1. The fourth column shows the colocalization curve for channel 1 and channel 2.
Figure 17A:
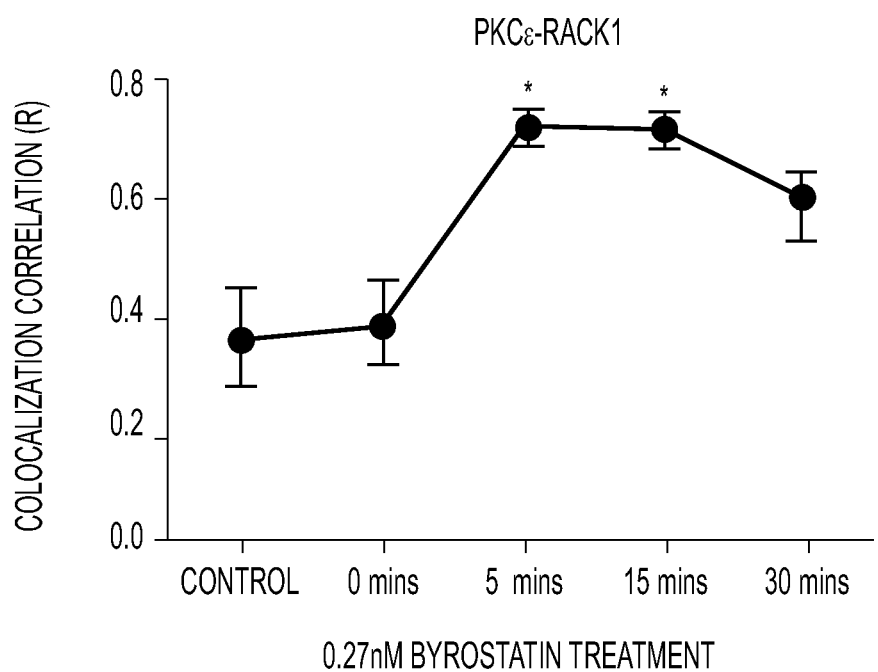
Figure 17A:
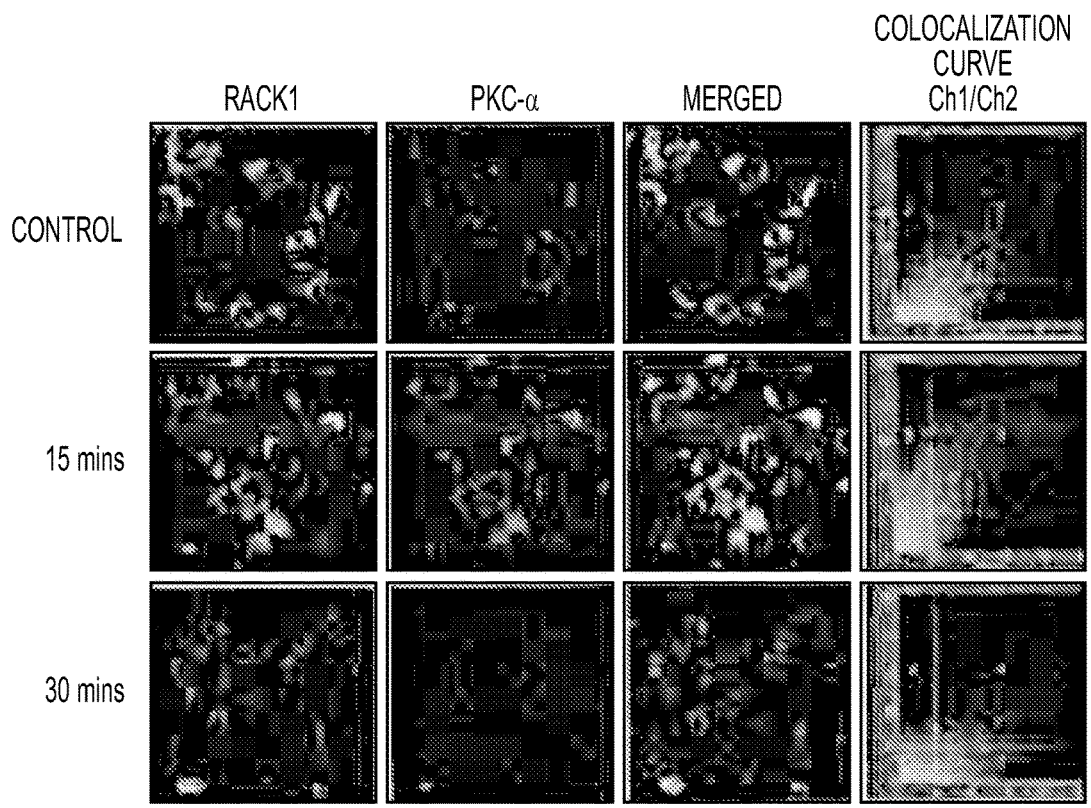
Figure 17A:
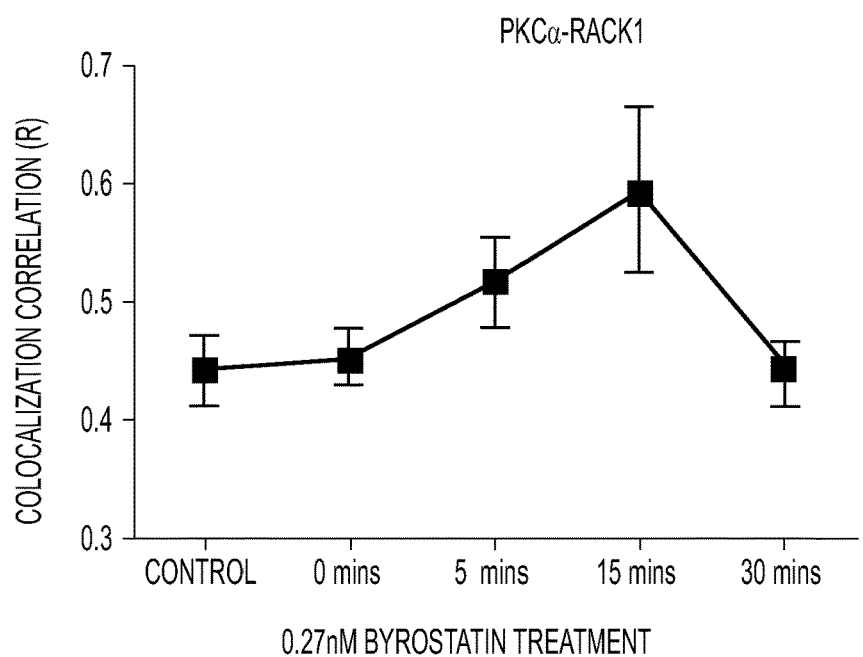

Cells were plated in chambered slides and treated with 0.27 nM Bryostatin-1 for 0, 5, 15, and 30 min and then prepared for confocal analysis as described above. As shown in FIG. 17A, PKC-ε and PKC-α relocated to the membrane and showed association with RACK1 when treated with Bryostatin-1. PKC-ε-RACK1 showed significant increase in colocalization correlation at 5 min (R=0.71) and 15 min (R=0.72) compared to control (R=0.34). PKC-α showed maximum increase in colocalization with RACK1 at 15 min (R=0.58). The association between PKC-ε and RACK1 was more pronounced that for PKC-α and RACK1. PKC-ε and RACK1 colocalization in the membrane followed the same time course as activation of enzymatic activity (p=0.0140 at 5 min). PKC-α colocalization decreased at 30 min. No significant increase in colocalization correction between PKC-β-RACK1 and PKC-δ-RACK1 was observed (data not shown).

Figure 17B:
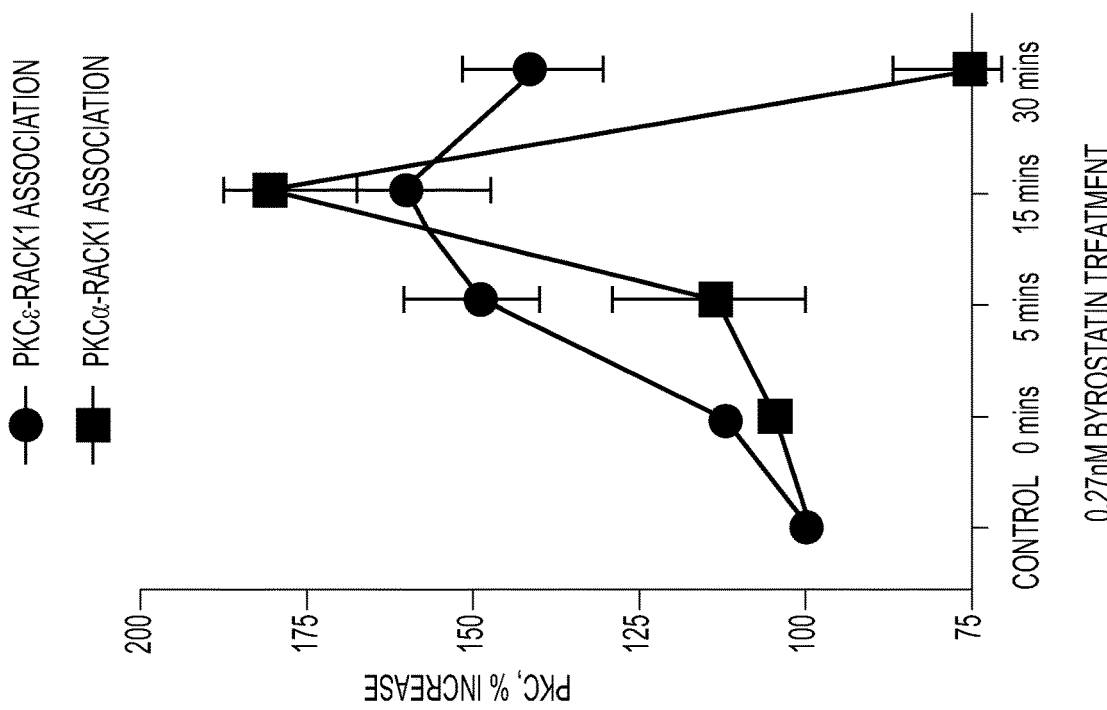
FIG. 17B: RACK1 immunoprecipitation of cells treated with Bryostatin-1 (0.27 nM), measured at 0, 5, 15, and 30 min. "C" being control, "M" being markers. Data are represented as the mean±SE of three independent experiments (* represents p<0.005;  represents p<0.005; and * represents p<0.0005).
Figure 17B:
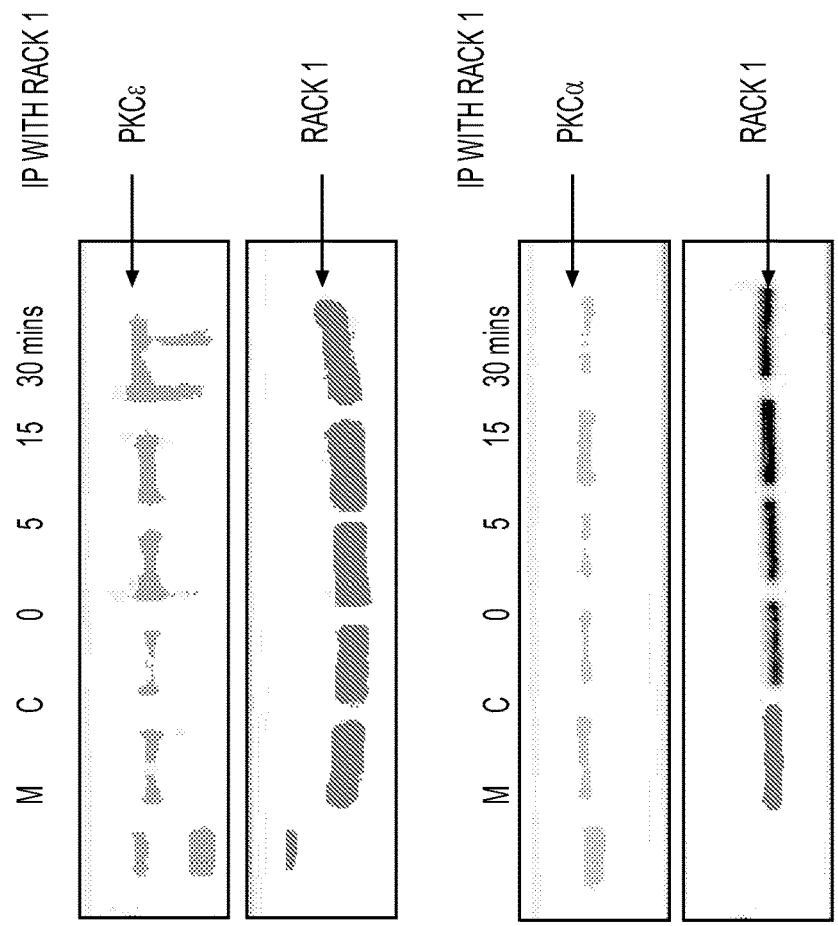

Next, cells were prepared according to the coimmunoprecipitation methods discussed above. RACK1 immunoprecipitation showed association of PKC-ε and PKC-α with RACK1 upon Bryostatin-1 induced activation (FIG. 17B). PKC-ε-RACK1 interaction increased significantly at 5, 15, and 30 min, while PKC-α-RACK1 interaction increased at 15 min but decreased below the control level at 30 min. The results confirmed the observation above that there was no significant increase in colocalization correction between PKC-β-RACK1 and PKC-δ-RACK1.

As a whole, this data further illustrate that Bryostatin-1 at 0.27 nM shows isoform specificity for PKC-ε and PKC-α, and PKC-ε especially.

Further, RACK1 is reported to mediate the interaction between PKC-ε and integrin β chain leading to adhesion, spreading and motility in glioma cells. See Besson et al. (2002) *J Biol Chem* 277, 22073-22084. The above data in combination with these previous reports suggest that the Bryostatin-1-mediated association of PKC-ε with RACK1 may participate in adhesion and enhance neurite formation.

Example 20

Figure 18:
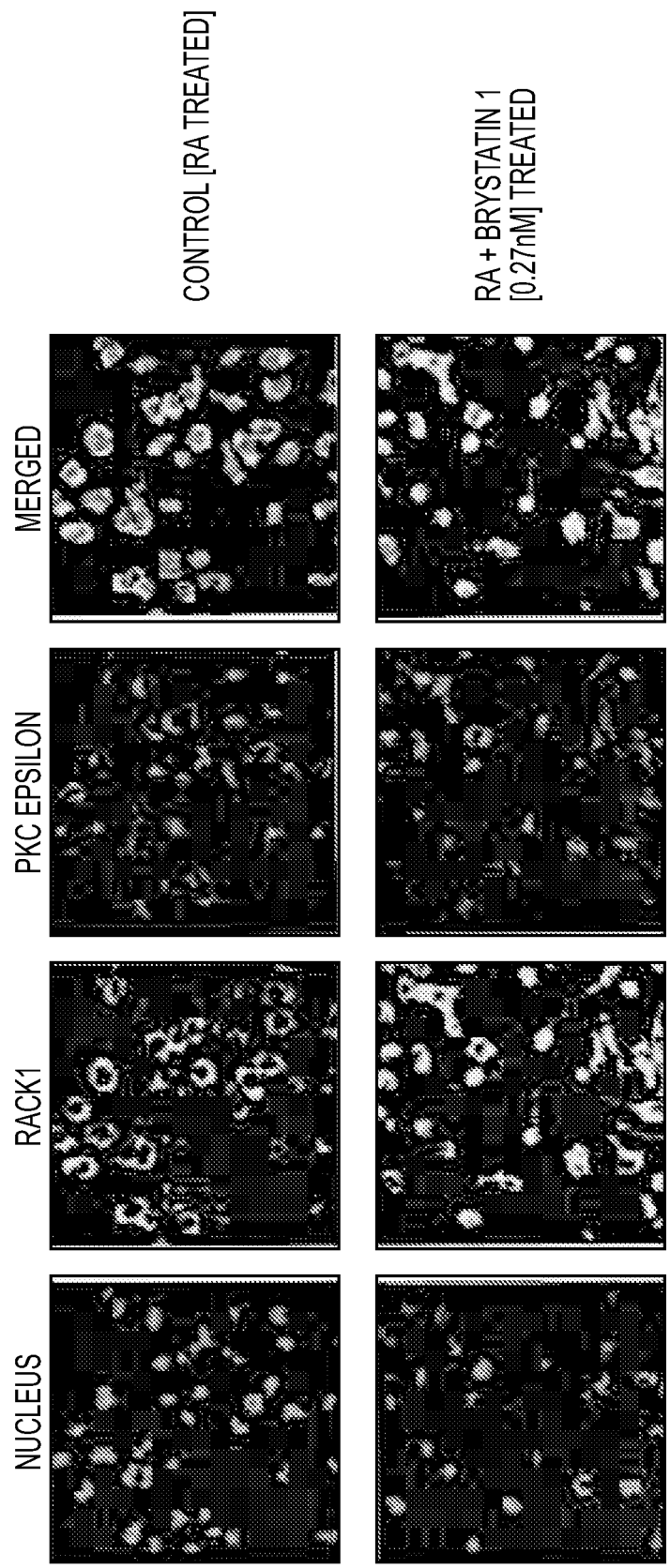
FIG. 18: Confocal images of cells treated with retinoic acid ("RA") and cells treated with RA and Bryostatin-1 at 72 hr. The first column (from the left) is the nucleus stained with DAPI, the second column is RACK1, the third column is PKC-ε, and the last is the merged image showing colocalization.

Treatment with RA and Bryostatin-1 Differentiated SH-SY5Y Neuroblastoma Cells and LED to Synaptic Networks PKC-ε activators are reported to be potent neuroprotective agents that increase and/or prevent the loss of the number of dendritic spines and synapses under conditions of training, hypoxia, aging, and increased levels of the toxic AD protein, A-β. See Hongpaisan et al. (2011) *J Neurosci* 31, 630-643; see also Nelson et al. (2009) *Trends Biochem Sci* 34, 136-145. Accordingly, RA was used to differentiate SH-SY5Y cells and then treated with Bryostatin-1 as described above. RA-pretreated cells incubated with 0.27 nM Bryostatin-1 showed extensive neurite outgrowth and intercellular networks at 24 hr compared to the untreated cells, RA-only and Bryostatin-1-only treated cells (data not shown). In fact, confocal images of the RA-treated cells and RA and Bryostatin-1-treated cells showed extended neurites and intercellular networks at 72 hrs (FIG. 18). The images further showed that PKC-ε and RACK1 were colocalized in the neurites.

Example 21

Cells Treated with Bryostatin-1 and RA Showed Increased Expression of Synaptic Marker Proteins Untreated primary cells (control cells), cells treated with RA, and cells treated with RA and Bryostatin-1 were prepared for microscopy and Western blot analysis. The expression of three presynaptic neuronal markers (synaptophysin, bassoon, and synapsin) and two postsynaptic markers (PSD-95 and neuroligin-1) was measured by immunofluorescence staining as described. Expression and localization of neurite, MAP-2 and β-tubulin III, were also analyzed.

Figure 19A:
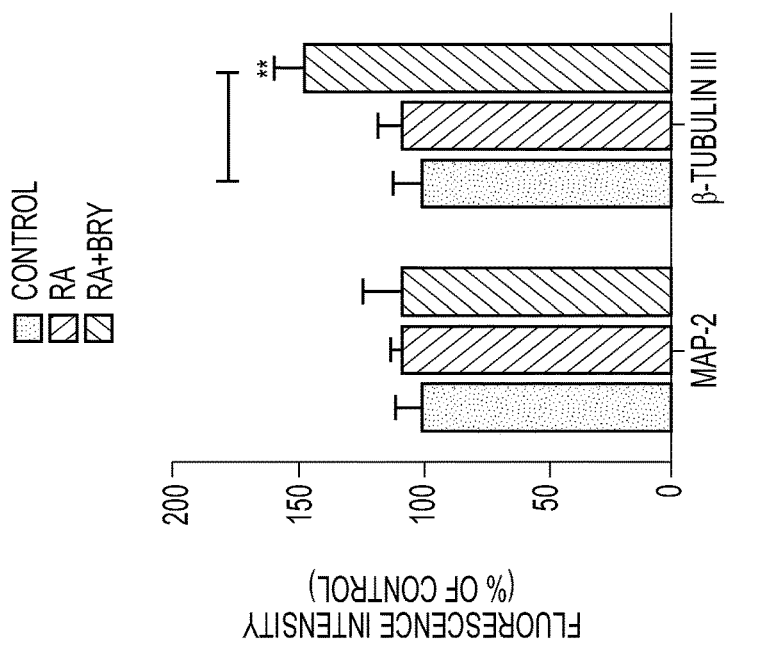
FIG. 19A: Confocal images (and graphical representation) of untreated cells ("Control"), retinoic acid-treated cells ("RA"), and cells treated with RA and Bryostatin-1 ("RA+Bry") at 72 hr. The first column (from the left) is nucleus stained with DAPI, the second column is MAP-2, the third column is β-tubulin III, and the last is the merged image of the first three.
Figure 19A:
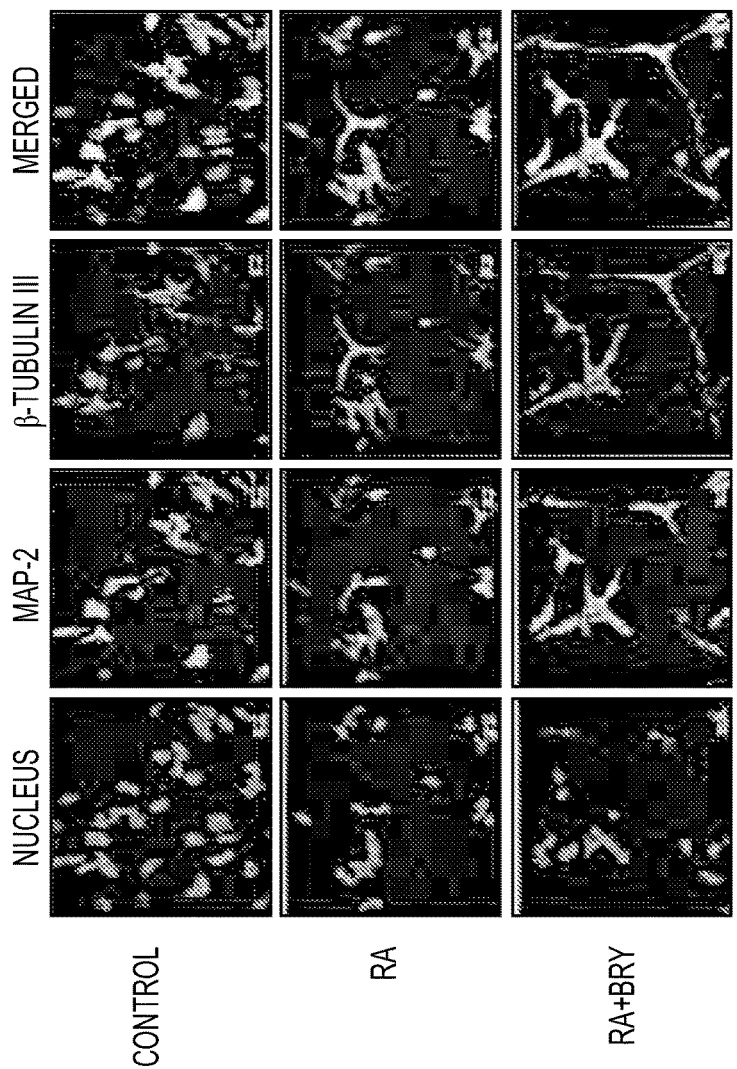
Figure 19B:
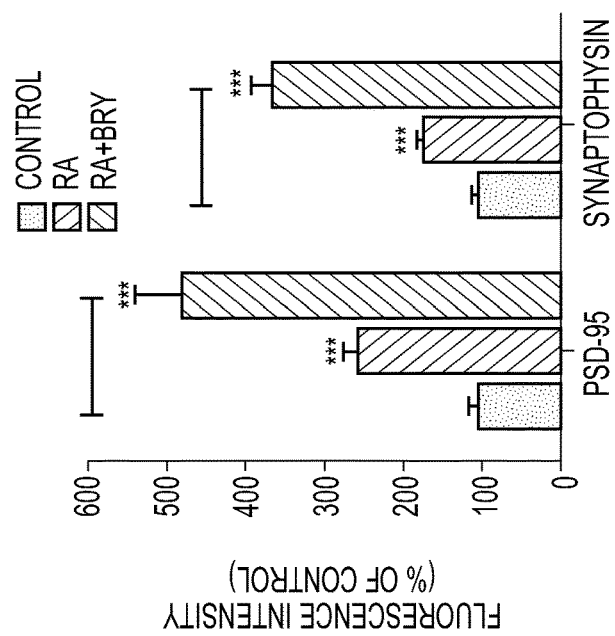
FIG. 19B: Confocal images (and graphical representation) of untreated cells ("Control"), retinoic acid-treated cells ("RA"), and cells treated with RA and Bryostatin-1 ("RA+
Figure 19B:
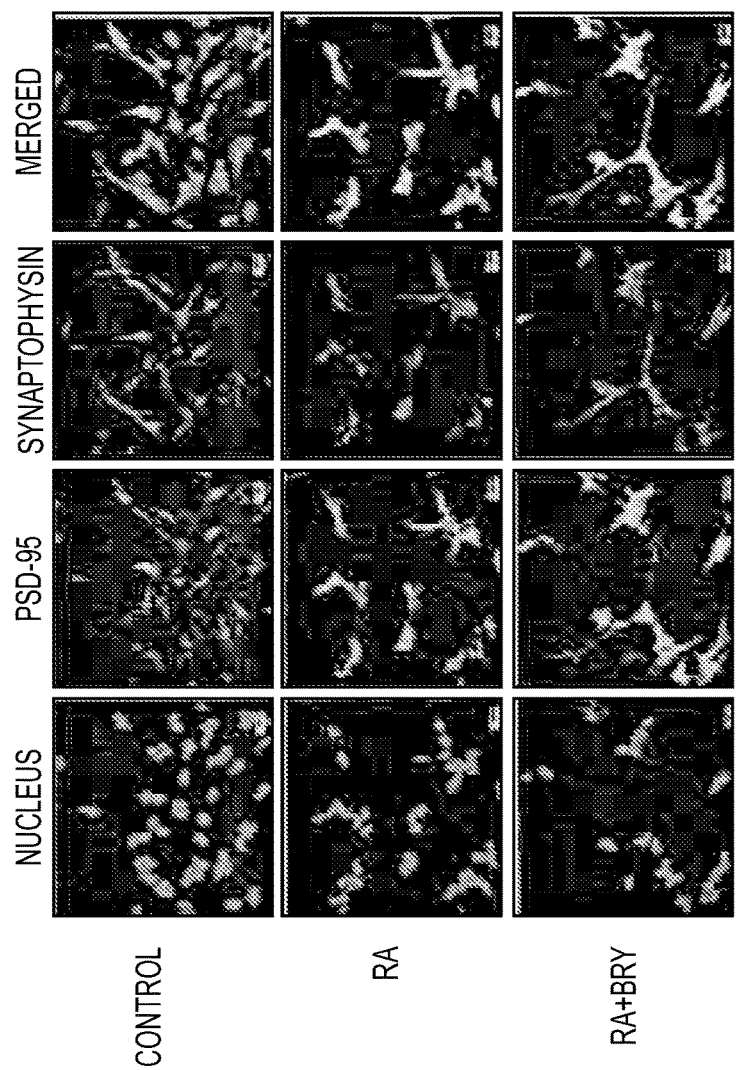

Confocal imaging of immunofluorescently-stained cells showed no significant change for MAP-2 in the cells treated with RA and Bryostatin-1, but β-tubulin III increased by 1.5 fold (FIG. 19A). Imaging also showed a significant increase in synaptophysin by 3.5-fold in the cells treated with RA and Bryostatin-1 ($p<0.0001$) as compared to untreated and RA-treated cells ($p<0.0001$) (FIG. 19B). Treatment with RA and Bryostatin-1 also increased PSD-95 expression by 4.5-fold compared to control ($p=0.0003$) and RA-treated cells ($p<0.001$) (FIG. 19B). A similar increase in expression of synapsin, bassoon, and neuroligin 1 was also noticed in cells treated with RA and Bryostatin-1 at 72 hr. (FIG. 20). In differentiated cells, the markers were found localized in the neurites.

Immunoblot analysis (FIG. 21) showed a 2-fold increase of synaptophysin expression and a 1.5-fold increase of β-tubulin expression in cells treated with RA and Bryostatin-1 (0.27 nM) compared to untreated or RA-treated cells after 72 hr ($p<0.005$), confirming the immunofluorescence data. Bryostatin-1 alone increased synaptophysin expression by 50%.

The increases in both pre- and postsynaptic protein indicate a dramatic increase in the formation of synapses upon treatment with RA and Bryostatin-1. These observations suggest that RA and PKC act synergistically for differentiation and formation of synapses and synaptic networks, as cells treat with RA only did not show much change in synaptophysin or PSD-95.

Example 22

RA and Bryostatin-1 Prolonged Activation of PKC-ε

Four separate experiments were undertaken: (1) RT-PCR was performed on untreated (control), RA-treated, Bryostatin-1-treated, and cells treated with RA and Bryostatin-1 as described above to estimate the mRNA level of PKC-ε; (2) untreated cells, RA-treated cells, and cells treated with RA and Bryostatin-1 were subject to the PKC assay described above; (3) RA-treated cells were subjected to the PKC assay with specific isoforms as described above; and (4) translocation of PKC-ε and PKC-α of RA-treated and cells treated with RA and Bryostatin-1 was measured by immunoblot, with β-tubulin as the loading control.

FIG. 22A shows that PKC-ε transcription was enhanced by RA and activation of PKC-ε by Bryostatin-1 increased that effect. More specifically, cells treated with RA-only and Bryostatin-1-only increased the mRNA level of PKC-ε by 2-fold while treatment with RA and Bryostatin-1 increased the mRNA level of PKC-ε by 3.5-fold ($p=0.0003$). There was no change in PKCα or PKCδ mRNA (data not shown). The fact that there was an increase in the mRNA level in the RA-only cells is consistent with a previous report that RA increases PKC-ε transcription. See Maden, M. (2007) *Nat Rev Neurosci* 8, 755-765.

FIG. 22B shows that, in the membrane, total PKC activity increased significantly ($p<0.005$) in the RA-treated and cells treated with RA and Bryostatin-1 compared to the control at 72 hr. More specifically, the PKC activity in membrane, calculated as a percentage of total PKC activity (cytosol+membrane), showed nearly a 134% increase in cells treated with RA and Bryostatin-1 compared to untreated cells and a 38% increase compared to RA-treated cells. Total PKC activity in the membrane of cells treated with RA and Bryostatin-1 was maintained even after 72 hr, while the PKC activity in the cytosol decreased over time ($p<0.0005$).

FIG. 22C shows that PKC-ε, PKC-α, and PKC-δ are not activated by RA alone. FIG. 22D shows that cells treated with RA and Bryostatin-1 showed no significant activation of PKC α, with a maximum increase by 12% at 48 hr. On the other hand, PKC-ε activation was significantly increased at 12 hr (28%), 24 hr (42%), 48 hr (50%), and even at 72 hr (50%). The prolonged activity was confirmed by the immunofluorescence staining of the RA-treated and cells treated with RA and Bryostatin-1 after 72 hr for PKC-ε and RACK1.

In analyzing these studies, the results show that treatment with RA and Bryostatin-1 prolonged activation of PKC and PKC-ε in particular. As shown in FIG. 22B, total PKC activity was observed up to 72 hr. The same was true when observing PKC ε specifically (FIG. 22D, see also FIG. 18). This is in sharp contrast to the activation of Bryostatin-1 alone, which showed a rapid decline of PKC ε at only 1 hr (FIG. 16).

In cells treated with RA only, PKC-ε transcription increased (FIG. 22A) and total PKC activity increased (FIG. 22B). However, RA did not activated PKC-ε (FIG. 22C).

The rapid downregulation seen in the case of Bryostatin-1-treated cells is presumably due to degradation of the PKC by proteasomal activity. See Lee (1997) *Mol Pharmacol* 51, 439-447. Accordingly, because RA is not activating PKC-ε, it may be possible that the RA is serving to block the proteasomal degradation. Moreover, because PKC-ε transcription is increasing, it is possible that RA is creating a constant pool of PKC-ε such that activity is prolonged even if degradation is occurring. The sustained activity that occurs through the use of RA and Bryostatin-1 is highly desirable for long-term clinical use.

Further, based on the showing PKC-ε-RACK1 colocalization in the neurites (FIG. 18) and the sustained presence of PKC-ε in the membrane (FIG. 22D), it can be speculated that RACK1 localized PKC-ε to the membrane and neurites where it may interact with integrin β chain leading to adhesion, spreading and motility (see Besson, et al. (2002) *J Biol Chem* 277, 22073-22084), and also binding with the F-actin filaments, which other isoforms cannot bind (see Prekeris, et al. (1996) *J Cell Biol* 132, 77-90; 49. Zeidman, et al. (2002) *Mol Biol Cell* 13, 12-24; Prekeris, et al. (1998) *J Biol Chem* 273, 26790-26798; and Saitoh, et al. (2001) *Proc Natl Aced Sci USA* 98, 14017-14021). These interactions may led to neuritic outgrowth and cytoskeleton modification required for synaptic structure rearrangement and spinogenesis.

Example 23

Treatment with RA and Bryostatin-1 Increased PKC-ε and Synaptophysin in Synaptosomes Synaptosomes were prepared from untreated (control) and cells treated with RA (10 μM), Bryostatin-1 (0.27 nM) ("Bry"), or RA and Bryostatin-1 (0.27 nM) as described in the "General Procedures" section above. Western blot analysis was performed after 72 hr.

Synaptosomes of cells treated with RA and Bryostatin-1 showed a large increase in PKC-ε level (3-fold) compared to the untreated cells (p=0.0021) and RA-treated cells (p=0.0027) (FIG. 23A). Bryostatin-1 itself increased the total PKC-ε in synaptosomes by 2-fold, which is 50% more than what it translocated to the membrane (FIG. 23), suggesting that Bryostatin-1 localizes PKC-ε to the synaptosomes where it may phosphorylate important synaptic proteins required for synaptogenesis. RA+Bryostatin 1 treatment increased PSD-95 staining by more than 3 fold in the synaptosomes (FIG. 23B).

Synaptophysin was also increased in the synaptosomes of cells treated with RA and Bryostatin-1 by 2.5 fold (FIG. 23C) suggesting that RA acts in part through activation of PKC-ε in maintaining the synaptic structure and function. Because both PKC-ε and synaptophysin expression increased in the synaptosomes of cells treated with RA and Bryostatin-1, the data suggest that PKC-ε is necessary for enhanced synaptic activity in the synaptosomes.

Based on the data, PKC-ε mediated differentiation of neuroblastoma cells treated with RA and Bryostatin-1 provides a good and functional model of mature neurons, which demonstrate the characteristic markers of neurons such as increased synaptophysin expression in the synaptosomes and increased PSD-95 expression.

Example 24

Treatment with RA and PKC Activators Differentiated Primary Neuron Cells and Leads to Synaptic Networks Seven day old rat hippocampal neurons were treated with RA, Bryostatin-1, RA and Bryostatin-1, DCPLA-ME (a PKC-ε specific activator, 100 nM), or RA and DCPLA-ME for 48 hr. Treatment with RA and a PKC activator (either Bryostatin-1 or DCPLA-ME) was more effective at differentiating the neurons compared to RA-treated cells or cells treated with the corresponding PKC activator alone (FIG. 24). Dendritic branching was increased in the cells treated with RA and a PKC activator, as evidenced by the MAP-2 staining. Similarly, the synaptic vesicle pool increased was also seen by increased synaptophysin.

Example 25

Treatment with RA and Bryostatin-1 was Neuroprotective Against Oligomeric Aβ

Rat hippocampal primary neurons grown on chambered slides were treated with vehicle; RA; ASPDs; ASPD and RA; ASPD and Bryostatin-1; ASPDs, RA, and Bryostatin-1; ASPDs, RA, and DCPLA-ME; PKC-inhibitor [EAVS-LKPT], ASPDs, RA, and Bryostatin-1; or PKC-inhibitor [EAVSLKPT], ASPDs, and RA. All studies used 50 nM ASPDs. The viability of the cells were measured by the MTT assay.

Treatment with RA and Bryostatin-1 was found more neuroprotective on ASPD-treated neurons when compared to Bryostatin-1-treated cells (FIG. 24C). ASPD-treated cells were shown to be quite toxic, reducing viability to 57.61%±1.59 (p<0.005). While Bryostatin-1-treated cells restored viability to 71.38%±2.34, cells treated with RA and Bryostatin-1 showed even greater neuroprotection (81.99%±3.45 viability). Both Bryostatin-1 and DCPLA-ME are PKC activators. However, RA addition may increase the neuroprotective efficacy, depending on the concentration of the PKC activator being used in combination with RA.

Following 20 hr incubation, the ASPD-treated cells and cells treated with ASPD, RA, and Bryostatin-1 were stained for PSD-95 and synaptophysin. Treatment with RA and Bryostatin-1 restored the PSD-95 and synaptophysin levels significantly in ASPD-treated primary neurons (FIG. 24A and FIG. 24B). Mean fluorescence intensity of PSD-95 in the ASPD-treated cells (8.16±1.21) was reduced to 50% compared to the vehicle-treated (control) cells (15.42±2.2), but was restored (14.26±1.72) in cells treated with RA and Bryostatin-1. Similarly, synaptophysin in the control (17.5±1.2) was reduced by ASPD (9.74±2.5) but treatment with RA and Bryostatin-1 restored the synaptophysin level to 14.35±1.67.

The data in FIG. 24 thus suggest that RA and Bryostatin-1 has a better neuroprotective property than either RA or Bryostatin-1 alone.

Example 26

Current Clamp of SH-SY5Y Cells Treated with RA and Bryostatin-1

Whole cell current clamp recordings were made using a Multiclamp 700A computer-controlled microelectrode amplifier and Digidata 1322 digitizer with pCLAMP 9.0 software (Molecular Devices, Union City, Calif., USA). Microelectrodes with tip resistances of 2-8 Megohms were pulled from 1.5 mm borosilicate glass. Data were collected at a sampling rate of 20-40 kHz and filtered at 10-20 kHz; some traces were processed through smoothing procedures implemented in Gnuplot (v 3.7; http://www.gnuplot.info/). Some data were collected at higher sampling rates to eliminate effects of sampling on action potential amplitude.

Pipettes for whole-cell recording were filled with: potassium gluconate (130 mM), NaCl (4 mM), MgCl$_2$ (2 mM), Hepes (10 mM), EGTA (0.2 mM), and NaATP (2 mM). All recordings were made at room temperature. Action potentials were elicited by injecting step currents into the treated neuroblastoma cells and were not observed in untreated neuroblastoma cells. Spontaneous excitatory/inhibitory postsynaptic potentials (E/IPSP) were recorded for treated neuroblastoma cells by using a listening protocol (zero current injection) in which cells are at the resting membrane potential (Chirila et al., *J Physiol.* 2007 Oct. 1; 584(Pt 1):167-90. Epub 2007 Aug. 9).

The goal of this experiment was to convert neuroblastoma cells into neuron-like cells capable of forming functional synapses. FIG. 25 showed that rectification is occurring, which might be indicative of action potentials. While these data are too preliminary to evaluate their indication of functional synapses, further recordings using these techniques may provide a credible measure of the functionality of these connections. The creation of functional synapses in an in vitro situation such as this could be extremely valuable. It could provide a simple and cheap means for testing the ability of potential drugs to regenerate synapses as compared to current methods, which require animal studies.

Example 27

PKC-ε Knockdown Prevents RA+Bryostatin 1 Mediated Differentiation

Figures 26A, 26B:
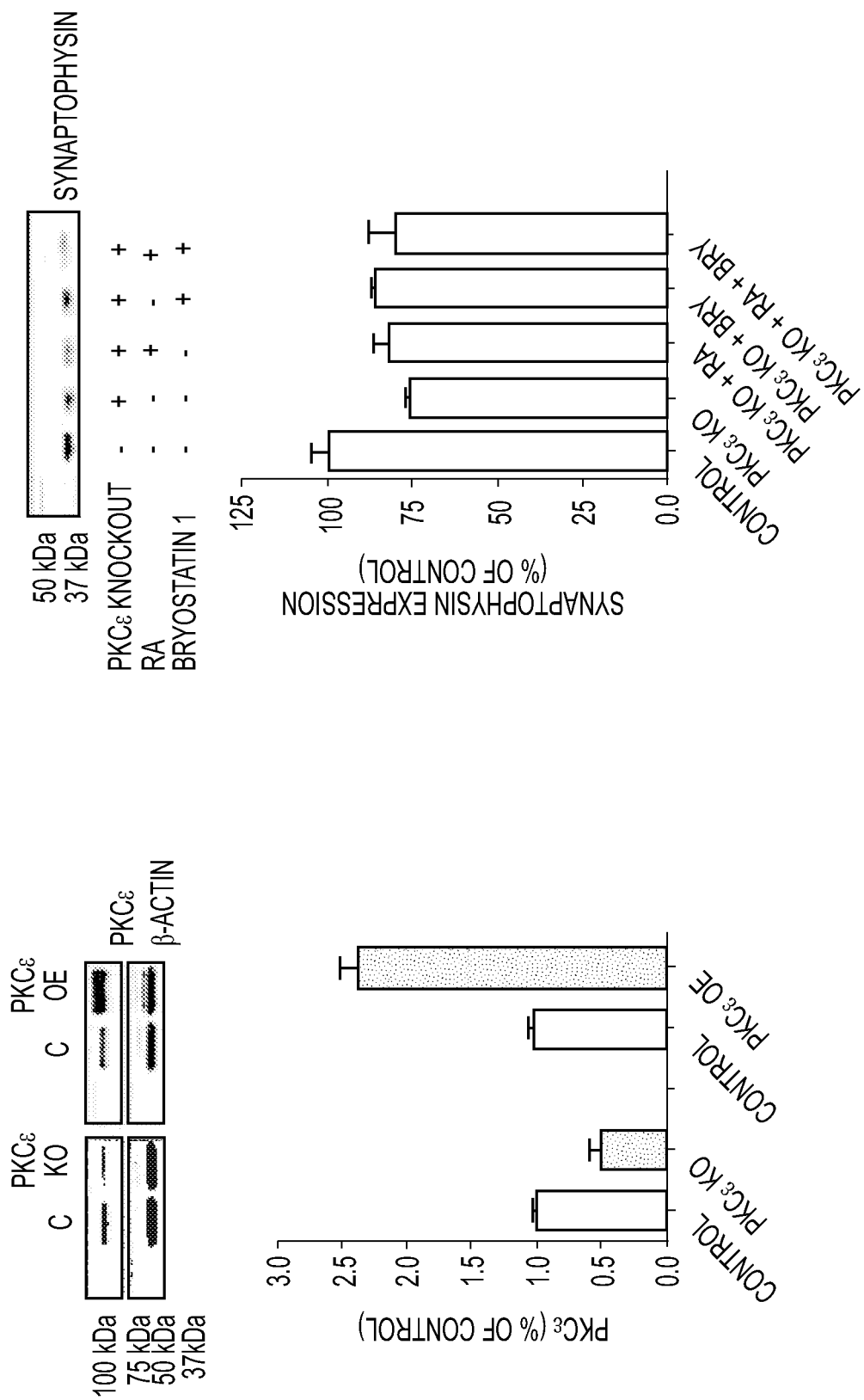
Figure 26C:
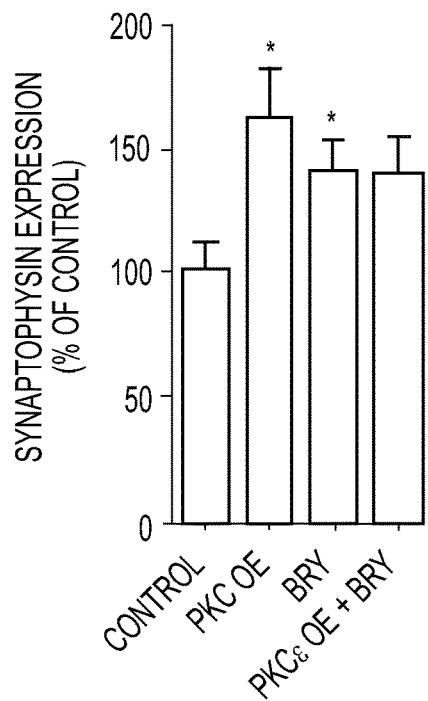
Figure 26D:
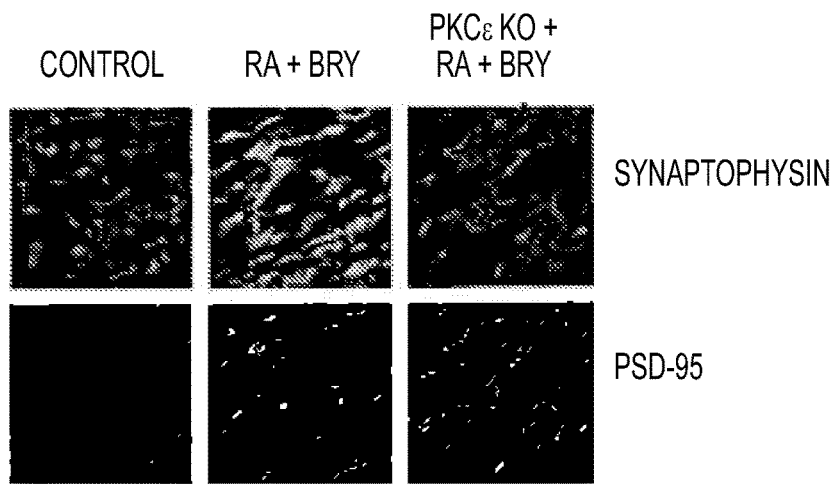
Figure 26F:
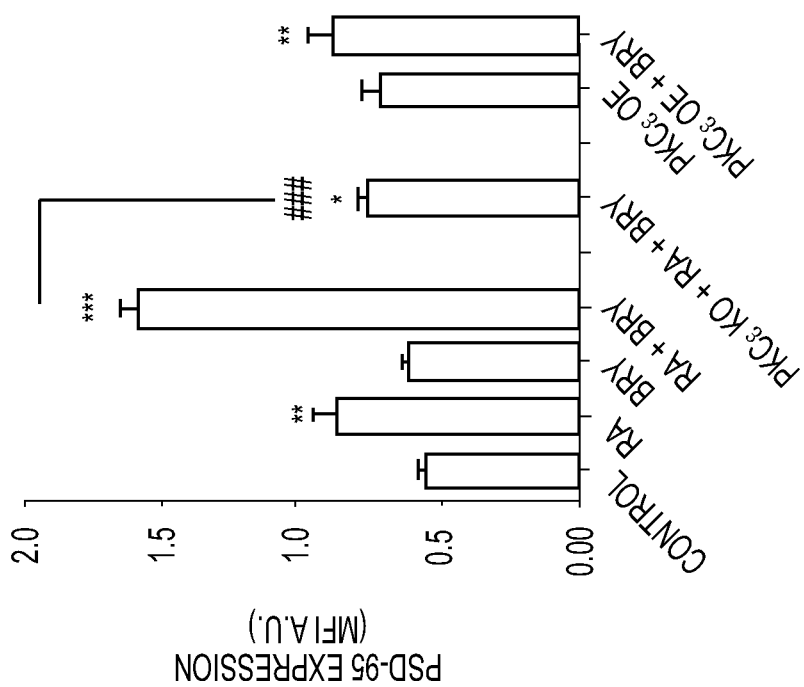
Figure 26E:
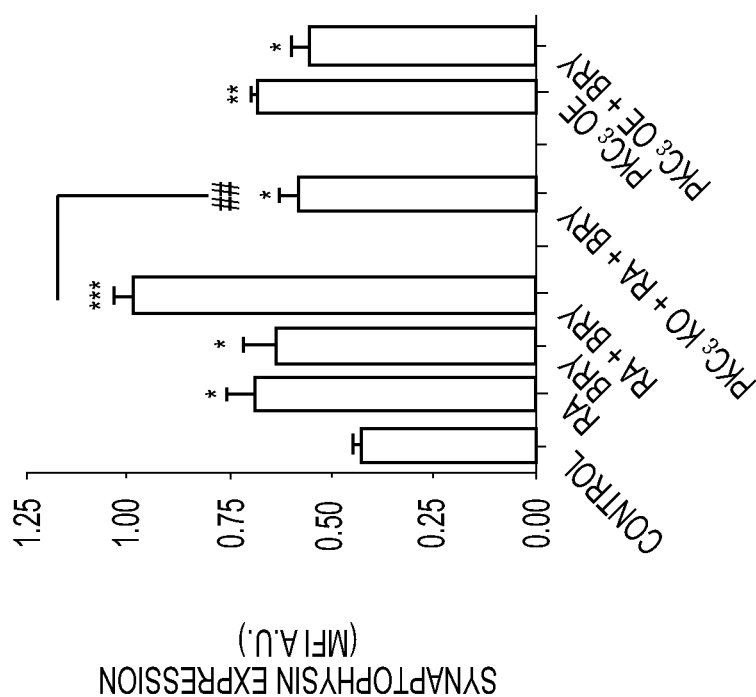

To confirm the role of PKC-ε in RA+Bryostatin 1 mediated differentiation, siRNA mediated PKCε knockdown cells were used. PKCε-siRNA cells ("PKCε KO") reduced the expression of PKCε by 50% (FIG. 26A). The PKC-ε knockdown cells treated with RA+bryostatin 1 ("PKCεKO+ RA+Bry") showed reduced synaptophysin and PSD-95 staining (FIGS. 26B, D, E & F). PKC-ε overexpression ("PKCε OE") increased synaptophysin (FIGS. 26C & E). RA+bryostatin 1 increased synaptophysin staining in untreated cells but not PKCε KO cells (FIG. 26E). A similar effect was seen for PSD-95 (FIG. 26F). These results indicate that PKC-ε is required for induction of pre- and postsynaptic proteins by RA+bryostatin 1.

Example 28

RA+Bryostatin 1 Enhances Differentiation in Rat Primary Neurons

The effect of RA+bryostatin 1 on development of primary neurons was also investigated. Seven day old rat hippocampal neurons were treated with RA, bryostatin 1, RA+bryostatin 1, DCPLA-methyl ester ("DCPLA-ME") or RA+DCPLA-ME for 48 hr. RA+bryostatin produced a greater increase of MAP2 and synaptophysin than RA or bryostatin alone (FIGS. 27A & C). Fractal dimension measures showed significant increase of dendritic branching in the DCPLA-ME (1.40±0.03), RA+bryostatin 1 (1.45±0.035) and RA+DCPLA-ME (1.36±0.01) treated cells (FIG. 27B). Synaptophysin staining was increased by RA and DCPLA-ME, suggesting an increase in the synaptic vesicle pool (FIG. 27C).

What is claimed is:

1. A method for treating Alzheimer's disease or Parkinson's disease comprising administering to a patient in need thereof a cyclopropanated PUFA-cholesterol conjugate and retinoic acid, wherein the cyclopropanated PUFA-cholesterol conjugate is selected from:

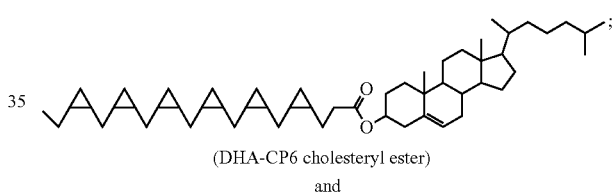

(DHA-CP6 cholesteryl ester)

and

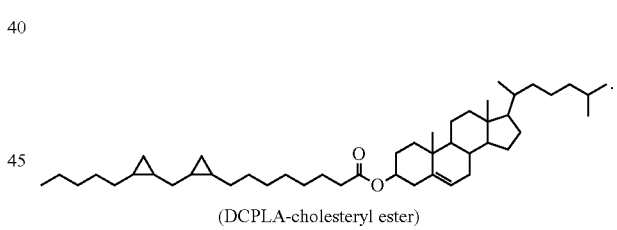

(DCPLA-cholesteryl ester)

2. A method for treating Alzheimer's disease or Parkinson's disease comprising administering to a patient in need thereof a cyclopropanated PUFA-cholesterol conjugate and at least one retinoid, wherein the cyclopropanated PUFA-cholesterol conjugate is selected from:

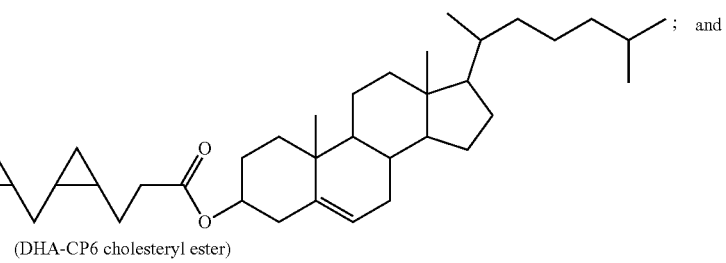

(DHA-CP6 cholesteryl ester)

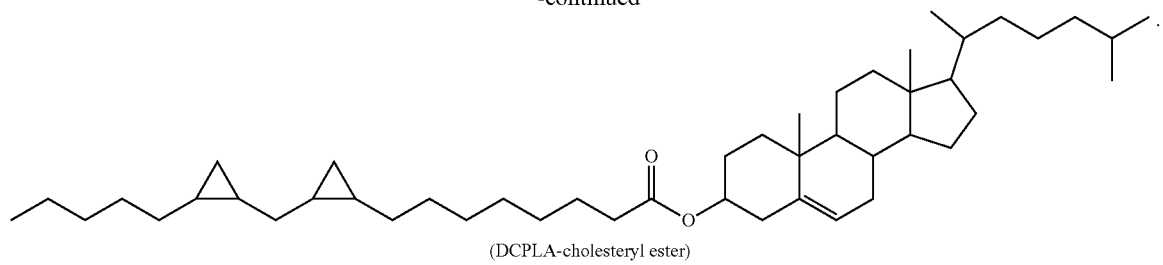

(DCPLA-cholesteryl ester)

3. The method according to claim 2, wherein the at least one retinoid is chosen from retinoic acid, N-(4-hydroxyphenyl) retinamide ("4-HPR"), 4-(5, 5, 8, 8-Tetramethyl-5, 6, 7, 8-tetrahydronaphthalen-2-ylethynyl) benzoic acid ("ec23"), 9-cis retinoic acid, 13-cis retinoic acid, all-trans-4-hydroxyretinoic acid, all-trans-4-oxoretinoic acid, 3,4, didehydroretinoic acid, retinol, retroretinol, all-trans-4-hydroxyretinol, all-trans-4-oxoretinol, 14-hydroxy-4, 14-retroretinol, retinaldehyde, lycopene, apo-1 0'-lycopenoic acid, and acycloretinoic acid.

4. The method according to claim 2, wherein the at least one retinoid is retinoic acid.

5. The method according to claim 2, wherein the at least one retinoid is administered to a patient in need thereof before administration of the at least one cyclopropanated PUFA-cholesterol conjugate.

6. The method according to claim 2, wherein the at least one retinoid is administered to a patient in need thereof after administration of the cyclopropanated PUFA-cholesterol conjugate.

7. The method according to claim 2, wherein the at least one retinoid and the cyclopropanated PUFA-cholesterol conjugate are administered simultaneously.

* * * * *